(12) United States Patent
Ramstack

(10) Patent No.: US 11,464,871 B2
(45) Date of Patent: *Oct. 11, 2022

(54) METHODS AND SYSTEMS FOR POLYMER PRECIPITATION AND GENERATION OF PARTICLES

(71) Applicant: Novartis AG, Basel (CH)

(72) Inventor: J. Michael Ramstack, Lunenberg, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/984,686

(22) Filed: May 21, 2018

(65) Prior Publication Data

US 2018/0264136 A1  Sep. 20, 2018

Related U.S. Application Data

(63) Continuation of application No. 14/042,996, filed on Oct. 1, 2013, now abandoned.

(60) Provisional application No. 61/708,797, filed on Oct. 2, 2012.

(51) Int. Cl.
*A61K 47/69* (2017.01)
*A61K 47/59* (2017.01)
*A61K 47/61* (2017.01)

(52) U.S. Cl.
CPC .......... *A61K 47/6951* (2017.08); *A61K 47/59* (2017.08); *A61K 47/61* (2017.08)

(58) Field of Classification Search
CPC ............................ A61K 47/6951; A61K 47/61
See application file for complete search history.

(56) References Cited

U.S. PATENT DOCUMENTS

| | | | |
|---|---|---|---|
| 3,426,011 A | 2/1969 | Parmerter et al. |
| 3,453,257 A | 7/1969 | Parmerter |
| 3,472,835 A | 10/1969 | Buckler et al. |
| 3,502,601 A | 3/1970 | Case et al. |
| 3,654,261 A | 4/1972 | Johnson |
| 4,291,013 A | 9/1981 | Wahlig et al. |
| 4,347,234 A | 8/1982 | Wahlig et al. |
| 4,367,072 A | 1/1983 | Vogtle et al. |
| 4,438,253 A | 3/1984 | Casey et al. |
| 4,525,495 A | 6/1985 | Dorman et al. |
| 4,526,938 A | 7/1985 | Churchill et al. |
| 4,535,152 A | 8/1985 | Szejtli et al. |
| 4,570,629 A | 2/1986 | Widra |
| 4,572,832 A | 2/1986 | Kigasawa et al. |
| 4,582,865 A | 4/1986 | Balazs et al. |
| 4,587,268 A | 5/1986 | Pfirrmann |
| RE32,268 E | 10/1986 | Gordon |
| 4,625,014 A | 11/1986 | Senter et al. |
| 4,638,045 A | 1/1987 | Kohn et al. |
| 4,652,441 A | 3/1987 | Okada et al. |
| 4,675,381 A | 6/1987 | Bichon |
| 4,727,064 A | 2/1988 | Pitha |
| 4,745,160 A | 5/1988 | Churchill et al. |
| 4,746,734 A | 5/1988 | Tsuchiyama et al. |
| 4,764,604 A | 8/1988 | Muller |
| 4,774,329 A | 9/1988 | Friedman |
| 4,776,984 A | 10/1988 | Traitler et al. |
| 4,814,470 A | 3/1989 | Colin et al. |
| 4,818,542 A | 4/1989 | DeLuca et al. |
| 4,841,081 A | 6/1989 | Toda et al. |
| 4,877,778 A | 10/1989 | Carpenter et al. |
| 4,887,778 A | 12/1989 | Soth et al. |
| 4,898,654 A | 2/1990 | Toda et al. |
| 4,902,788 A | 2/1990 | Zemel et al. |
| 4,941,996 A | 7/1990 | Trend et al. |
| 5,098,793 A | 3/1992 | Rohrbach et al. |
| 5,100,669 A | 3/1992 | Hyon et al. |
| 5,143,854 A | 9/1992 | Pirrung et al. |
| 5,148,854 A | 9/1992 | Nakamoto |
| 5,183,883 A | 2/1993 | Tanaka et al. |
| 5,208,316 A | 5/1993 | Yoshinaga |
| 5,219,980 A | 6/1993 | Swidler |
| 5,275,824 A | 1/1994 | Carli et al. |
| 5,276,088 A | 1/1994 | Yoshinaga |
| 5,330,768 A | 7/1994 | Park et al. |
| 5,357,012 A | 10/1994 | Nussstein et al. |
| 5,376,509 A | 12/1994 | Yoshimoto et al. |
| 5,405,783 A | 4/1995 | Pirrung et al. |
| 5,424,186 A | 6/1995 | Fodor et al. |
| 5,438,072 A | 8/1995 | Bobee et al. |
| 5,439,686 A | 8/1995 | Desai et al. |
| 5,482,719 A | 1/1996 | Guillet et al. |
| 5,488,102 A | 1/1996 | Vetter |
| 5,498,421 A | 3/1996 | Grinstaff et al. |

(Continued)

FOREIGN PATENT DOCUMENTS

| | | |
|---|---|---|
| CA | 2497792 A1 | 3/2004 |
| CA | 2781669 A1 | 5/2011 |
| CN | 1308639 A | 8/2001 |
| CN | 1343205 A | 4/2002 |
| CN | 1534036 A | 10/2004 |
| CN | 1216057 C | 8/2005 |
| CN | 1694728 A | 11/2005 |
| EP | 0258780 A2 | 3/1988 |
| EP | 0502194 A1 | 9/1992 |
| EP | 0587106 A2 | 3/1994 |
| EP | 0730869 A1 | 9/1996 |
| EP | 1243276 A1 | 9/2002 |
| EP | 1525890 A1 | 4/2005 |

(Continued)

OTHER PUBLICATIONS

Dong, Y. et al., International Journal of Pharmaceutics, "A continuous and highly effective static mixing process for antisolvent precipitation of nanoparticles of poorly water-soluble drugs", 2010, vol. 386, pp. 256-261 (Year: 2010).*

(Continued)

*Primary Examiner* — Bahar Craigo
(74) *Attorney, Agent, or Firm* — Lando & Anastasi, LLP

(57) ABSTRACT

Processes for precipitating polymers from a polymer-containing solution are disclosed.

21 Claims, 4 Drawing Sheets

(56) References Cited

U.S. PATENT DOCUMENTS

| | | |
|---|---|---|
| 5,510,240 A | 4/1996 | Lam et al. |
| 5,529,915 A | 6/1996 | Phillips et al. |
| 5,547,932 A | 8/1996 | Curiel et al. |
| 5,549,974 A | 8/1996 | Holmes |
| 5,571,882 A | 11/1996 | Vetter |
| 5,608,015 A | 3/1997 | Yoshinaga |
| 5,612,389 A | 3/1997 | Chabrecek et al. |
| 5,635,383 A | 6/1997 | Wu et al. |
| 5,652,347 A | 7/1997 | Pouyani et al. |
| 5,656,611 A | 8/1997 | Kabanov et al. |
| 5,679,773 A | 10/1997 | Holmes |
| 5,688,488 A | 11/1997 | Low et al. |
| 5,691,316 A | 11/1997 | Agrawal et al. |
| 5,693,768 A | 12/1997 | Bachmann et al. |
| 5,698,535 A | 12/1997 | Geczy et al. |
| 5,698,582 A | 12/1997 | Bastart et al. |
| 5,700,848 A | 12/1997 | Soon-Shiong et al. |
| 5,714,512 A | 2/1998 | Bastart et al. |
| 5,716,594 A | 2/1998 | Elmaleh et al. |
| 5,728,804 A | 3/1998 | Sharma et al. |
| 5,750,561 A | 5/1998 | Bastart et al. |
| 5,820,847 A | 10/1998 | Low et al. |
| 5,840,485 A | 11/1998 | Lebl et al. |
| 5,847,170 A | 12/1998 | Bouchard et al. |
| 5,855,900 A | 1/1999 | Nobuhiko |
| 5,880,154 A | 3/1999 | Boukrinskaia et al. |
| 5,917,016 A | 6/1999 | Holmes |
| 5,985,916 A | 11/1999 | Duncan et al. |
| 5,990,237 A | 11/1999 | Bentley et al. |
| 6,033,486 A | 3/2000 | Andros |
| 6,048,736 A | 4/2000 | Kosak |
| 6,060,597 A | 5/2000 | Tobe et al. |
| 6,068,831 A | 5/2000 | Platzek et al. |
| 6,096,331 A | 8/2000 | Desai et al. |
| 6,124,273 A | 9/2000 | Drohan et al. |
| 6,132,734 A | 10/2000 | Thomas et al. |
| 6,207,195 B1 | 3/2001 | Walsh et al. |
| 6,309,633 B1 | 10/2001 | Ekwuribe et al. |
| 6,331,635 B1 | 12/2001 | Bouchard et al. |
| 6,353,055 B1 | 3/2002 | Kabanov et al. |
| 6,372,780 B2 | 4/2002 | Bouchard et al. |
| 6,387,946 B1 | 5/2002 | Bouchard et al. |
| 6,410,342 B1 | 6/2002 | Affleck et al. |
| 6,420,176 B1 | 7/2002 | Lisziewicz et al. |
| 6,426,184 B1 | 7/2002 | Gao et al. |
| 6,495,579 B1 | 12/2002 | Hunter |
| 6,506,405 B1 | 1/2003 | Desai et al. |
| 6,509,323 B1 | 1/2003 | Davis et al. |
| 6,515,017 B1 | 2/2003 | Li et al. |
| 6,527,887 B1 | 3/2003 | Ruebner et al. |
| 6,537,579 B1 | 3/2003 | Desai et al. |
| 6,548,476 B1 | 4/2003 | Wu et al. |
| 6,589,736 B1 | 7/2003 | Rothschild et al. |
| 6,602,707 B2 | 8/2003 | Hefeneider et al. |
| 6,630,124 B1 | 10/2003 | Gozes et al. |
| 6,656,966 B2 | 12/2003 | Garvey et al. |
| 6,660,804 B1 | 12/2003 | Weltrowski et al. |
| 6,667,293 B1 | 12/2003 | Zhao et al. |
| 6,730,699 B2 | 5/2004 | Li et al. |
| 6,740,643 B2 | 5/2004 | Wolff et al. |
| 6,749,868 B1 | 6/2004 | Desai et al. |
| 6,753,006 B1 | 6/2004 | Desai et al. |
| 6,828,392 B2 | 12/2004 | Meldal et al. |
| 6,835,718 B2 | 12/2004 | Kosak |
| 6,849,462 B1 | 2/2005 | Winkler et al. |
| 6,884,789 B2 | 4/2005 | Davis et al. |
| 7,018,609 B2 | 3/2006 | Hwang Pun et al. |
| 7,091,192 B1 | 8/2006 | Davis et al. |
| 7,091,193 B2 | 8/2006 | Sherrill et al. |
| 7,132,399 B2 | 11/2006 | Hefeneider et al. |
| 7,141,540 B2 | 11/2006 | Wang et al. |
| 7,166,302 B2 | 1/2007 | Hwang Pun et al. |
| 7,241,907 B2 | 7/2007 | Didier et al. |
| 7,270,808 B2 | 9/2007 | Cheng et al. |
| 7,358,262 B2 | 4/2008 | Stockwell |
| 7,375,096 B1 | 5/2008 | Davis et al. |
| 7,427,605 B2 | 9/2008 | Davis et al. |
| 7,622,115 B2 | 11/2009 | Fyfe et al. |
| 7,776,814 B2 | 8/2010 | Domling et al. |
| RE41,884 E | 10/2010 | de Garavilla et al. |
| 7,807,198 B2 | 10/2010 | Pun et al. |
| 7,820,788 B2 | 10/2010 | Desai et al. |
| 7,923,536 B2 | 4/2011 | Desai et al. |
| 8,110,179 B2 | 2/2012 | Cheng et al. |
| 8,252,276 B2 | 8/2012 | Cheng et al. |
| 8,347,230 B2 | 1/2013 | Decker et al. |
| 8,357,377 B2 | 1/2013 | Pun et al. |
| 8,389,499 B2 | 3/2013 | Cheng et al. |
| 8,399,431 B2 | 3/2013 | Cheng et al. |
| 8,404,662 B2 | 3/2013 | Cheng et al. |
| 8,475,781 B2 | 7/2013 | Cheng et al. |
| 8,497,365 B2 | 7/2013 | Davis et al. |
| 8,580,242 B2 | 11/2013 | Cheng et al. |
| 8,580,243 B2 | 11/2013 | Cheng et al. |
| 8,680,202 B2 | 3/2014 | Cheng et al. |
| 9,550,860 B2 | 1/2017 | Cheng et al. |
| 2001/0024829 A1 | 9/2001 | Wolff et al. |
| 2001/0034333 A1 | 10/2001 | Kosak |
| 2001/0041706 A1 | 11/2001 | Synold et al. |
| 2001/0044412 A1 | 11/2001 | Wolff et al. |
| 2002/0032161 A1 | 3/2002 | Ringshaw et al. |
| 2002/0107372 A1 | 8/2002 | Hefeneider et al. |
| 2002/0111362 A1 | 8/2002 | Rubinfeld |
| 2002/0151523 A1 | 10/2002 | Davis et al. |
| 2003/0008818 A1 | 1/2003 | Pun et al. |
| 2003/0017972 A1 | 1/2003 | Pun et al. |
| 2003/0049203 A1 | 3/2003 | Elmaleh et al. |
| 2003/0129262 A1 | 7/2003 | Epner et al. |
| 2003/0144222 A1 | 7/2003 | Wang et al. |
| 2003/0157030 A1 | 8/2003 | Davis et al. |
| 2003/0157523 A1 | 8/2003 | Frantz et al. |
| 2004/0024032 A1 | 2/2004 | Voi et al. |
| 2004/0063654 A1 | 4/2004 | Davis et al. |
| 2004/0072799 A1 | 4/2004 | Li et al. |
| 2004/0077595 A1 | 4/2004 | Cheng et al. |
| 2004/0087024 A1 | 5/2004 | Bellocq et al. |
| 2004/0109888 A1 | 6/2004 | Pun et al. |
| 2004/0248842 A1 | 12/2004 | Wagner et al. |
| 2005/0042753 A1 | 2/2005 | Yang et al. |
| 2005/0186208 A1 | 8/2005 | Fyfe et al. |
| 2005/0272083 A1 | 12/2005 | Seshagiri |
| 2006/0025426 A1 | 2/2006 | Fraley |
| 2006/0121085 A1 | 6/2006 | Warren et al. |
| 2006/0182795 A1 | 8/2006 | Pun et al. |
| 2006/0188566 A1 | 8/2006 | Liversidge et al. |
| 2006/0210527 A1 | 9/2006 | Davis |
| 2006/0263434 A1 | 11/2006 | Desai et al. |
| 2006/0263435 A1 | 11/2006 | Davis et al. |
| 2006/0287220 A1 | 12/2006 | Li et al. |
| 2007/0025952 A1 | 2/2007 | Davis et al. |
| 2007/0025999 A1 | 2/2007 | Fyfe et al. |
| 2007/0031844 A1 | 2/2007 | Khvorova et al. |
| 2007/0036717 A1 | 2/2007 | Watanabe et al. |
| 2007/0036753 A1 | 2/2007 | Fyfe et al. |
| 2007/0036754 A1 | 2/2007 | Fyfe et al. |
| 2007/0036755 A1 | 2/2007 | Fyfe et al. |
| 2007/0036790 A1 | 2/2007 | Fyfe et al. |
| 2007/0071748 A1 | 3/2007 | Fyfe et al. |
| 2007/0071749 A1 | 3/2007 | Fyfe et al. |
| 2007/0128167 A1 | 6/2007 | Pun et al. |
| 2007/0148177 A1 | 6/2007 | Fyfe et al. |
| 2007/0148178 A1 | 6/2007 | Fyfe et al. |
| 2007/0238667 A1 | 10/2007 | Jia et al. |
| 2007/0258984 A1 | 11/2007 | Fyfe et al. |
| 2008/0058427 A1 | 3/2008 | Cheng et al. |
| 2008/0113031 A1 | 5/2008 | Moodley et al. |
| 2008/0145698 A1 | 6/2008 | Heil et al. |
| 2008/0146598 A1 | 6/2008 | Bianco |
| 2008/0160029 A1 | 7/2008 | Fyfe et al. |
| 2008/0171744 A1 | 7/2008 | Danter et al. |
| 2008/0176958 A1 | 7/2008 | Davis et al. |
| 2008/0193498 A1 | 8/2008 | Hausheer |
| 2008/0241148 A1 | 10/2008 | Fyfe et al. |
| 2008/0254100 A1 | 10/2008 | Lai et al. |

(56) References Cited

U.S. PATENT DOCUMENTS

| | | |
|---|---|---|
| 2008/0267968 A1 | 10/2008 | Fyfe et al. |
| 2008/0279954 A1 | 11/2008 | Davis et al. |
| 2008/0292630 A1 | 11/2008 | Fyfe et al. |
| 2008/0292631 A1 | 11/2008 | Fyfe et al. |
| 2009/0010881 A1 | 1/2009 | Fyfe et al. |
| 2009/0010883 A1 | 1/2009 | Fyfe et al. |
| 2009/0163574 A1 | 6/2009 | Kim et al. |
| 2009/0169638 A1 | 7/2009 | Davis et al. |
| 2009/0202989 A1 | 8/2009 | Hillan |
| 2009/0246173 A1 | 10/2009 | Fyfe et al. |
| 2009/0304798 A1 | 12/2009 | Davis et al. |
| 2010/0010071 A1 | 1/2010 | Davis et al. |
| 2010/0056488 A1 | 3/2010 | Teicher et al. |
| 2010/0056555 A1 | 3/2010 | Horak et al. |
| 2010/0112077 A1 | 5/2010 | Desai et al. |
| 2010/0160233 A1 | 6/2010 | Bissery et al. |
| 2010/0226880 A1 | 9/2010 | Fyfe et al. |
| 2010/0226987 A1 | 9/2010 | Gnaim et al. |
| 2010/0247668 A1 | 9/2010 | Eliasof et al. |
| 2011/0110852 A1 | 5/2011 | Miller et al. |
| 2011/0123494 A1 | 5/2011 | Fyfe et al. |
| 2011/0152512 A1 | 6/2011 | Ryan |
| 2011/0160159 A1 | 6/2011 | Ryan |
| 2011/0177161 A1 | 7/2011 | Nekkanti et al. |
| 2011/0178287 A1 | 7/2011 | Glucksmann et al. |
| 2011/0223241 A1 | 9/2011 | Tardi et al. |
| 2011/0237540 A1 | 9/2011 | Crawford et al. |
| 2011/0237748 A1 | 9/2011 | Podobinski et al. |
| 2011/0245201 A1 | 10/2011 | Ryan et al. |
| 2011/0300150 A1 | 12/2011 | Eliasof |
| 2012/0213854 A1 | 8/2012 | Fetzer |
| 2013/0028862 A1 | 1/2013 | Fyfe et al. |
| 2013/0029909 A1 | 1/2013 | Ryan |
| 2013/0164282 A1 | 6/2013 | Ryan |
| 2013/0209518 A1 | 8/2013 | Desai et al. |

FOREIGN PATENT DOCUMENTS

| | | |
|---|---|---|
| EP | 1534340 A2 | 6/2005 |
| EP | 2463289 A1 | 6/2012 |
| EP | 3049078 B1 | 6/2018 |
| FR | 2665169 A1 | 1/1992 |
| GB | 1390479 A | 4/1975 |
| GB | 2197720 A | 5/1988 |
| HU | 200913 B | 9/1990 |
| JP | 58113198 A | 7/1983 |
| JP | 58167613 A | 10/1983 |
| JP | 01-319502 | 12/1989 |
| JP | 02149513 A | 6/1990 |
| JP | 3221505 A | 9/1991 |
| JP | 4106101 A | 4/1992 |
| JP | 05331074 A | 12/1993 |
| JP | 7048451 A | 2/1995 |
| JP | 07316205 A | 12/1995 |
| JP | H9503493 A | 4/1997 |
| JP | 9263535 A | 10/1997 |
| JP | 10158195 A | 6/1998 |
| JP | 2001288097 A | 10/2001 |
| JP | 2006502301 A | 1/2006 |
| MX | 2012/005987 A | 6/2012 |
| RU | 2094059 C1 | 10/1997 |
| WO | 1990/02141 A1 | 3/1990 |
| WO | 1990/15070 A1 | 12/1990 |
| WO | 1991/013100 A1 | 9/1991 |
| WO | 1991/17300 A1 | 11/1991 |
| WO | 1992/10092 A1 | 6/1992 |
| WO | 1993/05084 A1 | 3/1993 |
| WO | 1993/024150 A1 | 12/1993 |
| WO | 1994/02518 A1 | 2/1994 |
| WO | 1994/09826 A2 | 5/1994 |
| WO | 1994/28031 A1 | 12/1994 |
| WO | 9503795 A1 | 2/1995 |
| WO | 1995/24221 A1 | 9/1995 |
| WO | 1995/32739 A1 | 12/1995 |
| WO | 1996/09073 A1 | 3/1996 |
| WO | 1996/031220 A1 | 10/1996 |
| WO | 1997/33044 A1 | 9/1997 |
| WO | 1997033552 A1 | 9/1997 |
| WO | 1997/36948 A1 | 10/1997 |
| WO | 98/03795 A1 | 1/1998 |
| WO | 1998/005689 A1 | 2/1998 |
| WO | 1998/020967 A1 | 5/1998 |
| WO | 1998/042382 A1 | 10/1998 |
| WO | 1998/047496 A2 | 10/1998 |
| WO | 1998/047536 A1 | 10/1998 |
| WO | 1998/049350 A1 | 11/1998 |
| WO | 1999/030727 A1 | 6/1999 |
| WO | 9930727 A1 | 6/1999 |
| WO | 1999/047172 A2 | 9/1999 |
| WO | 1999/061062 A1 | 12/1999 |
| WO | 1999/67296 A1 | 12/1999 |
| WO | 2000/01734 A1 | 1/2000 |
| WO | 2000/06117 A1 | 2/2000 |
| WO | 2000/09073 A2 | 2/2000 |
| WO | 2000/33885 A1 | 6/2000 |
| WO | 2000/038717 A2 | 7/2000 |
| WO | 2000/40962 A1 | 7/2000 |
| WO | 2000/66635 A1 | 11/2000 |
| WO | 2000/75162 A1 | 12/2000 |
| WO | 2000/75164 A1 | 12/2000 |
| WO | 2001/37665 A1 | 5/2001 |
| WO | 2001/66601 A1 | 9/2001 |
| WO | 01/74401 A2 | 10/2001 |
| WO | 200203850 A2 | 1/2002 |
| WO | 2002/049676 A2 | 6/2002 |
| WO | 2002/057424 A2 | 7/2002 |
| WO | 2002/083180 A1 | 10/2002 |
| WO | 2003044213 A2 | 5/2003 |
| WO | 2003/047518 A2 | 6/2003 |
| WO | 2003/052060 A2 | 6/2003 |
| WO | 03/079972 A2 | 10/2003 |
| WO | 2003079972 A3 | 10/2003 |
| WO | 2004/019993 A1 | 3/2004 |
| WO | 2004/022099 A2 | 3/2004 |
| WO | 2004/032862 A2 | 4/2004 |
| WO | 2004/033620 A2 | 4/2004 |
| WO | 2004/039869 A1 | 5/2004 |
| WO | 2004069159 A2 | 8/2004 |
| WO | 2005000900 A1 | 1/2005 |
| WO | 2006012527 A1 | 2/2006 |
| WO | 2006065780 A2 | 6/2006 |
| WO | 2006/089007 A2 | 8/2006 |
| WO | 2006/105361 A2 | 10/2006 |
| WO | 2008/076333 A2 | 6/2008 |
| WO | 2008148080 A2 | 12/2008 |
| WO | 2009024667 A2 | 2/2009 |
| WO | 2009079452 A2 | 6/2009 |
| WO | 2009/123764 A2 | 10/2009 |
| WO | 2010043050 A1 | 4/2010 |
| WO | 2011/031865 A1 | 3/2011 |
| WO | 2011034954 A1 | 3/2011 |
| WO | 2011063421 A1 | 5/2011 |
| WO | 2011089216 A1 | 7/2011 |
| WO | 2011146638 A1 | 11/2011 |
| WO | 2012125232 A1 | 9/2012 |
| WO | 2013037789 A1 | 3/2013 |
| WO | 2013059651 A1 | 4/2013 |
| WO | 2014/055913 A2 | 4/2014 |

OTHER PUBLICATIONS

"A Phase 2 Study of CRLX101 in Patients with Advanced Non-Small Cell Lung Cancer", Clinicaltrials.gov, updated Aug. 3, 2011, pp. 1-6.

"A Phase 2 Study of CRLX101 in Patients with Advanced Non-Small Cell Lung Cancer", Clinicaltrials.gov, updated Feb. 23, 2012, pp. 1-4.

"A Phase 2 Study of CRLX101 in Patients with Advanced Non-Small Cell Lung Cancer", Clinicaltrials.gov, updated Feb. 8, 2012, pp. 1-4.

"A Phase 2 Study of CRLX101 in Patients with Advanced Non-Small Cell Lung Cancer", Clinicaltrials.gov, updated Jun. 29, 2011, pp. 1-4.

(56) References Cited

OTHER PUBLICATIONS

"Adamantane," in The Merck Index, 11th ed., 1989, No. 140, pp. 24, Merck Research Laboratories.
"Amantadine," in The Merck Index, 11th ed., 1989, No. 380, pp. 60, Merck Research Laboratories.
"Arrowhead announces issuance of patent on subsidiary's key technology," Aug. 16, 2006, Press release.
"Arrowhead announces issuance of patent on subsidiary's key technology," May 8, 2007, Press Release.
"Arrowhead Research Subsidiary, Insert Therapeutics, receives FDA Approval for IT-101 Phase I Clinical," Mar. 14, 2006, Press release.
"Arrowhead Research Subsidiary, Insert Therapeutics, Treats first patient with nano-engineered anti-cancer therapeutic," Jul. 19, 2006, Business Wire.
"Arrowhead Subsidiaries, Insert and Calando, present data on Cyclosert(TM) drug delivery system at AACR meeting," Apr. 16, 2007, Press Release.
"Arrowhead Subsidiary Calando Pharmaceuticals enters into license agreement with Cerulean Pharma Inc.," Jun. 23, 2009, Press Release.
"Arrowhead Subsidiary, Insert Therapeutics, signs collaboration and option agreement for potent anticancer compound, tubulysin," Jan. 17, 2007, Press release.
"Arrowhead Subsidiary, Insert, publishes interim phase I data from human clinical trials for new cancer drug," Jun. 1, 2007, Press Release.
"Calando Pharmaceuticals announces completion of IT-101 Phase I clinical study," Oct. 23, 2008, Press Release.
"Calando Pharmaceuticals phase II clinical study opens to patient enrollment," Sep. 11, 2008, Press Release.
"Cerulean Pharma Inc. Presents Data on Nanopharmaceutical Development Candidates and Platform Technologies at American Chemical Society National Meeting & Exposition," Aug. 25, 2010, Press Release.
"Cerulean Pharma Inc. to Convene Nanomedicine Pioneers at 2010 American Chemical Society (ACS) National Meeting & Exposition in Boston," Aug. 19, 2010, Press Release.
"Efficacy Study of Maintenance IT-101 Therapy for Ovarian Cancer Patients," Updated Sep. 15, 2008, ClinicalTrials.gov.
"Efficacy Study of Maintenance IT-101 Therapy for Ovarian Cancer Patients," Updated Oct. 21, 2008, ClinicalTrials.gov.
"Efficacy Study of Maintenance IT-101 Therapy for Ovarian Cancer Patients," Updated Dec. 2, 2008, ClinicalTrials.gov.
"Efficacy Study of Maintenance IT-101 Therapy for Ovarian Cancer Patients," Updated Dec. 10, 2008, ClinicalTrials.gov.
"Efficacy Study of Maintenance IT-101 Therapy for Ovarian Cancer Patients," Updated Jan. 22, 2009, ClinicalTrials.gov.
"Efficacy Study of Maintenance IT-101 Therapy for Ovarian Cancer Patients," Updated Apr. 28, 2009, ClinicalTrials.gov.
"Efficacy Study of Maintenance IT-101 Therapy for Ovarian Cancer Patients," Updated Jun. 4, 2009, ClinicalTrials.gov.
"Efficacy Study of Maintenance IT-101 Therapy for Ovarian Cancer Patients," Updated Feb. 28, 2012 ClinicalTrials.gov.
"Efficacy Study of Maintenance IT-101 Therapy for Ovarian Cancer Patients," Updated Mar. 27, 2012, ClinicalTrials.gov.
"Insert Therapeutics describes in vivo performance and versatility of Drug Delivery platform," Jul. 22, 2003, Insert Therapeutics News Release.
"Insert Therapeutics describes in vivo performance and versatility of lead anticancer compound," Apr. 17, 2005, News Release.
"Insert Therapeutics files investigational new drug application for lead anti-cancer compound IT-101," Feb. 9, 2006, News Release.
"Insert Therapeutics presents capabilities and versatility of drug delivery platform," Sep. 9, 2003, Insert Therapeutics News Release.
"Insert Therapeutics signs new partnership with R&D Biopharmaceuticals for epothilones," Mar. 1, 2007, Press Release.
"Insert Therapeutics to initiate a multinational phase II clinical trial of lead drug candidate IT-101 in ovarian cancer," Apr. 17, 2008, Press Release.
"Insert Therapeutics, Inc. receives first patent on its Cyclosert(TM) polymer Technology," Feb. 4, 2003, Insert Therapeutics News Release.
"Insert Therapeutics, Inc. reports in vivo performance of Cyclosert(TM)—Camptothecin Anti-Cancer Formulation," Apr. 1, 2003, Insert Therapeutics News Release.
"Mark Davis Q&A—making it personal: finding a new way to treat cancer," Oct. 2007, Press release WNET (New York).
"Mark Davis to moderate 'novel approaches to drug delivery in cancer,'" Apr. 12, 2007, Press Release.
"Safety and Activity Study of CRLX101 in Patients With Advanced Non-Small Cell Lung Cancer", ClinicalTrials.gov, updated Jun. 24, 2011, pp. 1-4.
"Study of CRLX101 (Formerly named IT-101) in the Treatment of Advanced Solid Tumors", Updated Jul. 15, 2010, ClinicalTrials.gov.
"Study of CRLX101 (Formerly named IT-101) in the Treatment of Advanced Solid Tumors", Updated Jul. 29, 2010, ClinicalTrials.gov.
"Study of CRLX101 (Formerly named IT-101) in the Treatment of Advanced Solid Tumors", Updated Sep. 1, 2010, ClinicalTrials.gov.
"Study of CRLX101 (Formerly named IT-101) in the Treatment of Advanced Solid Tumors", Updated Sep. 23, 2010, ClinicalTrials.gov.
"Study of CRLX101 (Formerly named IT-101) in the Treatment of Advanced Solid Tumors", Updated Nov. 29, 2010, ClinicalTrials.gov.
"Study of CRLX101 (Formerly named IT-101) in the Treatment of Advanced Solid Tumors", Updated Jan. 20, 2011, ClinicalTrials.gov.
"Study of CRLX101 (Formerly named IT-101) in the Treatment of Advanced Solid Tumors", Updated May 13, 2011, ClinicalTrials.gov.
"Study of CRLX101 (Formerly named IT-101) in the Treatment of Advanced Solid Tumors", Updated Feb. 8, 2012, ClinicalTrials.gov.
"Study of IT-101 in the Treatment of Advanced Solid Tumors", Updated Jun. 2, 2006, ClinicalTrials.gov.
"Study of IT-101 in the Treatment of Advanced Solid Tumors", Updated Aug. 14, 2006, ClinicalTrials.gov.
"Study of IT-101 in the Treatment of Advanced Solid Tumors", Updated Aug. 24, 2006, ClinicalTrials.gov.
"Study of IT-101 in the Treatment of Advanced Solid Tumors", Updated Feb. 27, 2007, ClinicalTrials.gov.
Greenwald et al "Camptothecin-20-PEG Ester Transport Forms: the effect of Spacer Groups on Antitumor Activity" Bioorganic & Medicinal Chemistry, 1998, vol. 6, pp. 551-562.
Kiselyov et al, "VEGF/VEGFR signalling as a target for inhibiting angiogenesis" Expert Opin. Investig. Drugs, 2007, vol. 16, pp. 83-107.
The American Academy of Neurology (http://patients.aan.com/disorders/); accessed Apr. 16, 2018.
The American Academy of Neurology; Aicardi Syndrome (http://patients.aan.com/disorders/); accessed Apr. 16, 2018.
Crini et al. "Solid State NMR spectroscopy study of molecular motion in cyclomaltoheptaose (b-cyclodextrin) crosslinked with epichlorohydrin" Carbohydrate Research, 1998, vol. 308, pp. 37-45.
Renard et al. "Preparation and Characterization of Water Soluble High Molecular Weight b-Cyclodextrin-Epichlorohydrin Polymers" Eur. Polym. Journal, 1997, vol. 33, No. 1, pp. 49-57.
Extended European Search Report for European Application No. 17209803 dated May 15, 2018.
Intention to Grant from European Application No. EP 14849624.3 dated Jan. 18, 2018.
Communication Pursuant to Rules 70(2) and 70a(2) EPC from European Application No. EP 14849624.3 dated Apr. 28, 2017.
Decision to Grant from European Application No. EP 14849624.3 dated Jun. 1, 2018.
Chauhan et al "Normalization of tumour blood vessels improves the delivery of nanomedicines in a size-dependent manner" Nat Nanotechnol., 2012, 7(6), pp. 383-388.
Jain et al "Delivering Nanomedicine to Solid Tumors" Nat Rev Clin. Oncol., 2010, 7(11), pp. 653-664.

(56) References Cited

OTHER PUBLICATIONS

Pham et al, "Translational impact of nanoparticle-drug conjugate CRLX101 with or without Bevacizumab in advanced ovarian cancer" Clin Cancer Research, 2014, 21(4), pp. 808-818.
Weingart et al. "Local delivery of the topoisomerase I inhibitor camptothecin sodium prolongs survival in the rat intracranial 9L gliosarcoma model" Int. J. Cancer, vol. 62, 1995, pp. 605-609.
Ozeki et al. "Treatment of rat brain tumors using sustained-release of camptothecin from Poly(lactic-co-glycolic acid) microspheres in a thermoreversible hydrogel" Chem Pharm. Bull., vol. 58, No. 9, 2010, pp. 1142-1147.
Fleming et al. "In vitro cytotoxicity and in vivo distribution afer direct delivery of PEG-camptothecin conjugates to the rat brain" Bioconjugate Chem., vol. 15, 2004, pp. 1364-1375.
Hetman et al. "Neuroprotection by brain-derived neurotrophic factor is mediated by extracellular signal-regulated kinase and phosphatidylinositol 3-kinase" Journal of Biological Chemistry, vol. 274, No. 32, 1999, pp. 22569-22580.
Clinical Trial 2103, Study 4. Updated Jan. 20, 2011.
Clinical Trial 2103, Study 4. Updated Jan. 22, 2007.
Clinical Trial 2103, Study 4. Updated Jul. 17, 2006.
Clinical Trial 2103, Study 4. Updated Jul. 26, 2010.
Clinical Trial 2103, Study 4. Updated Jul. 6, 2007.
Clinical Trial 2103, Study 4. Updated Jun. 7, 2006.
Clinical Trial 2103, Study 4. Updated May 9, 2011.
Clinical Trial 2103, Study 4. Updated Oct. 18, 2011.
Clinical Trial 2103, Study 4. Updated Sep. 30, 2010.
Cram, "Cavitands: organic hosts with enforced cavities," Science, 1983, vol. 219, pp. 1177-1183.
Cram, "The design of molecular hosts, guests, and their complexes," Science, 1988, vol. 240, pp. 760-767.
Crini et al., "Linear cyclodextrin-poly (vinylamine): synthesis and NMR characterization," Euro. Polm. J., 1997, vol. 33, No. 7, pp. 1143-1151.
Cserhati, "Charge-transfer chromatographic study of the complex formation of some anticancer drugs with g-cyclodextrin," Analytical Biochemistry, 1995, vol. 225, pp. 328-332.
Cucinotta et al. "Synthesis and conformation of dihistamine derivatives of cyclomaltoheptaose (?-cyclodextrin)" Carbohydrate Research, vol. 224, pp. 95-102 (1992).
Cyclodextrin-Based Polymer-Camptothecin CRLX101 (Code C62600). NCI Thesaurus, Sep. 27, 2010; retrieved from the internet Oct. 26, 2011.
Danysz et al., "Aminoadamantanes as NMDA receptor antagonists and antiparkinsonian agents—preclinical studies," Neurosci. Biobehav. Rev., 1997, vol. 21, No. 4, pp. 455-468.
David et al., "Synthesis of hydrophobically end-capped poly(ethylene glycol)s with UV absorbing properties," Macromol. Rapid Commun., 2000, vol. 21, No. 14, pp. 990-993.
Davis et al., "Nanoparticle therapeutics: An emerging treatment modality for cancer," Nature Reviews, Drug Discovery, Sep. 2008, vol. 7, No. 9, pp. 771-782.
Davis et al., "Cyclodextrin-based pharmaceutics: past, present and future," Nature Reviews Drug Discovery, Dec. 1, 2004, vol. 3, No. 12, pp. 1023-1035.
Davis et al., "Cyclodextrin-containing polymers for drug delivery," PharmTech, 2001, vol. 2-5, pp. 185-188.
Davis et al., "Design and development of IT-101, a cyclodextrin-containing polymer conjugate of camptothecin," Advanced Drug Delivery Reviews, May 2009, vol. 61, pp. 1189-1192.
Davis et al., "Linear, water-soluble, cyclodextrin-containing polymers for the delivery of broad ranging therapeutics," Jul. 1, 2003, 30th Annual Meeting of the CRS (Jul. 19-23, 2003), Glasgow, Scotland.
De Groot et al. "Elongated multiple electronic cascade and cyclization spacer systems in activatible anticancer prodrugs for enhanced drug release," Journal of Organic Chemistry, 2001, vol. 66, pp. 8815-8830.
Deratani et al. "Linear cyclodextrin-containing polyelectrolytes 1. Synthesis of poly(1-vinylimidazole)-supported b-cyclodextrin. Effect of pH and ionic strength on the solution behaviour," Macromol. Chem. Phys., 1995, vol. 196, pp. 343-352.
Doukas et al. "Matrix immobilization enhances the tissue repair activity of growth factor gene therapy vectors" Human Gene Therapy, vol. 12, No. 7, pp. 783-798 (2001).
Du et al., "Steric considerations in supramolecular inclusion of modified β-cyclodextrins with triton X-100 and a-bromonaphthalene," Supramolecular Chem., 2005, vol. 7, pp. 209-214.
Ebright et al., "Incorporation of an EDTA-metal complex at a rationally selected site within a protein: application to EDTA-iron DNA affinity cleaving with catabolite gene activator protein (CAP) and Cro," Biochemistry, 1992, vol. 31, pp. 10664-10670.
Eliasof et al., "Rationale for design and early clinical development of IT-101," May 26, 2010, 8th International Symposium on Polymer Therapeutics: From Laboratory to Clinical Practice (May 24-26, 2010) Valencia, Spain.
Epa et al., "Downregulation of the p75 neurotrophin receptor in tissue culture and in vivo, using β-cyclodextrin-adamantane-oligonucleotide conjugates," Antisense & Nucleic Acid Drug Development, 2000, vol. 10, pp. 469-478.
Esteva et al., "Phase II study of Weekly Docetaxel and Trastuzumab for Patients with HER-2-Overexpressing Metastatic Breast Cancer" Journal of Clinical Oncology, vol. 20., No. 7, pp. 1800-1808 (2002).
European Search Report for Application No. 07 853 378.3 dated Apr. 16, 2013.
European Search Report for Application No. 10 817 784.1 dated Apr. 17, 2013.
European Search Report for European Application No. 06735216.1 dated Jun. 4, 2008.
European Search Report for European Application No. 13743255 dated Jun. 8, 2015.
European Search Report from EP Application No. 03786526.8 dated Sep. 3, 2010.
European Search Report from European Application Serial No. 03770286.7 dated Feb. 12, 2007.
Extended European Search Report for European Application No. 10832380.9 dated Jun. 22, 2015.
Extended European Search Report for European Application No. 12757511.6 dated Jul. 4, 2014.
Extended European Search Report from European Application Serial No. 10012442.9 dated May 7, 2012.
Extended European Search report from European Application Serial No. 10184884.4 dated Oct. 24, 2011.
Extended European Search Report from European Application Serial No. 10184901.6 dated Dec. 1, 2011.
Fang et al., "Recent Progress in Structure Activity Relationship and Mechanistic Studies of Taxol Analogues" Mini-Reviews in Medicinal Chemistry, vol. 5, pp. 1-12 (2005).
Ferlini et al., "New taxanes in development", Expert Opin. Investig. Drugs, vol. 17, No. 3, pp. 335-347 (2008).
Ferrari et al., "ExGen 500 is an efficient vector for gene delivery to lung epithelial cells in vitro and in vivo," Gene Therapy, 1997, vol. 4, pp. 1100-1106.
Fieser et al., "Reagents for organic synthesis," Wiley New York, 1967, vol. 3, pp. 265-266.
Finsinger et al., "Protective copolymers for nonviral gene vectors: synthesis, vector characterization and application in gene delivery," Gene Delivery, 2000, vol. 7, pp. 1183-1192.
Fisher, "A versatile system for receptor-mediated gene delivery permits increased entry of DNA into target cells, enhanced delivery to the nucleus and elevated rates of transgene expression," Gene Therapy, 2000, vol. 7, pp. 1337-1343.
Fitzpatrick et al. "The immunopharmacology of paclitaxel (Taxol), docetaxel (Taxotere), and related agents" International Immunopharmacology, 3 (2003) 1699-1714.
Floyd et al. "Hepatotoxicity of Chemotherapy" Seminars in Oncology (2006) vol. 33, pp. 50-67.
Fodor et al., "Light-directed, spatially addressable parallel chemical synthesis," Science, 1991, vol. 251, pp. 767-773.
International Search Report for International Application No. PCT/US2007/025551 dated Jan. 29, 2009.
International Search Report for International Application No. PCT/US2013/023601 dated Apr. 9, 2013.

(56) References Cited

OTHER PUBLICATIONS

International Search Report for International Application No. PCT/US2013/062832 dated Feb. 11, 2014.
International Search Report for PCT/US12/48865, dated Dec. 28, 2012.
International Search Report for PCT/US2011/23601 dated Apr. 9, 2013.
International Search Report for related Application No. PCT/US03/027588 dated Sep. 16, 2004.
International Search Report for related Application No. PCT/US03/31991 dated May 17, 2004.
International Search Report including Written Opinion for related Application No. PCT/US11/54025 dated Feb. 14, 2012.
Iser et al., "Chenodeoxycholic acid treatment of gallstones: A follow-up report and analysis of factors influencing response to therapy," N. Engl. J. Med., 1975 , vol. 293, No. 8, pp. 378-383 (abstract only).
Jensen, "Antitumor activity of IT-101, a cyclodextrin-containing polymer-camptothecin nanoparticle, in combination with various anticancer agents in human ovarian cancer xenografts," AACR Annual Meeting, Apr. 17, 2008,—Abstracts Online.
Jeong et al., "Novel intracellular delivery system of antisense oligonucleotide by self-assembled hybrid micelles composed of DNA/PEG conjugate and cationic fusogenic peptide," Bioconjugate Chem., 2003, vol. 14, pp. 473-479.
Jicsinszky et al., "Comprehensive supramolecular chemistry," 1996, vol. 3, No. 4, pp. 138-188, Szeitli et al., Eds., Pergamon.
Jones et al., "Releasable luciferin-transporter conjugates: tools for the real-time analysis of cellular uptake and release," J. Am Chem. Soc., 2006, vol. 128, pp. 6526-6527.
Jordan et al. "Microtubules as a Tareget for Anticancer Drugs" Nature Reviews Cancer (2004) vol. 4, pp. 253-265.
Kamruzzahan et al., "Antibody linking to atomic force microscope tips via disulfide bond formation," Bioconjugate Chem., 2006, vol. 17, pp. 1473-1481.
Kang et al., "Cyclodextrin complexation: influence on the solubility, stability, and cytotoxicity of camptothecin, an antineoplastic agent," European Journal of Pharmaceutical Sciences, 2002, vol. 15, pp. 163-170.
Karathanasis et al.,"Preparation of in vivo cleavable agglomerated liposomes suitable for modulated pulmonary drug delivery," Journal of Controlled Release, 2005, vol. 103, pp. 159-175.
Karunaratne et al., "Synthesis of bulky b-lactams for inhibition of cell surface b-lactamase activity," Bioconjugate Chem., 1993 , vol. 4, pp. 434-439.
Kelland "Discontinued drugs in 2005: oncology drugs" Exp. Opin. Investig. Drugs (2006) vol. 15, No. 11, pp. 1309-1318.
Keohavong et al. "Detection of K-ras mutations in lung carcinomas . . . " Clinical Cancer Research (1996) vol. 2, pp. 411-418.
Khan et al., "Methods for selective modifications of cyclodextrins", Chem. Rev. vol. 98, pp. 1977-1996 (1998).
Kim et al. "Update and Debate Issues in Surgical Treatment of Middle and Low Rectal Cancer" Journal of the Korean Society of Coloprotocology (2012) vol. 28, No. 5, pp. 230-241.
Kingston et al., "Tubulin-Interactive Natural Products as Anticancer Agents", J. Nat. Prod. vol. 72, pp. 507-515 (2009).
Klar et al. "Total Synthesis and Antitumor Activity of ZK-EPO: The First Fully Synthetic Epothilone in Clinical Development" Angew. Chem. Int. Ed. (2006) vol. 45, pp. 7942-7948.
Kneib-Cordonier et al., "Orthogonal solid-phase synthesis of human gastrin-I under mild conditions," Chem. Struc. and Biol., 1990, pp. 895-897, Rivier and Marshall, eds.
Kobayashi et al. "Systemic Lupus Erythematosus : Diagnosis and Fundamental Therapy" Journal of Pediatric Practice (2005) vol. 68, No. 4, pp. 643-650.
Koo et al; "Actively Targeted Low-Dose Camptothecin as a Safe, Long-Acting, Disease-Modifying Nanomedicine for Rheumatoid Arthritis" Pharm Res (2011) 28: pp. 776-787.

Kosmas et al "A phase I-II study of biweekly gemcitabine and irinotecan . . . " Cancer Chemother. Pharmacol. (2007) vol. 59, pp. 51-59.
Kummar et al. "Multihistology, Target-Driven Pilot Trian of Oral Topotecan as an Inhibitor of Hypoxia-Inducible Factor-1 a in Advanced Solid Tumors" Clinical Cancer Research (2011) 17 pp. 5123-5131.
La Mendola et al., "Copper(II) assisted self-assembly of functionalized beta-cyclodextrins with beta-alanyl-L-histidine" Journal of Supramolecular Chemistry, vol. 1, pp. 147-151 (2001).
Lam et al., "The one-bead-one compound combinatorial library method," Chem. Rev., 1997, vol. 97, pp. 411-448.
Lau et al. "Paclitaxel (Taxol): An Inhibitor of Angiogenesis in a Highly Vascularized Transgenic Breast Cancer" Cancer Biotherapy & Radiopharmaceuticals (1999) vol. 14, No. 1, pp. 31-36.
Lee et al., "Cucurbituril homologues and derivatives: new opportunities in supramolecular chemistry," Acc. Chem. Res., 2003, vol. 36, pp. 621-630.
Leonelli et al. "Design, synthesis and applications of hyaluronic acid-pacilitaxel bioconjugates" Molecules (2008) vol. 13, pp. 360-378.
Lewis, Hawley's Condensed Chemical Dictionary, John Wiley & Sons, Inc., 1987, pp. 311-312, New York, NY.
Li et al., "Molecular recognition by cyclodextrins (II) Inclusion of poly(ethylene glycol) by a-cyclodextrin," Polymer Preprints, 1991, vol. 40, No. 5-11, Abstract 4L 11 at p. E 1173, Japan (English Edition).
Li et al., "The complex formation between a-cyclodextrin and poly(ethylene glycol) and its stoichiometric discussion," Polymer Preprints, 1991, vol. 40, No. 1-4, Abstract 11-12-26 at p. E 400, Japan (English Edition).
Lin et al. "Phase II study of CT-2103 as first- or second-line chemotherapy in patients with metastatic breast cancer: unexpected incidence of hypersensitivity reactions". Invest. New Drugs (2007) 25:369-375.
Liu et al., "Sugar containing polyamines prepared using galactose oxidase coupled with chemical reduction," J. Am. Chem. Soc., 1999, vol. 121, pp. 466-467.
Lou et al. "Inhibition of Hypoxia-Inducible Factor-1a (HIF-1a) Protein Synthesis by DNA Damage Inducing Agents" PLoS One (2010) vol. 5, Issue 5.
Lowry O.H. et al., "Protein measurement with the folin phenol reagent," The Journal of Biological Chemistry, 1951, vol. 193, pp. 265-275.
Massarelli et al "KRAS mutation is an important predictor of resistance . . . " Clincial Cancer Research (2007) vol. 13, No. 10, pp. 2890-2896.
May et al., "Development of toxin-binding agent as a treatment for tunicaminyluracil toxicity: protection against tunicamycin poisoning of sheep," Australian Veterinary Journal, 1998, vol. 76, No. 11, pp. 752-756; chemical abstracts vol. 131, No. 3, pp. 193; Abstract No. 28805p (1999).
Mccray et al., "Properties and uses of photoreactive caged compounds," Annu. Rev. Biophys. Chem., 1989, vol. 18, pp. 239-270.
Mcgall et al., "Light-directed synthesis of high-density oligonucleotide arrays using semiconductor photoresists," Proc. Natl. Acad. Sci., 1996, vol. 93, pp. 13555-13560.
Mcgall et al., "The efficiency of light-directed synthesis of DNA arrays on glass substrates," J. Am. Chem. Soc., 1997, vol. 119, pp. 5081-5090.
Melton, L.D. et al., "Synthesis of monosubstituted cyclohexaamyloses," Carbohydrate Research, 1971, vol. 18, pp. 29-37.
Merritt et al. "Anti-angiogenic properties of metronomic topotecan in ovarian carcinoma" (2009) Cancer Biology & Therapy 8:16 1596-1603.
Middleton et al., "Synthetic biodegradable polymers as orthopedic devices," Biomaterials, 2000, vol. 21, pp. 2335-2346.
Minani et al, "Colon-specific drug delivery based on a cyclodextrin pro-drug: release behavior of biphenylylacetic acid from its cyclodextrin conjugates in rat intestinal tracts after oral administration," J. Pharm. Sci, 1998, vol. 87, No. 6, pp. 715-720.

(56) References Cited

OTHER PUBLICATIONS

Yurkovetskiy, et al. "MER-1001, a novel polymeric prodrug of camptothecin, is a potent inhibitor of LS174 and A2780 human tumor xenografts in a mouse model" Proc AACR (2007) abstract #781.

Zanta et al., "In vitro gene delivery to hepatocytes with galactosylated polyethylenimine," Bioconjugate Chem., 1997, vol. 8, pp. 839-844.

Zeidan et al., "A solvent-free method for isotopically or radioactively labeling cyclodextrins and cyclodextrin-containing polymers," Bioconjugate Chemistry, vol. 17, pp. 1624-1626 (available online Oct. 31, 2006).

Zhang et al., "Enthalpic domination of the chelate effect in cyclodextrin dimers," J. Am. Chem. Soc., 1993, vol. 115, pp. 9353-9354.

Zhang et al. "Microtubule-binding drugs offset tau sequestration by stabilizing microtubules and reversing fast axonal transport deficits in a tauopathy model" PNAS (2005) vol. 102, No. 1, pp. 227-231.

Zhang et al., "Ester hydrolysis by a catalytic cyclodextrin dimer enzyme mimic with a metallobipyridyl linking group," J. Am. Chem. Soc., 1997, vol. 119, pp. 1676-1681.

Zughul, M.B. et al., "Thermodynamics of propylparaben/β-cyclodextrin inclusion complexes," Pharm. Dev. Technol., 1998, vol. 3, pp. 43-53.

Ikeguchi M., et al. "Topoisomerase I Expression in Tumors as a Biological 1\'larker for CPT-11 Chc1noscnsitivity in Patients \-vith Colorectal Cancer," Surg Today (2011) 41:1196-1199.

Dufy MJ., et al. "A Personalized Approach to Cancer Treatment: How Biomarkers Can Help," Clinical Chemistry 54:11, 1770-1779 (2008).

Clinical trial NCT00381797, Sep. 2006.

World Heart Federation (http://www.world-heart-federation.org/cardiovascular-health/heart disease/different-heartdiseases/# c420 accessed Sep. 5, 2016).

Merck Manual (http://www.merckmanuals.com/professional/pediatrics/congenital cardiovascular-anomalies/overview-ofcongenital-cardiovascular-anomalies accessed Sep. 5, 2016).

The Merck Manual (http://www.merckmanuals.com/professional/cardiovascular-disorders/diseases-of-the-aorta-and-itsbranches/abdominal-aortic-aneurysms-aaa accessed Sep. 5, 2016).

(http://www. n h lbi. nih .gov/health/health-topics/topics/stroke/treatment. htm l accessed Sep. 5, 2016).

Hwang et al. ("a-Methylprednisone conjugated cyclodextrin polymer based nanoparticle for rheumatoid arthritis therapy"; Int. J.Nanomedicine; Sep. 2008; 3(3): 359-372).

Waksman et al. (Pharmacology in the Catheterization Laboratory; 2009).

Graboys et al. ("Nitroglycerin: The "mini" wonder drug"; Circulation; 2003).

Ma et al., Combination of antiangiogenesis with chemotherapy for more effective cancer treatment, Mol. Cancer Ther., 2008, 7('i 2), 3670-3684.

Valdivia, A. et al. "Improved pharmacological properties for superoxide dismutase modified with β-cyclodextrin-carboxymethylcellulose polymer." Biotechnology letters 28.18 (2006): 1465-1470.

Oliver et al., "A dose-finding pharmacokinetic study of IT-101, the first de novo designed nanoparticle therapeutic, in refractory solid tumors", Journal of Clinical Oncology, 2008, 26(15S), 14538.

Fujita et al., "Clinical approaches towards tumor angiogenesis: Past, present and future",Curr. Pharm. Des., 2008, 14(36}, 3820-3934.

Herbst, "Therapeutic options to target angiogenesis in human malignancies", Expert Opin. Emerg. Drugs, 2006, 11(4), 635-650.

Pourgholami et al., "Inhibitors of vascular endothelial growth factor in cancer", Cardiovasc. Hematolo. Agents Med Chem., 2008, 6(4), 343-347.

Liu et al. "Nano-sized assemblies of a PEG-Doceteaxel Conjugate as a formulation strategy for docetaxel," J. Pharm. Sci, 2008, vol. 97, No. 8, pp. 3274-3290.

Rapisarda et al. "Increased antitumor activity of bevacizumab in combination with hypoxia inducible factor-1 inhibition," Mol. Cancer Ther., 2009, vol. 8, No. 7, p. 1867-1877.

Schluep et al. "Preclinical efficacy of the camptothecin-polymer conjugate IT-101 in multiple cancer models," Clin. Cancer Res., 2006, vol. 12, No. 5, p. 1606-1614.

Rapisarda et al. "Antiangiogenic agents and HIF-1 inhibitors meet at the crossroads," Cell Cycle, 2009, vol. 8, No. 24, p. 4040-4043.

Lou et al. "Inhibition of hypoxia-inducible factor-1a (HIF-1a) protein synthesis by DNA damage inducing agents," PLoS One, 2010, vol. 5, No. 5, e10522.

"Assessment of tumor hypoxia," Cancer therapy & host, 2003, vol. 15, No. 3, p. 245-254.

Vecchio et al., "The synthesis and conformation of β-cyclodextrins functionalized with enantiomers of Boc-carnosine," Journal of Supramolecular Chemistry (2001) vol. 1, Issue 2, pp. 87-95.

Wen et al. "Prognostic significance of clinical and pathological stages on locally advanced rectal carcinoma after neoadjuvant chemoradiotherapy" Radiation Oncology, 2015; 10:124, pp. 1-9.

Extended European Search Report from Application No. 14849624.3 dated Apr. 10, 2017.

Hofheinz et al. "Phase I trial of capecitabine and weekly irinotecan in combination with radiotherapy for neoadjuvant therapy of rectal cancer," Journal of Clinical Oncology, 2005, vol. 23, No. 7, p. 1350-1357.

Klautke et al. "Concurrent chemoradiation with capecitabine and weekly irinotecan as preoperative treatment for rectal cancer: results from a phase I/II study," British Journal of Cancer, 2006, vol. 94, p. 976-980.

Weiss et al. "First-in-human phase 1/2a trial of CRLX101, a cyclodextrin-containing polymer-camptothecin nanopharmaceutical in patients with advanced solid tumor malignancies," Invest. New Drugs, 2013, vol. 31, p. 986-1000.

Fleischmann et al "Phase IIb Dose-Ranging Study of the Oral JAK Inhibitor Tofacitinib (CP-690,550) or Adalimumab Monotherapy Versus Placebo in Patients With Active Rheumatoid Arthritis With an Inadequate Response to Disease-Modifying Antirheumatic Drugs" Arthritis & Rheumatology, 2012, vol. 64 No. 3, pp. 617-629.

Yen et al "Phase 1 dose escalation, safety and pharmacokinetic study of IT-101 (CRLX101), a novel nanopharmaceutical containing camptothecin, in advanced solid tumor cancer patients" European Journal of Cancer, Supplement, 2010, vol. 8 No. 7, pp. 134-135.

Shabat et al., "Chemical adaptor systems," Chemistry—A European Journal., 2004, vol. 10, pp. 2626-2634.

Shabat et al., "In vivo activity in a catalytic antibody-prodrug system: Antibody catalyzed etoposide prodrug activation for selective chemotherapy," PNAS, Jun. 19, 2001, vol. 98, No. 13, pp. 7528-7533.

Smith et al., "Spectral characterization of β-cyclodextrin: triton X-100 complexes," J. Include. Phen. and Mol. Rec. Chem., 1991, vol. 10, pp. 471-484.

Smith, "Sweet revenge," Engineering & Science Caltech monthly newsletter, Mar. 2007, LXX, 1.

Song et al., "Catalyzed hydrolysis of RNA by metallic complexes of β-cyclodextrin derivative," Journal of Molecular Catalysis (China), 2001, vol. 15, No. 2, pp. 139-142.

Sonpavde et al. "Pazopanib, a potent orally administered small-molecule multitargeted typsine kinase inhibitor for renal cell carcinoma" Investig. Drugs (2008) 17(2): 253-261.

Su-Hua et al. "Neuroprotection of paclitaxel against cerebral ischemia/reperfusion-induced brain injury through JNK3 signaling pathway" Journal of Receptors and Signal Transduction (2001) vol. 31, No. 6, pp. 402-407.

Suh et al., "A new backbone of artificial enzymes obtained by cross-linkage of Poly(ethylenimine)," Bioorg. Med. Chem. Lett., 1998, vol. 8, pp. 1327-1330.

Supplemental Partial European Search Report for European Application No. EP13743255 dated Jun. 8, 2015.

Supplementary Partial European Search Report for European Application No. EP 13743111.0 dated May 21, 2015.

Svenson et al., "Polymeric nanoparticles of camptothecin—early clinical development of IT-101," May 22, 2010, Particles 2010, (May 22-25, 2010) Lake Buena Vista, FL.

Svenson et al.,"Preclinical to clinical development of the novel camptothecin nanopharmaceutical CRLX101 (formerly IT-101),"

(56) References Cited

OTHER PUBLICATIONS

Oct. 3, 2010, 8th International Nanomedicine and Drug Delivery Symposium (Oct. 3-5, 2010), Omaha, NE.
Szente et al., "Highly soluble cyclodextrin derivatives: chemistry, properties, and trends in development," Adv. Drug. Deliv. Rev., 1999, pp. 3617-3628.
Tabushi et al., "Artificial receptor recognizing hydrophobic carbonyl compounds," Journal of Organic Chemistry, 1986, vol. 51, No. 10, pp. 1918-1921.
Tabushi et al., "Bis(histamino)cyclodextrin-Zn-imidazole complex as an artificial carbonic anhydrase," J. Am. Chem. Soc., 1984, vol. 106, pp. 4580-4584.
Tabushi et al., "Characterization of regiospecific A,C- and A,D-disulfonate capping of β-cyclodextrin. Capping as an efficient production technique," J. Am. Chem. Soc., 1984, vol. 106, pp. 5267-5270.
Tabushi et al., "Specific bifunctionalization on cyclodextrin," Tetrahedron Lett., 1977, vol. 18, pp. 1527-1530.
Tamura et al. "Energy Transfer and Guest Responsive Fluorescence Spectra of Polyrotaxane Consisting of a-Cyclodextrins Bearing Naphthyl Moieties" The Chemical Society of Japan (2000), 73, pp. 147-154.
Tanaka et al., "Synthesis of doxorubicin-cyclodextrin conjugates," Journal of Antibiotics, 1994, vol. 47, No. 9, pp. 1025-1029.
Teague, S.J., "Facile synthesis of a o-nitrobenzyl photolabile linker for combinatorial chemistry," Tetrahedron Lett., 1996, vol. 37, pp. 5751-5754.
Teneriello et al. "Phase II Evaluation of Nanoparticle Albumin-Bound Paclitaxel in Platinum-Sensitive Patients With Recurrent Ovarian, Peritoneal, or Fallopian Tube Cancer" Journal of Clinical Oncology (2009) vol. 27, No. 9, pp. 1426-1431.
Tenjarla, S. et al., "Preparation, characterization, and evaluation of miconazole-cyclodextrin complexes for improved oral and topical delivery," Journal of Pharmaceutical Sciences, 1998, vol. 87, pp. 425-429.
Tijerina Monical et al., "Mechanisms of cytotoxicity in human ovarian carcinoma cells exposed to free Mce6 or HPMA copolymer-Mce6 conjugates," Photochemistry and Photobiology, 2003, vol. 77, No. 6, pp. 645-652.
Tojima et al., "Preparation of an a-cyclodextrin-linked chitosan derivative via reductive amination strategy," J. Polym. Sci., Part A: Polym. Chem., 1998, vol. 36, pp. 1965-1968.
Torchilin et al., "TAT peptide on the surface of liposomes affords their efficient intracellular delivery even at low temperature and in the presence of ametabolic inhibitors," PNAS, 2001, vol. 98, No. 15, pp. 8786-8791.
Trubetskoy, V. S., et al., "Self assembly of DNA-polymer complexes using template polymerization," Nucleic Acids Research, 1998, vol. 26, No. 18, pp. 4178-4185.
Trushina et al. "Microtubule destabilization and nuclear entry are sequential steps leading to toxicity in Huntington's disease" PNAS (2003) vol. 100, No. 21, pp. 12171-12176.
Uekama et al., "Cyclodextrin drug carrier systems," Chem. Rev., 1998, vol. 98, pp. 2045-2076.
Uekama et al., "Improvement of dissolution and absorption characteristics on phenytoin by a water-soluble b-cyclodextrin-epichlorohydrin polymer," Int. J. Pharm., 1985, vol. 23, pp. 35-42.
Valdivia et al. "Improved pharmacological properties for superoxide dismutase modified with B-cyclodextrin-carboxymethylcellulose polymer" Biotechnology Letters (2006) vol. 28, pp. 1465-1470.
Vicent et al. "Polymer conjugates as therapeuitcs . . . " Exp. Opin. Drug Deliv. (2008) vol. 5, No. 5, pp. 593-614.
Volk et al. "Nab-paclitaxel Efficacy in the Orthotopic Model of Human Breast Cancer is Significantly Enhanced by Concurrent Anti-Vascular Endothelial Growth Factor A Therapy" Neoplasia (2008) vol. 10, No. 6, pp. 613-623.
Vrueh De R L A et al., "Synthesis of a lipophilic prodrug of 9-(2-phosphonylmethoxyethyl ) Ade Nine (PMEA) and its incorporation into a hepatocyte-specific lipidic carrier," Pharmaceutical Research, 1999, vol. 16, No. 8, pp. 1179-1185.

Wang et al. "Paclitaxel at ultra low concentrations inhibits angiogenesis without affecting cellular microtubule assembly" Anti-Cancer Drugs (2003) vol. 14, pp. 13-19.
Warmuth, R. et al., "Recent highlights in hemicarcerand chemistry," Acc. Chem. Res., 2001, vol. 34, pp. 95-105.
Weickenmeier et al., "Cyclodextrin sidechain polyesters—synthesis and inclusion of adamantane derivatives," Macromol. Rapid Commun., 1996, vol. 17, pp. 731-736.
Wenz et al., "Threading cyclodextrin rings on polymer chains," Angewandte Chemie, International Edition, 1992, vol. 31, No. 2, pp. 197-199.
Whitehead, R. et al "A phase II trail of epothilone B analogue BMS-247550 (NSC #710428) ixabepilone, in patients with advanced pancreas cancer: A Southwest Oncology Group Study" Invest New Drugs (2006) vol. 24, pp. 515-520.
Williams D.F., "Biodegradation of surgical polymers," J. Mater. Sci., 1982, pp. 1233-1246.
Wolfgang et al., "Rationale for design and early clinical development of IT-101, a cyclodextrin-polyethylene-glycol copolymer nanoparticle delivery of camptothecin," Jul. 2010, 2010 ACS National Meeting (Aug. 22-26, 2010), Boston, MA.
Yan et al. "Combination with SN-38 on human colon cancer LoVo cells" Database Accession No. NLM20021826; Database Medline [Online] US National Library of Medicine (NLM); Oct. 2009.
Yano et al., "Colon-specific delivery of prednisolone-appended a-cyclodextrin conjugate; alleviation of systemic side effect after oral administration," Journal of Controlled Release, 2002, vol. 79, No. 1-3, pp. 103-112, Elsevier Science Publishers B.V., Amsterdam, NL.
Yano et al., "Prednisolone-appended a-cyclodextrin: alleviation of systemic adverse effect of prednisolone after intracolonic administration in 2,4,6-trinitrobenzenesulfonic acid-induced colitis rats," Journal of Pharmaceutical Sciences, 2001, vol. 90, No. 12, pp. 2103-2112.
Yano et al., "Preparation of prednisolone-appended a-, b-, and g-cyclodextrins: substitution at secondary hydroxyl groups and in vitro hydrolysis behavior," J. Pharm. Sci., 2001, vol. 4, pp. 493-503.
Yen et al., "First-in-human phase I trial of a cyclodextrin-containing polymer-camptothecin nanoparticle in patients with solid tumors", American Society of Clinical Oncology, 2007 annual meeting (Jun. 1-5, 2007) Chicago, IL.
Yen et al., "Phase 1 dose escalation, safety and pharmacokinetic study of IT-101 (CRLX101), a novel nanopharmaceutical containing camptothecin, in advanced solid tumor cancer patients," Nov. 16, 2010, EORTC-NCI-AACR International Symposium on Molecular Targets and Cancer Therapeutics, Abstract 423, (Nov. 16-19, 2010) Berlin, Germany.
Yen et al., "Toxicokinetic and pharmacokinetic study of IT-101 in humans with refractory solid tumors," Apr. 21, 2009, AACR Annual Meeting (Apr. 18-22, 2009), Denver, CO.
Yoo et al., "Synthesis of oligonucleotides containing 3'-alkyl carboxylic acids using universal, photolabile solid phase synthesis supports," J. Org. Chem., 1995, vol. 60, pp. 3358-3364.
Young et al "CRLX101 (formerly IT-101)—A Novel Nanopharmaceutical of Camtothecin in Clinical Development" Current Bioactive Compounds 2011 vol. 7, pp. 8-14.
Young et al., "CRLX101 (formerly IT-101)—A novel nanopharmaceutical in phase 1b/2a clinical development," Current Bioactive Compounds, Fall 2010.
Ruo et al., "Long-Term Prognostic Significance of Extent of Rectal Cancer Response to Preoperative, Radiation and Chemotherapy" Annals of Surgery, 2002, vol. 236 No. 1, pp. 75-81.
Smalley et al., "Phase III of Fluorouracil-Based Chemotheraphy Regimens Plus Radiotheraphy in Postoperative Adjuvant Rectal cancer: GI INT 0144" Journal of Clinical Oncology, 2006, vol. 24 No. 22.
Singer et al., "Water-soluble poly-(L-glutamic acid)-Gly-camptothecin conjugates enhance camptothecin stability and efficacy in vivo" Journal of Controlled Release, 2001, vol. 74, pp. 243-247.
Sudimack et al., "Targeted drug delivery via the folate receptor" Advanced Drug Delivery Reviews, 2000, vol. 41, pp. 147-162.
Clinical Trial 2013, Study 11. Updated Mar. 30, 2006.

(56) References Cited

OTHER PUBLICATIONS

Clinical Trial 2103 Study 11.
Clinical Trial 2103, Study 11. Updated Apr. 10, 2007.
Clinical Trial 2103, Study 11. Updated Apr. 11, 2006.
Clinical Trial 2103, Study 11. Updated Apr. 12, 2007.
Clinical Trial 2103, Study 11. Updated Apr. 18, 2007.
Clinical Trial 2103, Study 11. Updated Apr. 26, 2007.
Clinical Trial 2103, Study 11. Updated Aug. 14, 2006.
Clinical Trial 2103, Study 11. Updated Aug. 24, 2006.
Clinical Trial 2103, Study 11. Updated Aug. 29, 2006.
Clinical Trial 2103, Study 11. Updated Dec. 27, 2006.
Clinical Trial 2103, Study 11. Updated Dec. 27, 2007.
Clinical Trial 2103, Study 11. Updated Dec. 6, 2006.
Clinical Trial 2103, Study 11. Updated Feb. 11, 2006.
Clinical Trial 2103, Study 11. Updated Feb. 20, 2007.
Clinical Trial 2103, Study 11. Updated Feb. 23, 2006.
Clinical Trial 2103, Study 11. Updated Jan. 11, 2007.
Clinical Trial 2103, Study 11. Updated Jan. 19, 2007.
Clinical Trial 2103, Study 11. Updated Jan. 30, 2007.
Clinical Trial 2103, Study 11. Updated Jul. 13, 2006.
Clinical Trial 2103, Study 11. Updated Jul. 19, 2006.
Clinical Trial 2103, Study 11. Updated Jul. 26, 2006.
Clinical Trial 2103, Study 11. Updated Jul. 5, 2006.
Clinical Trial 2103, Study 11. Updated Jun. 13, 2006.
Clinical Trial 2103, Study 11. Updated Jun. 18, 2012.
Clinical Trial 2103, Study 11. Updated Jun. 22, 2006.
Clinical Trial 2103, Study 11. Updated Jun. 27, 2009.
Clinical Trial 2103, Study 11. Updated Jun. 9, 2006.
Clinical Trial 2103, Study 11. Updated Mar. 10, 2006.
Clinical Trial 2103, Study 11. Updated Mar. 13, 2007.
Clinical Trial 2103, Study 11. Updated Mar. 20, 2007.
Clinical Trial 2103, Study 11. Updated Mar. 27, 2007.
Clinical Trial 2103, Study 11. Updated Mar. 30, 2006.
Clinical Trial 2103, Study 11. Updated Mar. 7, 2007.
Clinical Trial 2103, Study 11. Updated May 10, 2006.
Clinical Trial 2103, Study 11. Updated May 26, 2008.
Clinical Trial 2103, Study 11. Updated May 3, 2006.
Clinical Trial 2103, Study 11. Updated May 30, 2006.
Clinical Trial 2103, Study 11. Updated May 5, 2007.
Clinical Trial 2103, Study 11. Updated Nov. 16, 2006.
Clinical Trial 2103, Study 11. Updated Nov. 21, 2006.
Clinical Trial 2103, Study 11. Updated Nov. 7, 2011.
Clinical Trial 2103, Study 11. Updated Nov. 9, 2006.
Clinical Trial 2103, Study 11. Updated Oct. 12, 2006.
Clinical Trial 2103, Study 11. Updated Oct. 18, 2006.
Clinical Trial 2103, Study 11. Updated Oct. 29, 2007.
Clinical Trial 2103, Study 11. Updated Sep. 13, 2006.
Clinical Trial 2103, Study 11. Updated Sep. 26, 2006.
Clinical Trial 2103, Study 4.
Clinical Trial 2103, Study 4. Updated Jan. 17, 2008.
Mizobe et al. "Efficacy of the combined use of bevacizumab and irinotecan as a postoperative adjuvant chemotherapy in colon carcinoma" Oncology Reports (2008) vol. 20, pp. 517-523.
Morii et al. "Cooperative Oligomerization Enhances Sequence-Selective DNA Binding by a Short Peptide" Journal of the American Chemical Society, vol. 118, No. 42, Oct. 23, 1996.
Muallaoglu et al. "Acute transient encephalopathy after weekly paclitaxel infusion" Med Oncol (2012) vol. 29, pp. 1297-1299.
Mungall et al., "Use of the azido group in the synthesis of 5' terminal aminodeoxythymidine oligonucleotides," J. Org. Chem., 1975, vol. 40, No. 11, pp. 1659-1662.
Nande et al., "In vitro and in vivo toxicity testing for the prolonged local delivery of a cyclosert-camptothecin polymer conjugate in a model of intracranial glioma," 74th Annual American Association of Neurological Surgeons (Apr. 22-27, 2006) San Francisco, CA.
Numbenjapon et al., "Preclinical efficacy of camptothecin polymer conjugate (IT-101) in human burkitt lymphoma bearing mice," Dec. 2006, 2006 ASH Annual Meeting (Dec. 9-12, 2006) Washington, DC.

Numbenjapon, T MD et al., "Preclinical results of the camptothecin-polymer conjugate IT-101 in multiple human lymphoma xenografts," Blood (Ash Annual Meeting Abstracts), Dec. 2007, 110:Abstract 1376.
Numbenjapon, T MD, et al., "Preclinical results of camptothecin-polymer conjugate (IT-101) in multiple human lymphoma xenograft models," Clinical Cancer Research, 2009, vol. 15, pp. 4365-4373 (available online Jun. 23, 2009).
O'Shaughnessy et al., "Randomized, open-label, phase II trail of oral capecitabine (Xeloda®) vs. a reference arm of intravenous CMF (cyclophosphamide, methotrexate and 5-fluorouracil) as first-line thearpy for advanced/metastatic breat cancer" Annals of Oncology, vol. 12, pp. 1247-1254 (2001).
Oliver, J.C. et al., "A dose finding pharmacokinetic study of IT-101, the first de novo designed nanoparticle therapeutic, in refractory solid tumors," American Society of Clinical Oncology, 2008 Annual Meeting (May 30-Jun. 3, 2008) Chicago, IL.
Ooya et al., "Synthesis and characterization of an oligopeptide-terminated polyrotaxane as a drug carrier," Polym. Adv. Technol., 2000, vol. 11, pp. 642-651.
Ortega-Caballero et al., "Binding affinity properties of dendritic glycosides based on a b-cyclodextrin core toward guest molecules and concanavalin A," Journal of Organic Chemistry, 2001, vol. 66, No. 23, pp. 7786-7795.
Oudard et al. "Treatment options in renal cell carcinoma: past, present and future" Annals of Oncology 18 (Supplement 10) x25-x31, Sep. 2007.
Ozols, Robert. "Systemic Therapy for Ovarian Cancer: Current Status and New Treatments". Seminars in Oncology. 33(suppl 6): S3-S11 (2006).
Patchornik et al., "Photosensitive protecting groups," J. Am. Chem. Soc., 1970, vol. 92, pp. 6333-6335.
Phase II trial of paclitaxel polyglumex (PPX) with capecitabine (C) for metastatic breast cancer (MBC). American Society of Clinical Oncology; Journal of Clinical Oncology 26: 2008 (May 20 suppl; abstr 1063). Downloaded Sep. 13, 2012.
Pierce, 1989 Handbook and General Catalog, 1989, pp. 288-293, Rockford, IL.
Pillai et al., "Photoremovable protecting groups in organic synthesis," Synthesis, 1980, pp. 1-26.
Pirrung et al., "Comparison of methods for photochemical phosphoramidite-based DNA synthesis," J. Org. Chem., 1995, vol. 60, pp. 6270-6276.
Pizzolato et al. "The camptothecins" The Lancet (2003) vol. 361 pp. 2235-2242.
Pulfer et al., "Incorporation of nitric oxide-releasing crosslinked polyethyleneimine microspheres into vascular grafts," J. Biomed. Mat. Res., 1997, vol. 37, No. 2, pp. 182-189.
Pun et al., "Cyclodextrin-modified polyethylenimine polymers for gene delivery," Bioconjugate Chem., 2004, vol. 15, pp. 831-840 (available online Jun. 29, 2004).
Pun et al., "Development of a nonviral gene delivery vehicle for systemic application," Bioconjugate Chemistry, vol. 13, pp. 630-639.
Puppo et al. "Topotecan inhibits vascular endothelial growth factor production and angiogenic activity induced by hypoxia in human neuroblastoma by targeting hypoxia-inducible factor-1 a and -2a" Molecular Cancer Therapeutics (2008), pp. 1974-1984.
Putnam et al., "Tissue engineering using synthetic extracellular matrices," Nature Med., 1996, vol. 2, pp. 824-826.
Ramaswamy et al., "Phase II Trail of Bevacizumab in Combination with Weekly Docetaxel in Metastatic Breast Cancer Patients" Clin. Cancer Research, vol. 12, No. 10, pp. 3124-3129 (2006).
Rapisarda et al. "Identification of Small Molecule Inhibitors of Hypoxia-inducible Factor 1 Transcriptional Activation Pathway" Cancer Research (2002) 62 pp. 4316-4324.
Rapisarda et al. "Increased antitumor activity of bevacizumab in combination with hypoxia inducible factor-1 inhibition" Molecular Cancer Therapeutics (2009) 8 1867-1877.
Rapisarda et al. "Schedule-dependent Inhibition of Hypoxia-inducible Factor-1a Protein Accumulation, Angiogenisis, and Tumor Growth by Topotecan in U251-HRE Glioblastoma Xenografts" Cancer Research (2004) 64, pp. 6845-6848.

(56) References Cited

OTHER PUBLICATIONS

Rapisarda et al. "Topoisomerase I-Mediated Inhibition of Hypoxia-Inducible Factor 1: Mechanism and Therapeutic Implications" Cancer Research (2004) 64, pp. 1475-1482.
Redenti et al., "Cyclodextrins in Oligonucleotide Delivery", Advanced Drug Delivery Reviews, vol. 53, No. 2 pp. 235-244 (2001).
Reineke et al., "Structural effects of carbohydrate-containing polycations on gene delivery. 1. Carbohydrate size and its distance from charge centers," Bioconjugate Chemistry, 2003, vol. 14, No. 1, pp. 247-254.
Reineke et al., "Structural effects of carbohydrate-containing polycations on gene delivery. 2. Charge center type," Bioconjugate Chemistry, 2003, vol. 14, No. 1, pp. 255-261.
Rejmanova et al., "Polymers containing enzymatically degradeable bonds," Macromol. Chem., 1983, vol. 184, pp. 2009-2020.
Rekhtman et al. "Clarifying the spectrum of driver oncogene mutations . . . " Clin. Cancer Research (2012) vol. 18, No. 4, pp. 1167-1176.
Rice et al. "Overcoming the Blood-Brain to Taxane Delivery for Neurodegenerative Diseases and Brain Tumors" Journal of Molecular Neuroscience (2003) vol. 20, pp. 339-343.
Rich et al., "Preparation of a new o-nitrobenzyl resin for solid-phase synthesis of tert-butyloxycarbonyl-protected peptide acids," J. Am. Chem. Soc., 1975, vol. 97, pp. 1575-1579.
Ross et al. "A Phase 2 Study of Carboplatin Plus Docetaxel in Men With Metastatic Hormone-refractory Prostate Cancer Who Are Refractory to Docetaxel" Cancer (2008) vol. 112, No. 3, pp. 521-526.
Saenger, "Structural aspects of cyclodextrins and their inclusion complexes," Inclusion Compounds, J. L. Atwood (ed.), 1984, vol. 2, No. 8, pp. 231-259 , Academic Press, New York, NY.
Saijo et al. "Advances in the treatment of non-small cell lung cancer" Cancer Treatment Rev. (2008) vol. 34, pp. 521-526.
Saijo et al. "Irinotecan combined with radition therapy . . . " Clinical Cancer Research (2002) vol. 4, suppl 1 pp. S21-S25.
Sandier et al., "Interaction between an adamantane end-capped poly(ethylene oxide) and a b-cyclodextrin polymer," American Cancer Society, 2000, vol. 16, pp. 1634-1642.
Schluep et al., "Pharmacokinetics and tumor dynamics of the nanoparticle IT-101 from PET imaging and tumor histological measurements," PNAS, vol. 106, No. 27, pp. 11394-11399 (available online Jun. 29, 2009).
Schluep et al., "Pharmacokinetics and biodistribution of the camptothecin-polymer conjugate IT-101 in rats and tumor bearing mice," Cancer Chemotherapy and Pharmacology, 2006, vol. 57, pp. 654-662 (available online Aug. 26, 2005).
Schluep et al., "Polymeric tubulysin-peptide nanoparticles with potent antitumor activity," Clin. Cancer Res., 2009, vol. 15, pp. 181-189 (available online Dec. 31, 2008).
Schluep et al., "Preclinical efficacy of the camptothecin-polymer conjugate IT-101 in multiple cancer models", Clin. Cancer Res., 2006, vol. 12, pp. 1606-1614.
Schluep, "Insert Therapeutics-product development update NSTI nanotech," Nanotech for Investors, May 21, 2007, Santa Clara, CA.
Schluep, et al., "Camptothecin-polymer conjugate shows improved biodistribution and preclinical efficacy in vivo," 2005 AACR Annual Meeting, (Apr. 16-20, 2005) Anaheim, CA.
Schluep,"Nanoparticulate chemotherapy with linear, cyclodextrin-containing polymers," May 15, 2006, XIII International Cyclodextrin Symposium, (May 14-17, 2006) Torino, Italy.
Sessa et al., "Phase 1 clinical study of the novel epothilone B analogue BMS-310705 given on a weekly schedule", Annals of Oncology, vol. 18: 1548-1553, 2007.
"Study of IT-101 in the Treatment of Advanced Solid Tumors", Updated Aug. 17, 2007, ClinicalTrials.gov.
"Study of IT-101 in the Treatment of Advanced Solid Tumors", Updated Nov. 1, 2007, ClinicalTrials.gov.
"Study of IT-101 in the Treatment of Advanced Solid Tumors", Updated Nov. 19, 2007, ClinicalTrials.gov.
"Study of IT-101 in the Treatment of Advanced Solid Tumors", Updated Jan. 4, 2008, ClinicalTrials.gov.
"Study of IT-101 in the Treatment of Advanced Solid Tumors", Updated Jul. 20, 2008, ClinicalTrials.gov.
"Study of IT-101 in the Treatment of Advanced Solid Tumors", Updated Aug. 24, 2009, ClinicalTrials.gov.
"Study of IT-101 in the Treatment of Advanced Solid Tumors", Updated Apr. 5, 2010, ClinicalTrials.gov.
Ackers, M. J. "Excipient-Drug Interactions in Parental Formulations" Journal of Pharmaceutical Sciences; Nov. 2002; vol. 91, No. 11 pp. 2283-2300.
Adlard et al. "The effects of taxol on the central nervous system response to physical injury" Acta Neuropathol (2000) vol. 100, pp. 183-188.
Aizawa et al. "Stability of the Dimerization Domain Effects the Cooperative DNA Binding of Short Peptides" Biochemistry 1999, 38, pp. 4008-4017.
Albers et al., "Cyclodextrin derivatives in pharmaceutics," Crit. Rev. Ther. Drug Carrier Syst., 1995, vol. 12, pp. 311-337.
Aldrich Catalog/Handbook of Fine Chemicals, 1994-1995, pp. 399, Aldrich Chemical Company, Inc., Milwaukee, WI.
Alexakis et al., "Microencapsulation of DNA within alginate microspheres and crosslinked chitosan membranes for in vivo application," Appl. Biochem. Biotechnol., 1995, vol. 50, pp. 93-106.
Alizadeh et al., "Tumor-associated macrophages are predominant carriers of cyclodextrin-based nanoparticles in gliomas," Nanomedicine: Nanotechnology, Biology, and Medicine, 2010, vol. 6, pp. 382-390 (published online Oct. 15, 2009).
Alvez et al. "Animal Models of Bone Loss in Inflammatory Arthritis: from Cytokines in the Bench to Novel Treatements for Bone Loss in the Bedside—a Comprehensive Review" Clinic. Rev. Allerg. Immunol. (2015) pp. 1-21.
Ambasta et al. "Nanoparticle mediated targeting of VEGFR and cancer stem cells for cancer therapy" Vascular Cell (2011) vol. 3, No. 26 pp. 1-8.
Amiel et al., "Association between amphiphilic poly(ethylene oxide) and β-cyclodextrin polymers: aggregation and phase separation," Advances in Colloid and Interface Science, 1999, vol. 79, pp. 105-122.
Amiel et al., "New associating polymer systems involving water soluble β-cyclodextrin polymers," Journal of Inclusion Phenomena and Molecular Recognition in Chemistry, 1996, vol. 25, pp. 61-67.
Amiel et al., "Associations between hydrophibically end-caped polyethylene oxide and water soluble b cyclodextrin polymers", Int. J. Polymer Analiysis & Characterization, 1:289-300 (1995).
Amit et al., "Photosensitive protecting groups of amino sugars and their use in glycoside synthesis. 2-nitrobenzyloxycarbonylamino and 6-nitroveratryloxycarbonylamino derivatives," J. Org. Chem., 1974, vol. 39, pp. 192-196.
Ashton et al., "Amino acid derivatives of b-cyclodextrin," Journal of Organic Chemistry, 1996, vol. 61, pp. 903-908.
Baldwin et al., "New photolabile phosphate protecting groups," Tetrahedron, 1990, vol. 46, pp. 6879-6884.
Baranello "DNA topoisomerase I inhibition by camptothecin iduces escape of RNA polymerase II from promoter-proximal pause site, antisense transcription and histone acetylation at the human HIF-1a gene locus" (2010) Nucleic Acids Research, vol. 38, No. 1, pp. 159-171.
Barany et al., "A three-dimensional orthogonal protection scheme for solid-phase peptide synthesis under mild conditions," J. Am. Chem. Soc., 1985, vol. 107, pp. 4936-4942.
Bellocq et al. "Transferrin-containing, cyclodextrin polymer-based particles for tumor-targeted gene delivery," Bioconjugate Chem., 2003, vol. 14, pp. 1122-1132 (available online Nov. 4, 2003).
Bellocq et al. "Transferrin-targeted, cyclodextrin polycation-based gene vector for systemic delivery," Molecular Therapy, May 2003, vol. 7, pp. S290.
Bellocq et al., "Synthetic biocompatible cyclodextrin-based constructs for local gene delivery to improve cutaneous wound healing," Bioconjugate Chem., 2004, vol. 15, pp. 1201-1211 (available online Oct. 26, 2004).
Bellof et al., "A new phenacyl-type handle for polymer supported peptide synthesis," Chimia, 1985, pp. 39317-39320.

(56) References Cited

OTHER PUBLICATIONS

Beppu et al, "Topotecan Blocks Hypoxia-Inducible Factor-1a and Vascular Endothelial Growth Factor Expression Induced by Insulin-Like Growth Factor-I in Neuroblastoma Cells" Cancer Research (2005) 65: (11) pp. 4775-4781.

Bissett, et al. "Phase 1 and pharmackinetic (PK) study of MAG-CPT (PNU 166148): a polymeric derivative of camptothecin (CPT)" British Journal of Cancer (2004) vol. 91, pp. 50-55.

Bolis et al. "Paclitaxel 175 or 225 mg per Meters Squared With Carboplatin in Advanced Ovarian Cancer: A Randomized Trial" Journal of Clinical Oncology. vol. 22, No. 4. (2004).

Boussif et al., "A versatile vector for gene and oligonucleotide transfer into cells in culture and in vivo: polyethylenimine," Proceedings of the National Academy of Sciences, 1995, vol. 92, No. 16, pp. 7297-7301.

Bouzin et al. "Targeting tumor stroma and exploiting mature tumor vasculature to improve anti-cancer drug delivery" Drug Resistance Updates (2007) vol. 10, pp. 109-120.

Boyette-Davis "Differential effects of paclitaxel treatment on cognitive functioning and mechanical sensitivity" Neurpscience Letters (2009) vol. 453, pp. 170-174.

Breslow et al., "Cholesterol Recognition and binding by cyclodextrin dimers," J. Am. Chem. Soc., 1996, vol. 118, pp. 8495-8496.

Breslow et al., "Biomimetic reactions catalyzed by cyclodextrins and their derivatives," Chemical Reviews, 1998, vol. 98, No. 5, pp. 1997-2011.

Breslow et al., "Molecular recognition by cyclodextrin dimers," Tetrahedron, 1995, vol. 51, No. 2, pp. 377-388.

Breslow, "Biomimetic chemistry and artificial enzymes: catalysis by design," Accounts of Chemical Research, 1995, vol. 28, No. 3, pp. 146-153.

Breslow, "Studies in biomimetic chemistry," Pure & Applied Chemistry, 1988, vol. 70, No. 2, pp. 267-270.

Cameron et al., "A phase III randomized comparison of lapatinib plus capecitabine versus capecitabine alone in women with advanced breast cancer that has progressed on trastuzumab: updated efficacy and biomarker analyses" Breast Cancer Res Treat vol. 112, pp. 533-543 (2008).

Cao et al. "Inhibition of experimental allergic encephalomyelitis in the Lewis rat by paclitaxel" Journal of Neuroimmunology (2000) vol. 108, pp. 103-111.

Case et al., "IT-101 nanoparticle characterization," Jul. 2010, 2010 ACS National Meeting (Aug. 22-26, 2010) Boston, MA.

Ceccato et al., "Molecular dynamics of novel a-cyclodextrin adducts studied by 13C-NMR relaxation," J. Phys. Chem., 1997, vol. 101, No. 26, pp. 5094-5099.

Cheng et al., "Antitumor activity of linear-cyclodextrin polymer conjugates of camptothecin," Nov. 1, 2003, AlChE Annual Meeting, (Nov. 16-21, 2003) San Francisco, CA.

Cheng et al., "Antitumor activity of systemic delivered camptothecin conjugates of linear, cyclodextrin-based polymers," 11th International Symposium on Recent Advances in Drug Delivery Systems (Mar. 3-6, 2003), Salt Lake City, UT.

Cheng et al., "Antitumor activity of β-cyclodextrin polymer-camptothecin conjugates," Molecular Pharmaceutics, vol. 1, pp. 183-193 (available online Apr. 3, 2004).

Cheng et al., "Linear, cyclodextrin-based polymers for the delivery of broad ranging therapeutics," Sep. 7, 2003, 2003 ACS Meeting (Sep. 7-11, 2003) New York, NY.

Cheng et al., "Synthesis of linear, β-cyclodextrin-based polymers and their camptothecin conjugates," Bioconjugate Chem, vol. 14, pp. 1007-1017 (available online Aug. 27, 2003).

Chung. "Managing Premedications and the Risk for Reactions ro Infusional Monoclonal Antibody Therapy". The Oncologist. (2008) 13:724-732.

Clinical Trail 2103, Study 11. Updated Jan. 12, 2006.

Forgacs et al., "Interactions of some steroid drugs with b-cyclodextrin polymers," Journal of Chromatography A, 1999, vol. 845, No. 1 & 2, pp. 447-453.

Francis et al., "Polyethylene glycol modification: relevance of improved methodology to tumour targeting", J. Drug Targeting 3:321-340 (1996).

Frese-Schaper et al. "Reversal of Established Lupus Nephritis and Prolonged Survival of New Zealand Black x New Zealand White Mice Treated with the Topoisomerase I Inhibitor Irinotecan" Journal of Immunology; 2010, 184: pp. 2175-2182.

Fuchs et al. "Phase III Comparison of Two Irinotecan Dosing Regimens in Second-Line Therapy of Metastatic Colorectal Cancer" Journal of Clinical Oncology (2003) vol. 21, No. 5, pp. 807-814.

Fujita et al., "Guest-induced conformational change of b-cyclodextrin capped with an environmentally sensitive chromophore," Bioorganic Chemistry, 1982, vol. 11, pp. 72-84.

Fujita et al., "Selective recognition of alkanoates by a b-cyclodextrin flexibly capped with a chromophore," Bioorganic Chemistry, 1982, vol. 11, pp. 108-114.

Gao et al., "Potentiation of cationic liposome-mediated gene delivery by polycations," Biochemistry, 1996, vol. 35, pp. 1027-1036.

Gasparini et al. "Combination of Antiangiogenic Therapy With Other Anticancer Therapies: Results, Challenges, and Open Questions" Journal of Clinical Oncology (2005) vol. 23, No. 6, pp. 1295-1311.

Gautschi et al. "Origin and prognostic value of circulating KRAS mutations in lung cancer patients" Cancer Letters (2007) vol. 254, pp. 265-273.

Gonzalez et al., "New Class of Polymers for the Delivery of Macromolecular Therapeutics" Bioconjugate Chemistry, vol. 10, No. 6 pp. 1068-1074 (1999).

Gopin et al., "New chemical adaptor unit designed to release a drug from a tumor targeting device by enzymatic triggering," Bioorganic & Medicinal Chemistry, Elsevier Science, 2004, vol. 12, pp. 1853-1858.

Gosselet et al., "Association of hydrophobically modified poly (N,N-dimethylacrylamide hydroxyethylmethacrylate) with water soluble β-cyclodextrin polymers," Colloids and Surfaces: A: Physicochemical and Engineering Aspects, 1999, vol. 155, pp. 177-188.

Greenwald, R. "PEG drugs: and overview" Journal of Controlled Release (2001) vol. 74, pp. 159-171.

Guéritte et al., "General and Recent Aspects of the Chemistry and Structure-Activity Relationships of Tazoids", Current Pharmaceutical Design, vol. 7, pp. 1229-1249 (2001).

Habus et al., "Synthesis, hybridization properties, nuclease stability, and cellular uptake of the oligonucleotide-amino-b-cyclodextrins and adamantane conjugates," Bioconjugate Chem., 1995, vol. 6, No. 4, pp. 327-331.

Hammer et al., "Practical approach to solid-phase synthesis of C-terminal peptide amides under mild conditions based on a photolysable anchoring linkage," Int. J. Peptide Protein Res., 1990, vol. 36, pp. 31-45.

Harada et al., "Macromolecular recognition by cyclodextrins (I) Inclusion of water-soluble polymers by cyclodextrins," Polymer Preprints, 1991, vol. 40, pp. 5-11, Abstract 4L 10 at p. E 1172, Japan (English Edition).

Harada et al., "Synthesis of a tubular polymer from threaded cyclodextrins," Nature, 1993, vol. 364, pp. 516-518.

Harada et al., "The molecular necklace: a rotaxane containing many threaded a-cyclodextrins," Nature, 1992, vol. 356, pp. 325-327.

Hazum et al., "A photocleavable protecting group for the thiol function of cysteine," Proc. 16th Sup. European Peptide Sym., 1980, pp. 105-110.

Heath et al., "Nanomedicine—revolutionizing the fight against cancer," Scientific American, Jan. 19, 2009.

Heath et al., "Nanotechnology and cancer," Annual Review of Medicine 2008 (published online Oct. 15, 2007), vol. 59, pp. 251-265.

Heidel et al., "Clinical developments in nanotechnology for cancer therapy," Pharm. Res. (online), Jun. 12, 2010.

Heidel, "Linear cyclodextrin-containing polymers and their use as delivery agents," Expert Opinion on Drug Delivery, 2006, vol. 3, No. 5, pp. 641-646.

(56) References Cited

OTHER PUBLICATIONS

Henry, "Synthetic chemistry at biotech firms," Chemical & Engineering News, Apr. 2, 2001, vol. 79, No. 14, American Chemical Society.
Hisamatsu et al., "Study on specific modification of glucosyl cyclodextrins," Starch, 1992, vol. 44, pp. 188-191.
Hoffman, "Chromatography of nucleic acids on cross-linked cyclodextrin gels having inclusion-forming capacity," J. Macromol. Sci.-Chem., 1973, vol. A7, No. 5, pp. 1147-1157.
Holmes et al., "Reagents for combinatorial organic synthesis: development of a new o-nitrobenzyl photolabile linker for solid phase synthesis," J. Org. Chem., 1995, vol. 60, pp. 2318-2319.
Homsi et al., "Phase I trial of poly-L-glutamate camptothecin (CT-2106) administered weekly in patients with advanced solid malignancies", Clin. Cancer Res., 2007, vol. 13, pp. 5855-5861.
Hristova-Kazmierski et al., "A new approach to enhanced bioavailability of biologically active peptides: conjugation of a d-opioid agonist to b-cyclodextrin," Bioorganic and Medicinal Chemistry Letters, 1993, vol. 3, No. 5, pp. 831-834.
Huh et al., "Synthesis of a-cyclodextrin-conjugated poly (e-lysine)s and their inclusion complexation behavior," Macromol. Rapid Commun., 2002, vol. 23, pp. 179-182.
Husain et al., "Complexation of doxorubicin with β- and g-cyclodextrins," Applied Spectroscopy, 1992, vol. 46, pp. 652-658.
Hwang et al., "Effects of structure of β-cyclodextrin-containing polymers on gene delivery," Bioconjugate Chem., 2001, vol. 12, No. 2, pp. 280-290.
Hwang et al., "a-Methylprednisolone conjugated cyclodextrin polymer-based nanoparticles for rheumatoid arthritis therapy," International Journal of Nanomedicine, 2008, vol. 3, pp. 359-371 (available online Sep. 2008).
Hwang et al., "Preclinical efficacy of the comptothecin-polymer conjugate IT-101 in multiple cancer models", Clinical Cancer Research, Mar. 1, 2006, vol. 12, No. 5.
Ikeda et al., "Supramolecular netwrok formation through inclusion complexation of an a-cyclodextrin-based molecular tube", Macromol. Rapid Comm. 21:1257-1262 (2000).
Ikezoe et al. "HIV-1 Protease Inhibitor, Ritonavir: A Potent Inhibitor of CYP3A4, Enhanced the Anticancer Effects of Docetaxel in Androgen-Independent Prostate Cancer Cells In vitro and In vivo" Cancer Research (2004) vol. 64, pp. 7426-7431.
International Preliminary Report on Patentability including Written Opinion from International Application Serial No. PCT/US2010/048279 dated Nov. 8, 2010.
International Search Report and Written Opinion for International Applcation No. PCT/US13/63529 dated Jan. 29, 2014.
International Search Report and Written Opinion for International Application No. PCT/US2013/021402 dated Mar. 19, 2013.
International Search Report and Written Opinion for International Application No. PCT/US2014/040230 dated Nov. 18, 2014.
International Search Report and Written Opinion for International Application No. PCT/US2014/057749 dated Dec. 19, 2014.
International Search Report dated Aug. 23, 2012 from International Application PCT/US12/034459.
International Search Report dated Jan. 26, 2011 from International Application No. PCT/US2010/57913.
International Search Report dated Jul. 24, 2012 from International Application No. PCT/US 12/23308.
International Search Report dated Nov. 2, 2011 from International Application No. PCT/US11/37025.
International Search Report dated Nov. 8, 2010 from International Application No. PCT/US10/48973.
International Search Report dated Nov. 8, 2010 from International Application No. PCT/US2010/048279.
International Search Report dated Oct. 23, 2012 from International Application No. PCT/US12/50308.
International Search Report for International Application No. PCT/US2006/005448 dated Aug. 21, 2007.
Krasner, C. et al., Proceedings of the 107th Annual Meeting of the American Association for Cancer Research (Apr. 16, 2016), Abstract nr CT090.
Kikuchi et al., "Effects of weekly bevacizumab and pegylated liposomal doxorubicin in heavily pretreated patients with recurrent or progressed ovarian cancer" Journal of Clinical Oncology, vol. 27, No. 15, 2009, pp. 5547.
Zamboni, "Liposomal, nanoparticle, and conjugated formulations of anticancer agents" Clin. Cancer Res., vol. 11, No. 23, 2005, pp. 8230-8234.
Burger, "Experience with bevacizumab in the management of epithelial ovarian cancer" Journal of Clinical Oncology, vol. 25, No. 20, 2007, pp. 2902-2908.
Wright et al., "Bevacizumab combination therapy in recurrent, platinum-refractory, epithelial ovarian carcinoma" Cancer, vol. 107, 2006, pp. 83-89.
Sanoff et al., "Phase I/II trial of nano-camptothecin CRLX101 with capecitabine and radiotherapy as neoadjuvant treatment for locally advanced rectal cancer," Nanomedicine: nanotechnology, biology, and medicine, 2019, vol. 18, pp. 189-195.
Tian et al., "CRLX101, a nanoparticle-drug conjugate containing camptothecin, improves rectal cancer chemoradiotherapy by inhibiting DNA repair and HIF-1a," Cancer Res., 2017, vol. 77, No. 1, pp. 112-122.
Udo et al., "5-Fluorouracil acetic acid/b-cyclodextrin conjugates: Drug release behavior in enzymatic and rat cecal media" International Journal of Pharmaceutics, vol. 388, No. 1-2, pp. 95-100, 2010.
Extended European Search Report for EP19165905.1 dated Oct. 10, 2019.
Almagro et al., "Occurrence of subacute lupus erythematosus after treatment with systemic fluorouracil" Journal of Clinical Oncology, vol. 29, No. 20, 2011, pp. e613-e615.
Soares et al., "Inflammatory intestinal damage induced by 5-fluorouracil requires IL-4" Cytokine, vol. 61, No. 1, 2013, pp. 46-49.
Ha et al., "Onset of manic episode during chemotherapy wih 5-fluorouracil" Psychiatry Investigations, vol. 8, No1. 1, 2011, pp. 71-73.
Sara et al., "5-fluorouracil and cardiotoxicity: A review" Therapeutic Advances in Medical Oncology, vol. 10, 2018, pp. 1-18.
Han et al., "Systemic 5-fluorouracil treatment causes syndrome of delayed myelin destruction in the central nervous system" Journal of Biology, vol. 7, No. 4, 2008, pp. 12.1-12.22.
Werbel et al., "Topical application of 5-fluorouracil associated with distant seborrheic dermatitis-like eruption: Case report and review of seborrheic dermatitis cutaneous reactions afte systemic or topical treatment with 5-fluorouracil" Dermatol. Ther. vol. 8, No. 3, 2018, pp. 495-501.
Veldman et al., "Coformulated N-octanoyl-glucosylceramide improves cellular delivery and cytotoxicity of liposomal doxorubin" J. Pharmacol. Exp. Ther., 2005, vol. 315, No. 2, Abstract.
Rochlitz et al., "Combination of bevacizumab and 2-weekly pegylated liposomal doxorubicin as first-line therapy for locally recurrant or metastatic breast cancer. A multicenter, single-arm phase II trial (SAKK 24/06)" Annals of Oncology, 2011, vol. 22, pp. 80-85.
Doxil® product label dated May 2007, obtained from https://www.accessdata.fda.gov/drugsatfda_docs/label/2007/050718s029lbl.pdf (33 pages).
Gravanis et al., "tPA as a therapeutic target in stroke" Exper Opin. Ther. Targets, 2008, vol. 12, No. 2, (18 pages).
Bomfin et al., "5-fluorouracil induces inflammation and oxidation stress in the major salivary glands affecting salivary flow and saliva composition" Biochemical pharmacology, vol. 145, pp. 34-45, 2017.
Levesque et al., "Eczema herpeticum complicating topical 5-fluorouracil therapy" Dermatitis, vol. 23, No. 5, pp. 240-241, 2012.
Goette et al., "Allergic contact dermatitis from topical fluorouracil" Arch Dermatol, vol. 113, pp. 196-198, 1977.
Feng et al., "Secondary diabetes associated with 5-fluorouracil-based chemotherapy regimens in non-diabetic patients with colorectal cancer: results from a single-centre cohort study" Colorectal Dis., vol. 15, No. 1, pp. 27-33, 2013.

(56) References Cited

OTHER PUBLICATIONS

Yingjuan Wang, et al., "Influences of Camptothecin on Mouse T Lymphocyte Activation" Proliferation and Cell-Cycle, vol. 24, No. 6, pp. 1178-1182, 2008.
Huixiao Wang et al., "Action Mechanism and Clinical Applications of Immunosuppressive Agents" Heilongjiang Medicine Journal, vol. 20, No. 4, pp. 363-366, 2007.
Yumei Sang et al., "Applications of Immunosuppressive Agents in Autoimmune Diseases" Journal of Foreign Medicine (Pediatrics), No. 3, pp. 145-146, 1981.

\* cited by examiner

FIG. 1

| STEP 1: PROVIDE A VESSEL HOUSING A VOLUME OF COOLED NON-SOLVENT |

| STEP 2: INTRODUCE A POLYMER-CONTAINING SOLUTION INTO THE VESSEL TO FORM A MIXTURE COMPRISING A LIQUID AND A POLYMER; AND MAINTAIN THE MIXTURE UNDER CONDITIONS TO PRECIPITATE POLYMER FROM MIXTURE |

| STEP 3: EXTRACT A PORTION OF THE LIQUID AND RECIRCULATE THE EXTRACTED LIQUID THROUGH THE VESSEL |

| STEP 4: ADD A SECOND VOLUME OF A COOLED NON-SOLVENT TO THE VESSEL |

| STEP 5: COLLECT PRECIPITATED POLYMER |

| STEP 6: DRY POLYMER TO REMOVE RESIDUAL LIQUID |

| STEP 7: STORE THE POLYMER FOR LATER USE |

METHODS AND SYSTEMS FOR POLYMER PRECIPITATION AND GENERATION OF PARTICLES

CLAIMS OF PRIORITY

This application is a continuation of U.S. patent application Ser. No. 14/042,996, filed Oct. 1, 2013, which claims priority to U.S. Provisional Patent Application No. 61/708,797 filed Oct. 2, 2012. The entire contents of each of the foregoing application is incorporated herein by reference.

BACKGROUND

Cyclodextrin-containing polymer (CDP) conjugates can be utilized as carriers of therapeutic agents. Typically, such CDP-therapeutic agent conjugates can be prepared by introducing a polymer-containing solution into a non-solvent, such as acetone, to precipitate the polymer conjugate. The precipitation process is relatively slow and generally includes formation of a cloudy solution followed by generation of polymeric strands, which eventually coalesce into a polymeric aggregate. Multiple decantation and rinsing steps are then performed to remove unreacted impurities, e.g., unconjugated polymer, unconjugated therapeutic agent, and solvents. The CDP-therapeutic agent conjugates can then be dispersed in water to spontaneously form particles, e.g., nanoparticles.

The scaling of the above process for generating particles, e.g., nanoparticles on a commercial scale can be difficult. For example, the precipitated CDP-therapeutic agent conjugates have a tendency to wrap around mixing impellors and must be manually stripped off. Additionally, the process for precipitating these polymer conjugates can be difficult to reproduce. Accordingly, there exists a need for improved methods for precipitating CDP-therapeutic agent conjugates from a polymer-containing solution and for generating particles, e.g., nanoparticles.

SUMMARY

The disclosure provides, inter alia, processes for precipitating a cyclodextrin-containing polymer (CDP) inhibitor conjugate, e.g., CDP-camptothecin conjugate, e.g., CRLX101, or a CDP-inhibitor conjugate described herein, from a polymer-containing solution.

In some embodiments, the CDP-inhibitor conjugate, e.g., CDP-camptothecin conjugate, e.g., CRLX101, or a CDP-inhibitor conjugate described herein, is as shown below, which is referred to herein as "CRLX101."

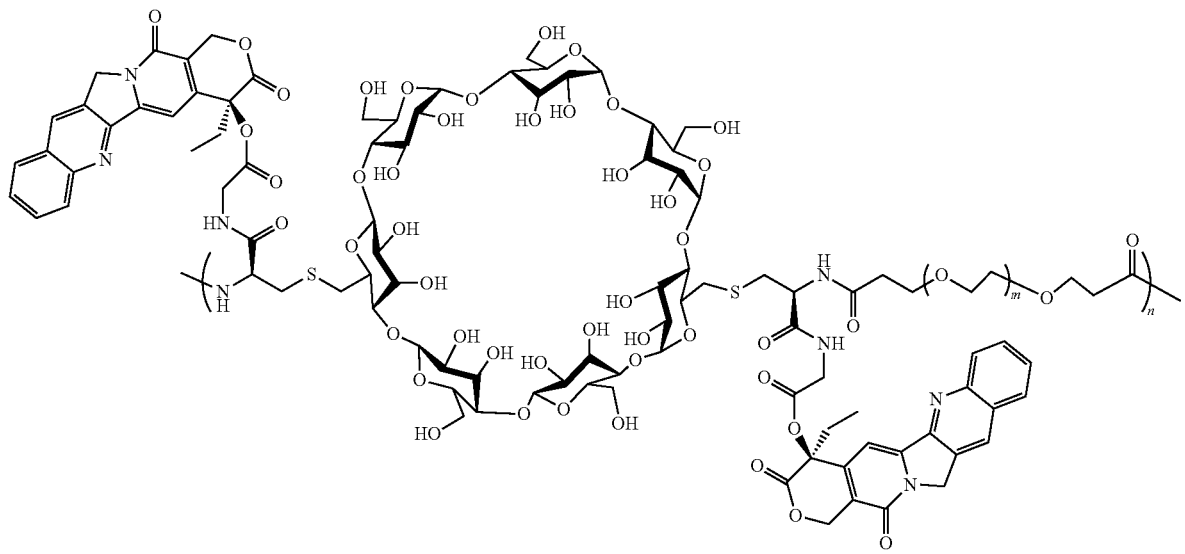

In the above structure:

m=about 77 or the molecular weight of the PEG moiety is 3.4 kDa, e.g., 3.4 kDa +/−10%;

n=is from about 10 to about 18 (e.g., about 14);

the molecular weight of the polymer backbone (i.e., the polymer minus the camptothecin-glycine (CPT-gly), which results in the cysteine moieties having a free —C(O)OH) is from about 48 to about 85 kDa;

the polydispersity of the polymer backbone is less than about 2.2; and the loading of the CPT onto the polymer backbone is from about 6 to about 13% by weight, wherein 13% is theoretical maximum, meaning, in some instances, one or more of the cysteine residues has a free —C(O)OH (i.e., it lacks the CPT-gly).

The precipitation process can include providing a vessel containing an agitated cooled non-solvent, e.g., a solvent which does not solubilize the CDP-inhibitor conjugate, e.g., CDP-camptothecin conjugate, e.g., CRLX101, or a CDP-inhibitor conjugate described herein, introducing a polymer-containing solution into the cooled non-solvent to form a mixture comprising a liquid and the CDP-inhibitor conjugate, e.g., CDP-camptothecin conjugate, e.g., CRLX101, or a CDP-inhibitor conjugate described herein. The mixture is maintained under conditions to precipitate at least a portion of the CDP-inhibitor conjugate, e.g., CDP-camptothecin conjugate, e.g., CRLX101, or a CDP-inhibitor conjugate described herein, from the mixture, thereby precipitating at least a portion of the CDP-inhibitor conjugate, e.g., CDP-camptothecin conjugate, e.g., CRLX101, or a CDP-inhibitor conjugate described herein. The mixture can then be filtered to separate the precipitated CDP-inhibitor conjugate, e.g., CDP-camptothecin conjugate, e.g., CRLX101, or a CDP-inhibitor conjugate described herein, from the liquid. The precipitated CDP-inhibitor conjugate, e.g., CDP-camptothecin conjugate, e.g., CRLX101, or a CDP-inhibitor conjugate described herein, can be stored as a solid, e.g., stored in a non-solvent or under an inert environment, or can be stored as a liquid, e.g., stored in an ambient environment.

The precipitated CDP-inhibitor conjugate, e.g., CDP-camptothecin conjugate, e.g., CRLX101, or a CDP-inhibitor conjugate described herein, can be further processed. In some embodiments, the precipitated CDP-inhibitor conjugate, e.g., CDP-camptothecin conjugate, e.g., CRLX101, or a CDP-inhibitor conjugate described herein, can be incorporated into a particle, e.g., a nanoparticle. The resulting particle can be formulated into a pharmaceutical composition or dosage form, which can be administered to a subject, e.g., a subject in need thereof, for example in the treatment of a disorder, e.g. a proliferative disorder, an inflammatory/autoimmune disorder, cardiovascular disorder, a metabolic disorder, a central nervous system disorder, or neurological deficit disorder.

Accordingly, in a first aspect, the disclosure provides a process for precipitating a CDP-inhibitor conjugate, e.g., CDP-camptothecin conjugate, e.g., CRLX101, or a CDP-inhibitor conjugate described herein, from a polymer-containing solution, the process comprising: providing a vessel containing a volume of a cooled non-solvent; agitating the cooled non-solvent; introducing the polymer-containing solution into the cooled non-solvent to form a mixture comprising a liquid and the CDP-inhibitor conjugate, e.g., CDP-camptothecin conjugate, e.g., CRLX101, or a CDP-inhibitor conjugate described herein; and maintaining the mixture under conditions to precipitate at least a portion of the CDP-inhibitor conjugate, e.g., CDP-camptothecin conjugate, e.g., CRLX101, or a CDP-inhibitor conjugate described herein, from the mixture, thereby precipitating at least a portion of the CDP-inhibitor conjugate, e.g., CDP-camptothecin conjugate, e.g., CRLX101, or a CDP-inhibitor conjugate described herein.

In some embodiments, the mixture is maintained at a temperature of about −50 to about −100 degrees Celsius.

In some embodiments, the temperature of the mixture is less than −90 degrees Celsius, less than −80 degrees Celsius, less than −70 degrees Celsius, or less than −60 degrees Celsius. In some embodiments, the temperature of the mixture is −78 degrees Celsius.

In some embodiments, at least a portion of the liquid from the vessel can be removed subsequent to precipitation of the CDP-inhibitor conjugate, e.g., CDP-camptothecin conjugate, e.g., CRLX101, or a CDP-inhibitor conjugate described herein, thereby separating the precipitated CDP-inhibitor conjugate, e.g., CDP-camptothecin conjugate, e.g., CRLX101, or a CDP-inhibitor conjugate described herein, from the mixture.

In some embodiments, the portion of the liquid containing the cooled non-solvent and the polymer-containing solution can be re-introduced into the vessel, thereby precipitating a second portion of the CDP-inhibitor conjugate, e.g., CDP-camptothecin conjugate, e.g., CRLX101, or a CDP-inhibitor conjugate described herein.

In some embodiments, a second volume of cooled non-solvent is added to the vessel subsequent to removal of at least a portion of the liquid from the vessel.

In some embodiments, the precipitated CDP-inhibitor conjugate, e.g., CDP-camptothecin conjugate, e.g., CRLX101, or a CDP-inhibitor conjugate described herein, is filtered from the mixture.

In some embodiments, the precipitated CDP-inhibitor conjugate, e.g., CDP-camptothecin conjugate, e.g., CRLX101, or a CDP-inhibitor conjugate described herein, comprises a plurality of particles, e.g., nanoparticles, in the non-solvent.

In some embodiments, the precipitated CDP-inhibitor conjugate, e.g., CDP-camptothecin conjugate, e.g., CRLX101, or a CDP-inhibitor conjugate described herein, is filtered cold, e.g., at a temperature of about −50 degrees Celsius to about −100 degrees Celsius.

In some embodiments, the precipitated CDP-inhibitor conjugate, e.g., CDP-camptothecin conjugate, e.g., CRLX101, or a CDP-inhibitor conjugate described herein, is filtered at room temperature.

In some embodiments, the filtered precipitated CDP-inhibitor conjugate, e.g., CDP-camptothecin conjugate, e.g., CRLX101, or a CDP-inhibitor conjugate described herein, is stored in the cooled non-solvent, e.g., in a solid form, e.g., flakes or shards.

In some embodiments, the filtered precipitated CDP-inhibitor conjugate, e.g., CDP-camptothecin conjugate, e.g., CRLX101, or a CDP-inhibitor conjugate described herein, is stored under a vacuum environment, e.g., in a solid form, e.g., flakes or chards.

In some embodiments, the filtered precipitated CDP-inhibitor conjugate, e.g., CDP-camptothecin conjugate, e.g., CRLX101, or a CDP-inhibitor conjugate described herein, is stored under an ambient environment, e.g., the filtered precipitated CDP-inhibitor conjugate, e.g., CDP-camptothecin conjugate, e.g., CRLX101, or a CDP-inhibitor conjugate described herein, is stored in a form other than a solid, e.g., a liquid or oil.

In some embodiments, the non-solvent comprises acetone, e.g., a polar aprotic solvent.

In some embodiments, the non-solvent comprises acetone comprising less than 20% by volume of water, less than 15% by volume of water, less than 10% by volume of water, less than 5% by volume of water, less than 2% by volume of water, less than 1% by volume of water, less than 0.5% by volume of water, or less than 0.1% by volume of water.

In some embodiments, the temperature of the non-solvent is from about −50 to about −100 degrees Celsius.

In some embodiments, the temperature of the non-solvent is less than −90 degrees Celsius, less than −80 degrees Celsius, less than −70 degrees Celsius, or less than −60 degrees Celsius. In some embodiments, the temperature of the non-solvent is −78 degrees Celsius.

In some embodiments, the temperature of the non-solvent is −78 degrees Celsius.

In some embodiments, the CDP-inhibitor conjugate, e.g., CDP-camptothecin conjugate, e.g., CRLX101, or a CDP-inhibitor conjugate described herein, comprises a plurality of cyclodextrin moieties.

In some embodiments, the polymer-containing solution comprises one or more of a CDP-inhibitor conjugate, e.g., CDP-camptothecin conjugate, e.g., CRLX101, or a CDP-inhibitor conjugate described herein, an unconjugated topoisomerase inhibitor, e.g., camptothecin or camptothecin derivative, an unconjugated CDP, a conjugation reaction side product, and a process solvent.

In some embodiments, the polymer-containing solution comprises an unconjugated polymer, e.g., a CDP that did not conjugate with an inhibitor, e.g., camptothecin or camptothecin derivative, during the conjugation reaction. In some embodiments, the polymer-containing solution comprises an unconjugated inhibitor, e.g., camptothecin or camptothecin derivative that did not conjugate with the CDP during the conjugation reaction. In some embodiments, the polymer-containing solution comprises one or more of the reagents utilized in the preparation of the CDP-inhibitor conjugate, e.g., CDP-camptothecin conjugate, e.g., CRLX101, or a CDP-inhibitor conjugate described herein. In some embodiments, the polymer-containing solution comprises unreacted reagents such as cyclodextrin (CD), e.g., beta-cyclodextrin, CD-biscysteine. In some embodiments, the unconjugated therapeutic agent is camptothecin (CPT), camptothecin modified with glycine, e.g., CPT-glycine. In some embodiments, the polymer-containing solution comprises CD-biscysteine copolymerized with PEG 3.4 kDa, e.g., 3.4 kDa +/−10%. In some embodiments, the polymer-containing solution comprises one or more of an activated monomer, such as PEG-DiSBA.

In some embodiments, the process solvent comprises acetone, ether, alcohol, tetrahydrofuran, 2-pyrrolidone, N-methyl-2-pyrrolidone, dimethylformamide, dimethylacetamide, methyl acetate, ethyl formate, methyl ethyl ketone, methyl isobutyl ketone, methyl propyl ketone, isopropyl ketone, isopropyl acetate, acetonitrile and dimethyl sulfoxide, or a combination thereof.

In some embodiments, at least one of the cyclodextrin moieties comprises α-cyclodextrin.

In some embodiments, at least one of the cyclodextrin moieties comprises β-cyclodextrin.

In some embodiments, at least one of the cyclodextrin moieties comprises γ-cyclodextrin.

In another aspect, the disclosure provides a system for precipitating a CDP-inhibitor conjugate, e.g., CDP-camptothecin conjugate, e.g., CRLX101, or a CDP-inhibitor conjugate described herein, from a polymer-containing solution, the system comprising:

a vessel for containing a fluid (e.g., a cooled non-solvent or a mixture comprising a liquid and the polymer) the vessel having at least one input port and an output port;

a cooling system in communication with the vessel, e.g., a cooling jacket, configured to cool and maintain the temperature of the fluid, e.g., a cooled non-solvent or a mixture comprising a liquid and the polymer, in the vessel;

wherein said input port is configured to allow introduction of the polymer-containing solution into the vessel to precipitate at least a portion of the CDP-inhibitor conjugate, e.g., CDP-camptothecin conjugate, e.g., CRLX101, or a CDP-inhibitor conjugate described herein.

In some embodiments, a pump can be in communication with the vessel and configured to cause a flow of the fluid, e.g., the cooled non-solvent or the mixture comprising the liquid and the CDP-inhibitor conjugate, e.g., CDP-camptothecin conjugate, e.g., CRLX101, or a CDP-inhibitor conjugate described herein, through the vessel.

In some embodiments, the vessel further comprises an agitator, e.g., magnetic or mechanical agitator.

In some embodiments, the non-solvent is cooled prior to introduction of the polymer-containing solution into the vessel.

In some embodiments, the temperature of the non-solvent is less than −90 degrees Celsius, less than −80 degrees Celsius, less than −70 degrees Celsius, or less than −60 degrees Celsius. In some embodiments, the temperature of the non-solvent is −78 degrees Celsius.

In some embodiments, the output port is configured to allow the removal of the fluid, subsequent to the precipitation of at least a portion of the CDP-inhibitor conjugate, e.g., CDP-camptothecin conjugate, e.g., CRLX101, or a CDP-inhibitor conjugate described herein.

In some embodiments, a reservoir can be in fluid communication with the vessel for storing a quantity of the polymer-containing solution.

In some embodiments, a fluid passage can extend between the output port and the input port.

In some embodiments, the pump can be in communication with the fluid passage for establishing a liquid recirculation loop through the vessel.

In some embodiments, a recovery port can be in communication with the fluid passage to drain any of the cooled solvent and the liquid from the recirculation loop.

In some embodiments, a reservoir for storing the non-solvent, the reservoir can be in fluid communication with the vessel.

In some embodiments, the vessel can contain a quantity of the non-solvent.

In another aspect, the disclosure provides a process for generating particles, e.g., nanoparticles, comprising:

providing a vessel containing a cooled non-solvent; agitating the cooled non-solvent; introducing a polymer-containing solution comprising a CDP-inhibitor conjugate, e.g., CDP-camptothecin conjugate, e.g., CRLX101, or a CDP-inhibitor conjugate described herein, into the cooled non-solvent to form a mixture comprising a liquid and the CDP-inhibitor conjugate, e.g., CDP-camptothecin conjugate, e.g., CRLX101, or a CDP-inhibitor conjugate described herein; and maintaining the mixture under conditions to precipitate at least a portion of the CDP-inhibitor conjugate, e.g., CDP-camptothecin conjugate, e.g., CRLX101, or a CDP-inhibitor conjugate described herein, from the mixture, thereby precipitating at least a portion of the CDP-inhibitor conjugate, e.g., CDP-camptothecin conjugate, e.g., CRLX101, or a CDP-inhibitor conjugate described herein; and isolating at least a portion of the precipitated CDP-inhibitor conjugate, e.g., CDP-camptothecin conjugate, e.g., CRLX101, or a CDP-inhibitor conjugate described herein; and suspending the precipitated CDP-inhibitor conjugate, e.g., CDP-camptothecin conjugate, e.g., CRLX101, or a CDP-inhibitor conjugate described herein, in an aqueous solution, thereby generating particles, e.g., nanoparticles.

In some embodiments, the pH of the aqueous solution is from about 2 to about 6, e.g., pH 3.

In some embodiments, the polymer-containing solution comprises one or more of a CDP-inhibitor conjugate, e.g., CDP-camptothecin conjugate, e.g., CRLX101, or a CDP-inhibitor conjugate described herein, an unconjugated therapeutic agent, an unconjugated polymer, a conjugation reaction side product, and a process solvent.

In some embodiments, the polymer-containing solution comprises an unconjugated polymer, e.g., a CDP that did not conjugate with an inhibitor, e.g., camptothecin or camptothecin derivative, during the conjugation reaction. In some embodiments, the polymer-containing solution comprises an unconjugated camptothecin or camptothecin derivative, e.g., camptothecin or camptothecin derivative that did not conjugate with the CDP during the conjugation reaction. In some embodiments, the polymer-containing solution comprises one or more of the reagents utilized in the preparation of the CDP-inhibitor conjugate, e.g., CDP-camptothecin conjugate, e.g., CRLX101, or a CDP-inhibitor conjugate described herein. In some embodiments, the polymer-containing solution comprises unreacted reagents such as cyclodextrin (CD), e.g., beta-cyclodextrin, CD-biscysteine. In some embodiments, the unconjugated therapeutic agent inhibitor is camptothecin (CPT), or a camptothecin modified with glycine, e.g., CPT-glycine. In some embodiments, the polymer-containing solution comprises CD-biscysteine copolymerized with PEG 3.4 kDa, e.g., 3.4 kDa +/−10%. In some embodiments, the polymer-containing solution comprises one or more of an activated monomer, such as PEG-DiSBA.

In some embodiments, the process can cause a recirculating flow of the cooled non-solvent through the vessel and introducing the polymer-containing solution into the flowing cooled non-solvent.

In some embodiments, at least one of the cyclodextrin moieties comprises α-cyclodextrin.

In some embodiments, at least one of the cyclodextrin moieties comprises β-cyclodextrin.

In some embodiments, at least one of the cyclodextrin moieties comprises γ-cyclodextrin.

In some embodiments, the process solvent comprises acetone, ether, alcohol, tetrahydrofuran, 2-pyrrolidone, N-methyl-2-pyrrolidone, dimethylformamide, dimethylacetamide, methyl acetate, ethyl formate, methyl ethyl ketone, methyl isobutyl ketone, methyl propyl ketone, isopropyl ketone, isopropyl acetate, acetonitrile, and dimethyl sulfoxide, or a combination thereof.

In some embodiments, the non-solvent comprises methanol, ethanol, acetone, n-propanol, isopropanol, n-butanol, ethyl ether, methyl isobutyl ketone or ethyl acetate or a combination thereof.

In some embodiments, the process can comprise filtering the particles, e.g., nanoparticles.

In some embodiments, the filtering step can comprise utilizing tangential flow filtration.

In some embodiments, the process can comprise collecting the particles, e.g., nanoparticles.

In some embodiments, the process can comprise lyophilizing the collected particles, e.g., nanoparticles.

In some embodiments, the particles, e.g., nanoparticles, exhibit an average particle size less than about 1 micron.

In some embodiments, the nanoparticles exhibit an average particle size less than about 500 nm.

In some embodiments, the nanoparticles exhibit an average particle size less than about 200 nm.

In some embodiments, the nanoparticles exhibit an average particle size less than about 100 nm.

In some embodiments, the nanoparticles exhibit an average particle size less than about 50 nm.

In some embodiments, the nanoparticles exhibit an average particle size in a range of about 5 nm to about 200 nm.

In some embodiments, the process can comprise analyzing the particle, e.g., nanoparticle by any of transmission electron microscopy, dynamic light scattering, static light scattering, and size exclusion chromatography.

In a further aspect, the disclosure provides a plurality of particles, e.g., nanoparticles, generated according to the process described herein.

In some embodiments, the plurality of particles includes at least about 100 grams of the particles.

In some embodiments, the plurality of particles includes at least about 200 grams of the particles.

In some embodiments, the nanoparticles exhibit an average particle size less than about 200 nm.

In some embodiments, the nanoparticles exhibit an average particle size less than about 100 nm.

In some embodiments, the nanoparticles exhibit an average particle size less than about 50 nm.

In some embodiments, the nanoparticles exhibit an average particle size in a range of about 5 nm to about 200 nm.

In a further aspect, the disclosure provides a product produced by the process described herein.

In a further aspect, the disclosure provides a preparation comprising the CDP-inhibitor conjugate, e.g., CDP-camptothecin conjugate, e.g., CRLX101, or a CDP-inhibitor conjugate described herein, precipitated by the process described herein.

In some embodiments, the preparation contains less than about 50, less than about 40, less than about 30, less than about 20, less than about 10, less than about 5, or less than about 1% by weight of a solvent.

In some embodiments, the solvent comprises acetone.

In some embodiments, the solvent comprises acetone comprising less than 20% by volume of water, less than 15% by volume of water, less than 10% by volume of water, less than 5% by volume of water, less than 2% by volume of water, less than 1% by volume of water, less than 0.5% by volume of water, or less than 0.1% by volume of water.

BRIEF DESCRIPTION OF THE DRAWINGS

FIG. 1 is a flow chart depicting various steps of a process for precipitating CDP-inhibitor conjugate, e.g., CDP-camptothecin conjugate, e.g., CRLX101, or a CDP-inhibitor conjugate described herein.

DETAILED DESCRIPTION

Figure 2:
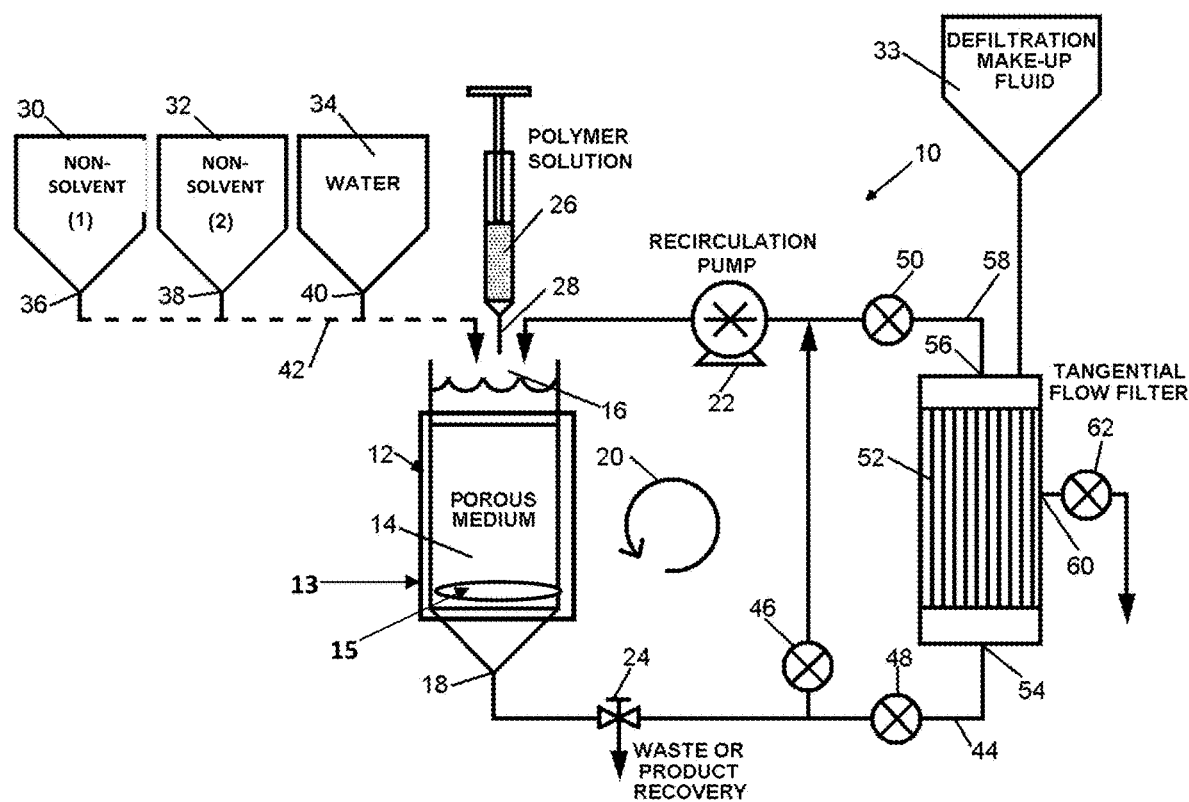
FIG. 2 is a schematic diagram of a system for precipitating CDP-inhibitor conjugate, e.g., CDP-camptothecin conjugate, e.g., CRLX101, or a CDP-inhibitor conjugate described herein, and generating particles, e.g., nanoparticles.

Described herein are methods of precipitating CDP-inhibitor conjugates, e.g., CDP-camptothecin conjugates, e.g., CRLX101, or CDP-inhibitor conjugates described herein, from a polymer-containing solution. The CDP-inhibitor conjugate, e.g., CDP-camptothecin conjugate, e.g., CRLX101, or a CDP-inhibitor conjugate described herein, can be precipitated from a polymer-containing solution by contacting the solution with a cooled non-solvent, e.g., cooled acetone, to provide a mixture comprising a liquid and the CDP-inhibitor conjugate, e.g., CDP-camptothecin conjugate, e.g., CRLX101, or a CDP-inhibitor conjugate described herein. The mixture is maintained under conditions to precipitate at least a portion of the CDP-inhibitor conjugate, e.g., CDP-camptothecin conjugate, e.g., CRLX101, or a CDP-inhibitor conjugate described herein, from the mixture, thereby precipitating at least a portion of the polymer. The precipitated CDP-inhibitor conjugate, e.g., CDP-camptothecin conjugate, e.g., CRLX101, or a CDP-inhibitor conjugate described herein, can be filtered to separate the precipitated CDP-inhibitor conjugate, e.g., CDP-camptothecin conjugate, e.g., CRLX101, or a CDP-inhibitor conjugate described herein, from the mixture.

The CDP-inhibitor conjugate, e.g., CDP-camptothecin conjugate, e.g., CRLX101, or a CDP-inhibitor conjugate described herein, can be precipitated from a polymer-containing solution using a precipitation system as described herein. For example, the precipitation system can comprise a vessel for housing a cooled non-solvent, the vessel having at least one input port and an output port; a cooling system in communication with the vessel for cooling and maintaining the temperature of the cooled non-solvent; and a pump in communication with the vessel and configured to cause a flow of the cooled non-solvent through the vessel; wherein said input port is configured to allow introduction of the polymer-containing solution into the cooled non-solvent, thereby precipitating at least a portion of the CDP-inhibitor conjugate, e.g., CDP-camptothecin conjugate, e.g., CRLX101, or a CDP-inhibitor conjugate described herein, CDP-inhibitor conjugate, e.g., CDP-camptothecin conjugate, e.g., CRLX101, or a CDP-inhibitor conjugate described herein. The purity of the precipitated CDP-inhibitor conjugate, e.g., CDP-camptothecin conjugate, e.g., CRLX101, or a CDP-inhibitor conjugate described herein, can be determined using standard analytical methods. Methods for evaluating preparations of the CDP-inhibitor conjugate, e.g., CDP-camptothecin conjugate, e.g., CRLX101, or a CDP-inhibitor conjugate described herein, are also described herein.

The CDP-inhibitor conjugate, e.g., CDP-camptothecin conjugate, e.g., CRLX101, or a CDP-inhibitor conjugate described herein, and related preparations, which are precipitated by the methods described herein, can be further processed. For example, the CDP-inhibitor conjugate, e.g., CDP-camptothecin conjugate, e.g., CRLX101, or a CDP-inhibitor conjugate described herein, described herein can be incorporated into a particle (e.g., a nanoparticle). The resulting particle can be formulated into a pharmaceutical composition or dosage form, which can be administered to a subject (e.g., a subject in need thereof), for example in the treatment of a disorder as described herein.

In preferred embodiments, the inhibitor in the CDP-inhibitor conjugate, particle or composition is camptothecin or a camptothecin derivative. The term "camptothecin derivative", as used herein, includes camptothecin analogues and metabolites of camptothecin. For example, camptothecin derivatives can have the following structure:

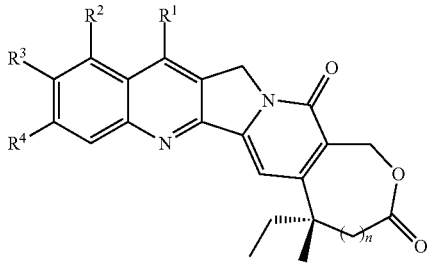

wherein
$R^1$ is H, OH, optionally substituted alkyl (e.g., optionally substituted with $NR^a_2$ or $OR_a$, or $SiR^a_3$), or $SiR^a_3$; or $R^1$ and $R^2$ may be taken together to form an optionally substituted 5- to 8-membered ring (e.g., optionally substituted with $NR^a_2$ or $OR^a$);
$R^2$ is H, OH, $NH_2$, halo, nitro, optionally substituted alkyl (e.g., optionally substituted with $NR^a_2$ or $OR^a$, $NR^a_2$, $OC(=O)NR^a_2$, or $OC(=O)OR^a$);
$R^3$ is H, OH, $NH_2$, halo, nitro, $NR^a_2$, $OC(=O)NR^a_2$, or $OC(=O)OR^a$
$R^4$ is H, OH, $NH_2$, halo, CN, or $NR^a_2$; or $R^3$ and $R^4$ taken together with the atoms to which they are attached form a 5- or 6-membered ring (e.g. forming a ring including —$OCH_2O$— or —$OCH_2CH_2O$—);

each $R^a$ is independently H or alkyl; or two $R^a$s, taken together with the atom to which they are attached, form a 4- to 8-membered ring (e.g., optionally containing an O or $NR^b$)

$R_b$ is H or optionally substituted alkyl (e.g., optionally substituted with $OR^c$ or $NR^c_2$);

$R^c$ is H or alkyl; or, two $R^c$s, taken together with the atom to which they are attached, form a 4- to 8-membered ring; and n=0 or 1.

In some embodiments, the camptothecin or camptothecin derivative is the compound as provided below.

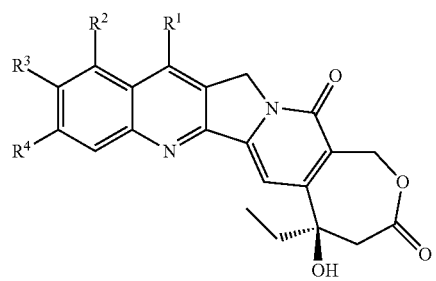

In one embodiment, $R^1$, $R^2$, $R^3$ and $R^4$ of the camptothecin derivative are each H, and n is 0.

In one embodiment, $R^1$, $R^2$, $R^3$ and $R^4$ of the camptothecin derivative are each H, and n is 1.

In one embodiment, $R^1$ of the camptothecin derivative is H, $R^2$ is —$CH_2N(CH_3)_2$, $R^3$ is —OH, $R^4$ is H; and n is 0.

In one embodiment, the camptothecin derivative is SN-38, or derivative thereof, having the following structure:

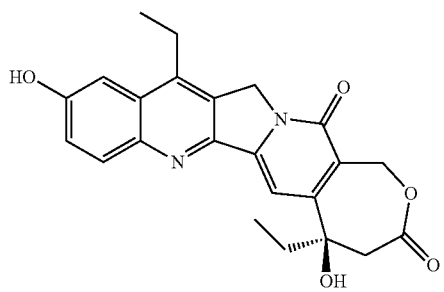 [SMILES: CCc1c2c(nc3ccc(O)cc13)-c1cc3c(c(=O)n1C2)COC(=O)C[C@]3(O)CC]

In one embodiment, $R^1$ of the camptothecin derivative is —$CH_2CH_3$, $R^2$ is H, $R^3$ is:

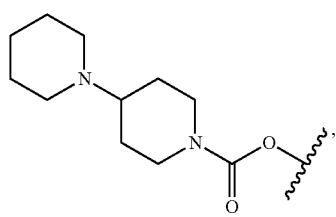 [SMILES: *OC(=O)N1CCC(N2CCCCC2)CC1]

$R^4$ is H, and n is 0.

In one embodiment, $R^1$ of the camptothecin derivative is —$CH_2CH_3$, $R^2$ is H, $R^3$ is —OH, $R^4$ is H, and n is 0.

In one embodiment, $R^1$ of the camptothecin derivative is tert-butyldimethylsilyl, $R^2$ is H, $R^3$ is —OH and $R^4$ is H, and n is 0.

In one embodiment, $R^1$ of the camptothecin derivative is tert-butyldimethylsilyl, $R^2$ is hydrogen, $R^3$ is —OH and $R^4$ is hydrogen, and n is 1.

In one embodiment, $R^1$ of the camptothecin derivative is tert-butyldimethylsilyl, $R^2$, $R^3$ and $R^4$ are each H, and n is 0.

In one embodiment, $R^1$ of the camptothecin derivative is tert-butyldimethylsilyl, $R^2$, $R^3$ and $R^4$ are each H, and n is 1.

In one embodiment, $R^1$ of the camptothecin derivative is —$CH_2CH_2Si(CH_3)_3$ and $R^2$, $R^3$ and $R^4$ are each H.

In one embodiment, $R^1$ and $R^2$ of the camptothecin derivative are taken together with the carbons to which they are attached to form an optionally substituted ring. In one embodiment, $R^1$ and $R^2$ of the camptothecin derivative are taken together with the carbons to which they are attached to form a substituted 6-membered ring. In one embodiment, the camptothecin derivative has the following formula:

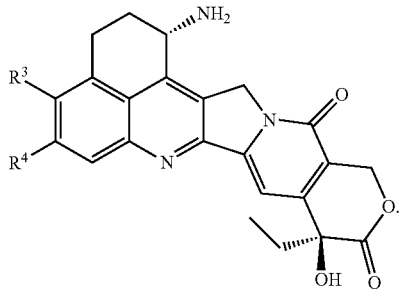

In one embodiment, $R^3$ is methyl and $R^4$ is fluoro.

In one embodiment, $R^3$ and $R^4$ are taken together with the carbons to which they are attached to form an optionally substituted ring. In one embodiment, $R^3$ and $R^4$ are taken together with the carbons to which they are attached to form a 6-membered heterocyclic ring. In one embodiment, the camptothecin derivative has the following formula:

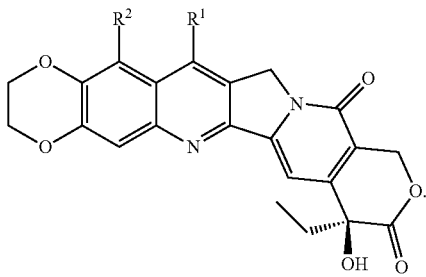

In one embodiment, $R^1$ is:

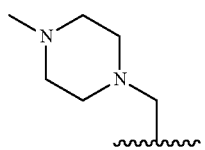 [SMILES: *CN1CCN(C)CC1]

and $R^2$ is hydrogen.

In one embodiment, the camptothecin derivative has the following formula:

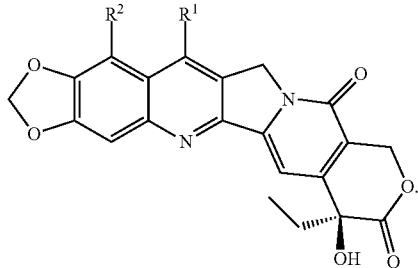

In one embodiment, $R^1$ is:

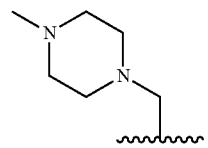

and $R^2$ is hydrogen.

In one embodiment, $R^1$ is:

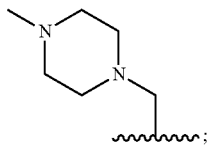 [SMILES: *CN1CCN(C)CC1]

$R^2$ is H, $R^3$ is methyl, $R^4$ is chloro; and n is 1.

In one embodiment, $R^1$ is —$CH=NOC(CH_3)_3$, $R^2$, $R^3$ and $R^4$ are each H, and n is 0.

In one embodiment, $R^1$ is —$CH_2CH_2NHCH(CH_3)_2$, $R^2$, $R^3$ and $R^4$ are each H; and n is 0.

In one embodiment, $R^1$ and $R^2$ are H, $R^3$ and $R^4$ are fluoro, and n is 1.

In one embodiment, each of $R^1$, $R^3$, and $R^4$ is H, $R^2$ is $NH_2$, and n is 0.

In one embodiment, each of $R^1$, $R^3$, and $R^4$ is H, $R^2$ is $NO_2$, and n is 0.

Definitions

The term "precipitate," as used herein, refers to the separation of a solid substance, e.g., a CDP-inhibitor conjugate, e.g., CDP-camptothecin conjugate, e.g., CRLX101, or a CDP-inhibitor conjugate described herein, from a mixture, e.g., a solution, dispersion, or a mixed solution/dispersion, of that solid substance and a liquid. The term "precipitation" refers to the act of precipitating.

The term "separate" or "separating," as used herein, is defined as increasing the amount of a first component, e.g., a CDP-inhibitor conjugate, e.g., CDP-camptothecin conjugate, e.g., CRLX101, or a CDP-inhibitor conjugate described herein, relative to the amounts of at least one, and in embodiments, more than one, other component, e.g., a contaminant, in a mixture, e.g., a mixture comprising one or more of a non-solvent, a polymer-containing solution, a process solvent. In some embodiments, the precipitated CDP-inhibitor conjugate, e.g., CDP-camptothecin conjugate, e.g., CRLX101, or a CDP-inhibitor conjugate described herein, is separated from the liquid component of a mixture, e.g., a mixture comprising a non-solvent, a process solvent, unreacted starting materials, e.g., from the conjugation reaction of a polymer, e.g., a CDP, with a therapeutic agent, e.g., a camptothecin or camptothecin conjugate, such as CRLX101. After separation of the precipitated CDP-inhibitor conjugate, e.g., CDP-camptothecin conjugate, e.g., CRLX101, or a CDP-inhibitor conjugate described herein, the amount of the precipitated CDP-inhibitor conjugate, e.g., CDP-camptothecin conjugate, e.g., CRLX101, or a CDP-inhibitor conjugate described herein, is substantially increased relative to the amount of at least one, and in embodiments, more than one, of the other components of the mixture. In some embodiments, the separated precipitated CDP-inhibitor conjugate, e.g., CDP-camptothecin conjugate, e.g., CRLX101, or a CDP-inhibitor conjugate described herein, contains less than 20, 10, 5, 1, 0.5%, or 0.1%, by dry weight, of a component of the mixture, e.g., contaminant, e.g., non-solvent, process solvent, polymer-containing solution, an unreacted starting material, and other conjugation reaction side products. In some embodiments, the separated precipitated polymer conjugate is substantially free, by dry weight analysis, of a component of the mixture, e.g., contaminant, e.g., non-solvent, process solvent, polymer-containing solution, an unreacted starting material, and other conjugation reaction side products.

The term "polymer-containing solution," as used herein, refers to a solution in which a polymer is disposed, e.g., in the form of a polymer solution, dispersion, or mixed solution/dispersion. In some embodiments, the polymer-containing solution comprises a reaction mixture, e.g., from a conjugation reaction between a polymer, e.g., a polymer comprising cyclodextrin, e.g., beta-cyclodextrin, and an inhibitor, e.g., a camptothecin or camptothecin derivative, such as CRLX101, or a CDP-inhibitor conjugate described herein.

In some embodiments, the polymer-containing solution comprises the CDP-inhibitor conjugate, e.g., CDP-camptothecin conjugate, e.g., CRLX101, or a CDP-inhibitor conjugate described herein. In some embodiments, the polymer-containing solution comprises an unconjugated polymer, e.g., a CDP that did not conjugate with an inhibitor, e.g., camptothecin or camptothecin derivative, during the conjugation reaction. In some embodiments, the unconjugated polymer, e.g., CDP, can be a polymer that comprises a reactive group, which can include a hydroxyl moiety, a thiol moiety, an amine moiety, a carboxylic acid moiety, or an activated ester moiety.

In some embodiments, the polymer-containing solution comprises a process solvent, e.g., a solvent present in the reaction mixture, e.g., conjugation reaction mixture. The term "process solvent" as used herein refers to a solvent that acts to keep the reactants of a reaction mixture, e.g., conjugation reaction, soluble. In some embodiments, the polymer is typically sufficiently soluble in the solvent such that a concentration of at least about 0.1 percent by weight, and preferably at least about 0.2 percent by weight, of the polymer, e.g., CDP, can be dissolved in the solvent at room temperature.

The term "about" or "approximately," as used herein, refers to within an acceptable error range for the particular value as determined by one of ordinary skill in the art, which will depend in part on how the value is measured or determined, e.g., the limitations of the measurement system, or the degree of precision required for a particular purpose. For example, "about" can mean within 1 or more than 1 standard deviations, as per the practice in the art. Alternatively, "about" can mean a range of up to 20%, up to 10%, up to 5%, and up to 1% of a given value. Where particular values are described in the application and claims, unless otherwise stated, the term "about" meaning within an acceptable error range for the particular value should be assumed.

The term "non-solvent" as used herein refers to a liquid, or a mixture of liquids, which is incapable of dissolving any appreciable concentration (e.g., a concentration less than about 5%, less than about 2%, less than about 1%, less than about 0.5%, less than about 0.2%, less than about 0.1% at room temperature) of a polymer of interest, e.g., the CDP-inhibitor conjugate, e.g., CDP-camptothecin conjugate, e.g., CRLX101, or a CDP-inhibitor conjugate described herein. In some embodiments, the non-solvent can be cooled so as to lower the concentration of the dissolution of the polymer of interest, e.g., the CDP-inhibitor conjugate, e.g., CDP-camptothecin conjugate, e.g., CRLX101, or a CDP-inhibitor conjugate described herein, in the non-solvent. For example, the non-solvent can be cooled to a temperature of about 0° C. to about −100° C., e.g., about −10° C. to about −90° C., about −20° C. to about −80° C. In some embodiments, the non-solvent can be cooled to a temperature of −78° C.

The term "ambient conditions," as used herein, refers to surrounding conditions at about one atmosphere of pressure, 50% relative humidity and about 25° C., unless specified as otherwise.

The term "attach," or "attached," as used herein, with respect to the relationship of a first moiety to a second moiety, e.g., the attachment of an agent to a polymer, refers to the formation of a covalent bond between a first moiety and a second moiety. In the same context, the noun "attachment" refers to a covalent bond between the first and second moiety. For example, a therapeutic agent, e.g., topoisomerase inhibitor, e.g., camptothecin or camptothecin derivative, can be covalently bonded to the polymer, e.g., cyclodextrin, e.g., beta-cyclodextrin polymer (CDP). The attachment can be a direct attachment, e.g., through a direct bond of the first moiety to the second moiety, or can be through a linker (e.g., through a covalently linked chain of one or more atoms disposed between the first and second moiety). For example, where an attachment is through a linker, a first moiety (e.g., a therapeutic agent, such as camptothecin or camptothecin derivative) is covalently bonded to a linker, which in turn is covalently bonded to a second moiety.

The term "biodegradable" includes polymers, compositions and formulations, such as those described herein, that are intended to degrade during use. Biodegradable polymers typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to a side chain or that connects a side chain to the polymer backbone. In certain embodiments, one or the other or both general types of biodegradation can occur during use of a polymer.

The term "biodegradation," as used herein, encompasses both general types of biodegradation described above. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of a polymer, assembly of polymers or particle, and the mode and location of administration. For example, a greater molecular weight, a higher degree of crystallinity, and/or a greater biostability, usually lead to slower biodegradation.

The phrase "cleavable under physiological conditions" refers to a bond having a half life of less than about 50 or 100 hours, when subjected to physiological conditions. For example, enzymatic degradation can occur over a period of less than about five years, one year, six months, three months, one month, fifteen days, five days, three days, or one day upon exposure to physiological conditions (e.g., an aqueous solution having a pH from about 4 to about 8, and a temperature from about 25° C. to about 37° C.

The term "contaminant," as used herein, is a compound other than the CDP-inhibitor conjugate, e.g., CDP-camptothecin conjugate, e.g., CRLX101, or a CDP-inhibitor conjugate described herein. A contaminant can be an unconjugated component or starting material in the mixture, e.g., conjugation reaction mixture. A contaminant can be a product of the conjugation reaction other than the CDP-inhibitor conjugate, e.g., CDP-camptothecin conjugate, e.g., CRLX101, or a CDP-inhibitor conjugate described herein, such as an unconjugated therapeutic agent, e.g., unconjugated inhibitor, e.g., camptothecin or camptothecin derivative, unconjugated polymer, e.g., unconjugated CDP, process solvent, or conjugation reaction side products.

In some embodiments, the contaminant can be an unconjugated inhibitor. In some embodiments, the contaminant can be a glycine-derivatized camptothecin (CPT-glycine) that failed to conjugate with the polymer, e.g., CDP.

In some embodiments, the contaminant can be an unconjugated polymer, e.g., CDP. In some embodiments, the unconjugated polymer, e.g., CDP, can include a hydroxyl, a thiol moiety, an amine moiety, or a carboxylic acid moiety. In some embodiments, the unconjugated polymer can have a molecular weight of about 5 kDa to about 200 kDa.

In some embodiments, the contaminant can be any of the reagents used in the conjugation reaction between an inhibitor, e.g., camptothecin, and a polymer, e.g., a CDP. For example, the contaminant can be a carbodiimide, e.g., N,N'-dicyclohexylcarbodiimide (DCC), N,N'-Diisopropylcarbodiimide (DIC), and (1-Ethyl-3-(3-dimethyllaminopropyl) carbodiimide (EDC). Other contaminants include, but are not limited to, hydroxysuccinimide (NHS), diethylamine, and triethylamine.

In some embodiments, the contaminant is a process solvent such as water, dimethylsulfoxide (DMSO), N,N-dimethylformamide (DMF), or acetonitrile.

An "effective amount" or "an amount effective" refers to an amount of the CDP-inhibitor conjugate, e.g., CDP-camptothecin conjugate, e.g., CRLX101, or a CDP-inhibitor conjugate described herein, particle, or composition which is effective, upon single or multiple dose administrations to a subject, in treating a cell, or curing, alleviating, relieving or improving a symptom of a disorder. An effective amount of the composition may vary according to factors such as the disease state, age, sex, and weight of the individual, and the ability of the compound to elicit a desired response in the individual. An effective amount is also one in which any toxic or detrimental effects of the composition are outweighed by the therapeutically beneficial effects.

"Pharmaceutically acceptable carrier or adjuvant," as used herein, refers to a carrier or adjuvant that may be administered to a patient, together with a CDP-inhibitor conjugate, e.g., CDP-camptothecin conjugate, e.g., CRLX101, or a CDP-inhibitor conjugate described herein, described herein, and which does not destroy the pharmacological activity thereof and is nontoxic when administered in doses sufficient to deliver a therapeutic amount of the particle. Some examples of materials which can serve as pharmaceutically acceptable carriers include: (1) sugars, such as lactose, glucose, mannitol and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions.

The term "polymer," as used herein, is given its ordinary meaning as used in the art, i.e., a molecular structure featuring one or more repeat units (monomers), connected by covalent bonds. The repeat units may all be identical, or in some cases, there may be more than one type of repeat unit present within the polymer. In some cases, the polymer is biologically derived, i.e., a biopolymer. Non-limiting examples of biopolymers include peptides or proteins (i.e., polymers of various amino acids), or nucleic acids such as DNA or RNA. In some instances, a polymer may be comprised of subunits, e.g., a subunit described herein, wherein a subunit comprises polymers, e.g., PEG, but the subunit may be repeated within a conjugate. In some embodiments, a conjugate may comprise only one subunit described herein; however conjugates may comprise more than one identical subunit.

As used herein the term "low aqueous solubility" refers to water insoluble compounds having poor solubility in water, that is <5 mg/ml at physiological pH (6.5-7.4). Preferably, their water solubility is <1 mg/ml, more preferably <0.1 mg/ml. It is desirable that the drug is stable in water as a dispersion; otherwise a lyophilized or spray-dried solid form may be desirable.

A "hydroxy protecting group" as used herein, is well known in the art and includes those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable hydroxy protecting groups include, for example, acyl (e.g., acetyl), triethylsilyl (TES), t-butyldimethylsilyl (TBDMS), 2,2,2-trichloroethoxycarbonyl (Troc), and carbobenzyloxy (Cbz).

"Inert atmosphere" or "inert environment," as used herein, refers to an atmosphere composed primarily of an inert gas, which does not chemically react with the CDP-inhibitor conjugate, e.g., CDP-camptothecin conjugate, e.g., CRLX101, or a CDP-inhibitor conjugate described herein, particles, compositions or mixtures described herein. Examples of inert gases are nitrogen ($N_2$), helium, and argon.

"Linker," as used herein, is a moiety having at least two functional groups. One functional group is capable of reacting with a functional group on a CDP-inhibitor conjugate, e.g., CDP-camptothecin conjugate, e.g., CRLX101, or a CDP-inhibitor conjugate described herein, and a second functional group is capable of reacting with a functional group on agent described herein. In some embodiments, the linker has just two functional groups. A linker may have more than two functional groups (e.g., 3, 4, 5, 6, 7, 8, 9, 10 or more functional groups), which may be used, e.g., to link multiple agents to a polymer. Depending on the context, linker can refer to a linker moiety before attachment to either of a first or second moiety (e.g., agent or polymer), after attachment to one moiety but before attachment to a second moiety, or the residue of the linker present after attachment to both the first and second moiety.

The term "lyoprotectant," as used herein refers to a substance present in a lyophilized preparation. Typically it is present prior to the lyophilization process and persists in the resulting lyophilized preparation. It can be used to protect nanoparticles, liposomes, and/or micelles during lyophilization, for example to reduce or prevent aggregation, particle collapse and/or other types of damage. In an embodiment the lyoprotectant is a cryoprotectant. In an embodiment the lyoprotectant is a carbohydrate.

As used herein, the term "prevent" or "preventing" as used in the context of the administration of an agent to a subject, refers to subjecting the subject to a regimen, e.g., the administration of a CDP-inhibitor conjugate, e.g., CDP-camptothecin conjugate, e.g., CRLX101, or a CDP-inhibitor conjugate described herein, such that the onset of at least one symptom of the disorder is delayed as compared to what would be seen in the absence of the regimen.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The term "nanoparticle" is used herein to refer to a material structure whose size in any dimension (e.g., x, y, and z Cartesian dimensions) is less than about 1 micrometer (micron), e.g., less than about 500 nm or less than about 200 nm or less than about 100 nm, and greater than about 5 nm. A nanoparticle can have a variety of geometrical shapes, e.g., spherical, ellipsoidal, etc. The term "nanoparticles" is used as the plural of the term "nanoparticle."

The term "average particle size," as used herein with respect to polymeric particles, is a length dimension which is designated herein as Z average or $Z_{ave}$, and as used herein refers to the intensity weighted mean hydrodynamic size of an ensemble collection of particles measured by dynamic light scattering (DLS). The Z average is derived from a Cumulants analysis of a measured autocorrelation curve, wherein a single particle size is assumed and a single exponential fit is applied to the autocorrelation function. The autocorrelation function ($G(\tau)$) is defined as follows:

$$G(\tau) = \langle I(t) \cdot I(t+\tau) \rangle = A[1 + B\exp(-2\Gamma\tau)] \quad \text{Eq. (3)}$$

wherein, $$\Gamma = Dq^2 \quad \text{Eq. (4)}$$

$$q = \frac{4\pi\tilde{n}}{\lambda_0}\sin\left(\frac{\theta}{2}\right) \quad \text{Eq. (5)}$$

$$D = \frac{kT}{6\pi\mu R_H}, \quad \text{Eq. (6)}$$

wherein,
I represents the light scattering intensity,
t represents an initial time,
$\tau$ represents the delay time,
A represents an amplitude (or intercept) of the autocorrelation function,
B represents the baseline,
D represents the diffusion coefficient,
q represents the scattering vector,
k represents the Boltzmann constant,
$\lambda_0$ represents the vacuum wavelength of a laser source employed for the light scattering measurements,
$\tilde{n}$ represents the index of refraction of the medium,
$\theta$ represents the scattering angle,
T represents the absolute temperature (Kelvin),
$\mu$ represents the viscosity of the medium, and
$R_H$ represents the hydrodynamic radius.

In the Cumulants analysis, the exponential fitting expression of Eq. (3) is expanded as indicated below as expression $y(\tau)$ in Eq. (7) to account for polydispersity, which is defined in more detail below, or peak broadening, $$\begin{aligned} y(\tau) &= \frac{1}{2}\ln[G(\tau) - A] \\ &= \frac{1}{2}\ln[AB\exp(-2\Gamma\tau + \mu_2\tau^2)] \\ &\cong \frac{1}{2}\ln[AB] - \langle\Gamma\rangle\tau + \frac{\mu_2}{2}\tau^2 \\ &= a_0 - a_1\tau + a_2\tau^2 \end{aligned} \quad \text{Eq. (7)}$$

wherein $\mu_2$ is a fitting parameter and the other parameters are defined above.

The dynamic light scattering data can be fit to the above expression (Eq. (7)) to obtain values of the parameters $a_0$, $a_1$, and $a_2$. The first Cumulant moment ($a_1$) can be utilized to obtain $Z_{ave}$ as follows:

$$Z_{ave} = \frac{1}{a_1}\frac{kT}{3\pi\mu}\left[\frac{4\pi\tilde{n}}{\lambda_0}\sin\left(\frac{\theta}{2}\right)\right]^2 \quad \text{Eq. (8)}$$

wherein the parameters are defined above.

The first Cumulant moment ($a_1$) and the second Cumulant moment ($a_2$) can be used to calculate another parameter known as polydispersity index (PdI), which is discussed in more detail below, as follows:

$$PdI = \frac{2a_2}{a_1^2} \quad \text{Eq. (9)}$$

The term "polydispersity index" is used herein as a measure of the size distribution of an ensemble of particles, e.g., nanoparticles. The polydispersity index is calculated as indicated in the above Eq. (9) based on dynamic light scattering measurements.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents). Exemplary acyl groups include acetyl ($CH_3C(O)$—), benzoyl ($C_6H_5C(O)$—), and acetylamino acids (e.g., acetylglycine, $CH_3C(O)NHCH_2C(O)$—).

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer, and most preferably 10 or fewer. Likewise, preferred cycloalkyls have from 3-10 carbon atoms in their ring structure, and more preferably have 5, 6 or 7 carbons in the ring structure. The term "alkylenyl" refers to a divalent alkyl, e.g., —$CH_2$—, —$CH_2CH_2$—, and —$CH_2CH_2CH_2$—.

The term "alkenyl" refers to an aliphatic group containing at least one double bond. The terms "alkoxyl" or "alkoxy" refers to an alkyl group, as defined below, having an oxygen radical attached thereto. Representative alkoxyl groups include methoxy, ethoxy, propyloxy, tert-butoxy and the like. An "ether" is two hydrocarbons covalently linked by an oxygen.

The term "alkynyl" refers to an aliphatic group containing at least one triple bond. The term "aralkyl" or "arylalkyl" refers to an alkyl group substituted with an aryl group (e.g., a phenyl or naphthyl).

The term "aryl" includes 5-14 membered single-ring or bicyclic aromatic groups, for example, benzene, naphthalene, and the like. The aromatic ring can be substituted at one or more ring positions with such substituents as described above, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties,—$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls. Each ring can contain, e.g., 5-7 members. The term "arylene" refers to a divalent aryl, as defined herein.

The term "carboxy" refers to a —C(O)OH or salt thereof.

The term "hydroxy" and "hydroxyl" are used interchangeably and refer to —OH. The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Any atom can be substituted. Suitable substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The terms "halo" and "halogen" means halogen and includes chloro, fluoro, bromo, and iodo.

The terms "hetaralkyl", "heteroaralkyl" or "heteroarylalkyl" refers to an alkyl group substituted with a heteroaryl group.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylene" refers to a divalent heteroaryl, as defined herein.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Nitro" refers to the —NO$_2$ radical.

Methods of Precipitating Polymer Conjugates

Methods for precipitating CDP-inhibitor conjugate, e.g., CDP-camptothecin conjugate, e.g., CRLX101, or a CDP-inhibitor conjugate described herein, from a polymer-containing solution are described herein. Methods described herein comprise providing a vessel housing a volume of a cooled non-solvent; agitating the cooled non-solvent; introducing the polymer-containing solution into the cooled non-solvent to form a mixture comprising a liquid and CDP-inhibitor conjugate, e.g., CDP-camptothecin conjugate, e.g., CRLX101, or a CDP-inhibitor conjugate described herein; and maintaining the mixture under conditions to precipitate at least a portion of the CDP-inhibitor conjugate, e.g., CDP-camptothecin conjugate, e.g., CRLX101, or a CDP-inhibitor conjugate described herein, from the mixture, thereby precipitating at least a portion of the CDP-inhibitor conjugate, e.g., CDP-camptothecin conjugate, e.g., CRLX101, or a CDP-inhibitor conjugate described herein.

With reference to the flow chart of FIG. 1, in one embodiment, a vessel is provided that houses a volume of a cooled non-solvent (Step 1). A polymer-containing solution is introduced into the vessel to form a mixture comprising a liquid and a CDP-inhibitor conjugate, e.g., CDP-camptothecin conjugate, e.g., CRLX101, or a CDP-inhibitor conjugate described herein; and maintaining the mixture under conditions to precipitate at least a portion of the CDP-inhibitor conjugate, e.g., CDP-camptothecin conjugate, e.g., CRLX101, or a CDP-inhibitor conjugate described herein, from the mixture, thereby precipitating at least a portion of the CDP-inhibitor conjugate, e.g., CDP-camptothecin conjugate, e.g., CRLX101, or a CDP-inhibitor conjugate described herein (Step 2). In some embodiments, the polymer-containing solution comprises one or more of a CDP-inhibitor conjugate, e.g., CDP-camptothecin conjugate, e.g., CRLX101, or a CDP-inhibitor conjugate described herein, an unconjugated inhibitor, e.g., an unconjugated camptothecin or camptothecin derivative, an unconjugated polymer, e.g., unconjugated CDP, a conjugation reaction side product, and a process solvent.

In some embodiments, the non-solvent comprises any of a solvent or a mixture of two or more solvents. The solvents can be either organic or inorganic solvents. By way of example, the non-solvent can include any of acetone, methanol, ethanol, n-propanol, isopropanol, n-butanol, and ethyl ether, methyl isobutyl ketone (MIBK), ethyl acetate (ETAC), water, among others.

In some embodiments, the non-solvent comprises acetone. In some embodiments, the acetone comprises less than 20% by volume of water, less than 15% by volume of water, less than 10% by volume of water, less than 5% by volume of water, less than 2% by volume of water, less than 1% by volume of water, less than 0.5% by volume of water, or less than 0.1% by volume of water.

In some embodiments, the vessel can be a 5 mL, 10 mL, 50 mL, 100 mL, 250 mL, 500 mL, 1 liter, or 2 liter glass beaker. In some embodiments, the vessel can be a 5 liter, 10 liter, 25 liter, 50 liter reactor used in a scale up process. The vessel housing the non-solvent can be cooled and maintained at a constant temperature throughout the precipitation process. In some embodiments, the non-solvent is cooled before the polymer-containing solution is introduced into the vessel. For example, the vessel housing the non-solvent can be cooled and maintained at a temperature of about 0° C. to about −100° C., e.g., about −10° C. to about −90° C., about −20° C. to about −80° C. In some embodiments, the vessel is cooled and maintained at a temperature of −78° C.

In some embodiments, the process further includes extracting at least a portion of the liquid comprising the polymer-containing solution and the non-solvent from the vessel and recirculating the liquid through the vessel to induce further precipitation of the CDP-inhibitor conjugate, e.g., CDP-camptothecin conjugate, e.g., CRLX101, or a CDP-inhibitor conjugate described herein (Step 3).

In some embodiments, the CDP-inhibitor conjugate, e.g., CDP-camptothecin conjugate, e.g., CRLX101, or a CDP-inhibitor conjugate described herein, is immiscible, or at least exhibits low miscibility in the non-solvent. For example, in some embodiments, the miscibility of the CDP-inhibitor conjugate, e.g., CDP-camptothecin conjugate, e.g., CRLX101, or a CDP-inhibitor conjugate described herein, in the non-solvent is less than about 0.5% at −78° C. (e.g., at 25° C.). In some embodiments, the process solvent is miscible, or at least partially miscible, with the non-solvent.

Without wishing to be bound by theory, as the polymer-containing solution flows into the vessel and comes into contact with the cooled non-solvent, the polymer-containing solution can diffuse into the non-solvent due to its miscibility with the non-solvent. The CDP-inhibitor conjugate, e.g., CDP-camptothecin conjugate, e.g., CRLX101, or a CDP-inhibitor conjugate described herein, is not miscible, or exhibits low miscibility, with the non-solvent, and hence precipitates out of solution. Such precipitation of the CDP-inhibitor conjugate, e.g., CDP-camptothecin conjugate, e.g., CRLX101, or a CDP-inhibitor conjugate described herein, in the cooled non-solvent continues as fresh polymer-containing solution is introduced into the vessel. As noted above, optionally, in some embodiments, a portion of the liquid in the vessel can be extracted and recirculated back to the vessel for precipitating at least a second portion of the CDP-inhibitor conjugate, e.g., CDP-camptothecin conjugate, e.g., CRLX101, or a CDP-inhibitor conjugate described herein, which is contained in the extracted liquid, in the cooled non-solvent.

Referring again to the flow chart of FIG. 1, in some embodiments, after the introduction of the polymer-containing solution into the vessel is terminated; a second volume of cooled non-solvent is added to the vessel (Step 4).

Referring again to the flow chart of FIG. 1, in some embodiments, the precipitated CDP-inhibitor conjugate, e.g., CDP-camptothecin conjugate, e.g., CRLX101, or a CDP-inhibitor conjugate described herein, can be optionally collected, e.g., via filtration (Step 5). Alternatively, the CDP-inhibitor conjugate, e.g., CDP-camptothecin conjugate, e.g., CRLX101, or a CDP-inhibitor conjugate described herein, can be separated from the liquid via centrifugation.

In some embodiments, the collected CDP-inhibitor conjugate, e.g., CDP-camptothecin conjugate, e.g., CRLX101, or a CDP-inhibitor conjugate described herein, can be optionally dried, e.g., by utilizing a vacuum or a flow of a gas such as dry nitrogen or argon, to remove at least a portion of residual liquid present in the particles (Step 6). Otherwise, the CDP-inhibitor conjugate, e.g., CDP-camptothecin conjugate, e.g., CRLX101, or a CDP-inhibitor conjugate described herein, can be filtered using the cooled non-solvent and then stored in the non-solvent, either at room temperature or at a lower temperature, e.g., less than about 0° C., less than about −10° C., less than about −20° C., less than about −30° C., less than about −40° C., less than about −50° C., less than about −60° C., less than about −70° C., less than about −80° C.

In some embodiments, the precipitated CDP-inhibitor conjugate, e.g., CDP-camptothecin conjugate, e.g., CRLX101, or a CDP-inhibitor conjugate described herein, can be dried using a vacuum or inert gas such as nitrogen or argon, and then stored dry under vacuum or an inert atmosphere in a solid form, e.g., as flakes or shards. Alternatively, the precipitated CDP-inhibitor conjugate, e.g., CDP-camptothecin conjugate, e.g., CRLX101, or a CDP-inhibitor conjugate described herein, can be filtered and washed with cooled non-solvent and stored using the non-solvent, in a solid form, e.g., as flakes or shards, either at room temperature or at a lower temperature. The CDP-inhibitor conjugate, e.g., CDP-camptothecin conjugate, e.g., CRLX101, or a CDP-inhibitor conjugate described herein, can be stored at a lower temperature, e.g., less than about 0° C., less than about −10° C., less than about −20° C., less than about −30° C., less than about −40° C., less than about −50° C., less than about −60° C., less than about −70° C., less than about −80° C., refrigerated or frozen, for later use (Step 7). In some embodiments, the CDP-inhibitor conjugate, e.g., CDP-camptothecin conjugate, e.g., CRLX101, or a CDP-inhibitor conjugate described herein, can be subsequently exposed to a liquid, a polar protic solvent, such as water, to form particles, e.g., nanoparticles.

In a further embodiment, a lyoprotectant can be optionally added to the particles, e.g., nanoparticles, to protect the particles, e.g., nanoparticles, from damage and/or to retard permanent aggregation of the particles, e.g., nanoparticles, when subsequently subjected to lyophilization. The lyoprotectant can also facilitate the resuspension of the particles, e.g., nanoparticles. Some examples of suitable lyoprotectants include, without limitation, conventional lyoprotectants, e.g., mannitol, lactose, trehalose, sucrose, or a derivatized cyclic oligosaccharide, e.g., a derivatized cyclodextrin, e.g., 2 hydroxy propyl-β cyclodextrin, e.g., partially etherified cyclodextrins (e.g., partially etherified β cyclodextrins) disclosed in U.S. Pat. No. 6,407,079, the contents of which are incorporated herein by this reference.

In some embodiments, the particles, e.g., nanoparticles, and the lyoprotectant can then be optionally stored in one or more suitable vessels, e.g., vials, and lyophilized in a manner known in the art. The vials can then be sealed to protect the particles, e.g., nanoparticles, from contamination. For example, the lyophilization can be achieved by initially freezing the particles, e.g., nanoparticles, followed by a primary drying phase in which the ambient pressure to which the concentrated suspension is subjected is lowered (e.g., to a few millibars) while supplying enough heat to cause sublimation of bulk frozen liquid, mostly frozen water in many implementations at this stage. In a secondary drying phase, bound liquid (e.g., water molecules bound to product or lyoprotectant), if any, can be removed by raising the temperature above that in the primary. In some embodiments, upon completion of the freeze-drying process, an inert gas, such as nitrogen, can be introduced into the vessel containing the lyophilized particles, e.g., nanoparticles, prior to sealing the vessel.

In some embodiments, the particles, e.g., nanoparticles, prepared according to the methods described herein can exhibit an average particle size equal to or less than about 1 micron. For example, the polymeric nanoparticle can exhibit an average particle size equal or less than about 500 nm. For example, the polymeric nanoparticles can exhibit an average particle size in a range of about 5 nm to about 500 nm, or in a range of about 10 nm to about 500 nm, or in a range of about 20 nm to about 500 nm, or in a range of about 30 nm to about 500 nm, or in a range of about 40 nm to about 500 nm, or in a range of about 50 nm to about 500 nm.

In some embodiments, the particles, e.g., nanoparticles, prepared according to the methods described herein can exhibit an average particle size equal to or less than about 400 nm. For example, the polymeric nanoparticles can exhibit an average particle size in a range of about 5 nm to about 400 nm, or in a range of about 10 nm to about 400 nm, or in a range of about 20 nm to about 400 nm, or in a range of about 30 nm to about 400 nm, or in a range of about 40 nm to about 400 nm, in a range of about 50 nm to about 400 nm.

In some embodiments, the particles, e.g., nanoparticles, prepared according to the methods described herein can exhibit an average particle size equal to or less than about 300 nm. For example, the polymeric nanoparticles can exhibit an average particle size in range of about 5 nm to about 300 nm, or in a range of about 10 nm to about 300 nm, or in a range of about 20 nm to about 300 nm, or in a range of about 30 nm to about 300 nm, or in a range of about 40 nm to about 300 nm, or in a range of about 50 nm to about 300 nm.

In some embodiments, the particles, e.g., nanoparticles, prepared according to the methods described herein can exhibit an average particle size equal to or less than about 200 nm. For example, the particles, e.g., nanoparticles, can exhibit an average particle size in a range of about 5 nm to about 200 nm, or in a range of about 10 nm to about 200 nm, or in a range of 20 nm to about 200 nm, or in a range of about 30 nm to about 200 nm, or in a range of about 40 nm to about 200 nm, or in a range of about 50 nm to about 200 nm.

In some embodiments, the particles, e.g., nanoparticles, prepared according to the methods described herein can exhibit an average particle size equal to or less than about 100 nm. For example, the nanoparticles can exhibit an average particle size in a range of about of 5 nm to about 100 nm, or in a range of about 10 nm to about 100 nm, or in a range of about 20 nm to about 100 nm, or in a range of about 30 nm to about 100 nm, or in a range of about 40 nm to about 100 nm, or in a range of about 50 nm to about 100 nm.

Systems for Precipitating a Polymer

The methods described herein for precipitating a CDP-inhibitor conjugate, e.g., CDP-camptothecin conjugate, e.g., CRLX101, or a CDP-inhibitor conjugate described herein, from a polymer-containing solution and/or generating particles, e.g., nanoparticles, can be performed using a system as described in FIG. 2. For example, FIG. 2 schematically depicts a system 10, which includes a vessel 12 for housing a cooled non-solvent. The vessel 12 includes an input port 16 for receiving a fluid and an output port 18 through which a fluid contained in the vessel can exit the vessel. The input and output ports 16 and 18 are in fluid communication via a loop fluid passage 20. In some embodiments, a recirculation pump (e.g., peristaltic or gear pump) 22 facilitates the flow of a fluid from the output port 18 of the vessel 12 to its input port 16. Further, a valve 24 disposed in the fluid loop 20 allows recovery of a product and/or waste from the vessel 12. The vessel 12 also includes a cooling jacket 13 in communication with the vessel 12 to cool the non-solvent, and also maintain the cooled temperature of the mixture in the vessel. The vessel 12 can optionally include a magnetic agitator 15 for mixing the contents of the vessel 12. In some embodiments, the vessel 12 can optionally include a mechanical agitator (not shown), such as an overhead stirrer, for mixing the contents of the vessel 12.

The system 10 further includes a reservoir 26 for storing a polymer-containing solution. The reservoir 26 includes an output port 28 that is in fluid communication with the input port 16 of the vessel 12 to allow the flow of the polymer-containing solution into the vessel 12. In some embodiments, the polymer-containing solution comprises an unconjugated polymer, e.g., an unconjugated CDP, e.g., a CDP that did not conjugate with an inhibitor, e.g., a camptothecin or camptothecin derivative, during the conjugation reaction. In some embodiments, the unconjugated polymer, e.g., the unconjugated CDP, can have a molecular weight of about 5 kDa to about 200 kDa. In some embodiments, the polymer-containing solution comprises an unconjugated inhibitor, e.g., an unconjugated camptothecin or camptothecin derivative, which did not conjugate with the polymer during the conjugation reaction. In some embodiments, the inhibitor, e.g., a camptothecin or camptothecin derivative, can be camptothecin modified with glycine, e.g., CPT-glycine. In some embodiments, the polymer-containing solution comprises one or more of the reagents utilized in the preparation of the CDP-inhibitor conjugate, e.g., CDP-camptothecin conjugate, e.g., CRLX101, or a CDP-inhibitor conjugate described herein. In some embodiments, the polymer-containing solution comprises unreacted polymer, e.g., unreacted CDP, e.g., CD-biscysteine. In some embodiments, the polymer-containing solution comprises CD-biscysteine copolymerized with PEG 3.4 kDa, e.g., PEG 3.4 kDa +/−10%. In some embodiments, the polymer-containing solution comprises one or more of an activated monomer, such as PEG-DiSBA. In some embodiments, the polymer-containing solution comprises a process solvent such as, one or more of acetone, ether, alcohol, tetrahydrofuran, 2-pyrrolidone, N-methyl-2-pyrrolidone, dimethylformamide, dimethylacetamide, methyl acetate, ethyl formate, methyl ethyl ketone, methyl isobutyl ketone, methyl propyl ketone, isopropyl ketone, isopropyl acetate, acetonitrile and dimethyl sulfoxide.

The exemplary system 10 further includes an additional reservoir 30. The reservoir 30 stores non-solvent. The reservoir 30 is in fluid communication with the input port 16 of the vessel 12 via its respective output port (shown here as output port 36) and a fluid passage 42. It should be understood that the number of reservoirs is not restricted to those disclosed herein and can be more than that illustrated. For example, in some embodiments, more than one reservoir may be employed, for storing two or more different non-solvents, e.g., reservoir 32.

In this exemplary implementation, the system 10 can further include a tangential flow filtration module 52 (e.g., a TFF module) that can be placed in fluid communication with vessel 12 for optional use, e.g., in concentrating a collection of particles (e.g., nanoparticles) generated in the vessel 12.

In some embodiments, in use, the vessel 12 is initially filled, or at least partially filled, with a quantity of a non-solvent, e.g., the non-solvent stored in the reservoir 30, by establishing a flow of the non-solvent from the non-solvent reservoir to the vessel 12. The cooling jacket is then activated to cool the non-solvent to the desired temperature, e.g., −50 to −100 degrees Celsius, e.g., −78 degrees Celsius. The cooled non-solvent can be agitated using the magnetic agitator 15. The pump 22 is then activated to establish a recirculating flow of the cooled non-solvent through the vessel 12 through a recirculation loop 20. Once the recirculating flow of the non-solvent is established, the polymer-containing solution stored in the reservoir 26 is injected into the vessel 12 to come into contact with the flowing cooled non-solvent. In some embodiments, a metering valve (not shown) at the output of the reservoir 26 is employed to control the rate of the flow of the polymer-containing solution into the flowing non-solvent.

As discussed above, the introduction of the polymer-containing solution into the recirculating non-solvent results in the precipitation of the inhibitor, e.g., a camptothecin or camptothecin derivative, e.g., CRLX101, in the cooled non-solvent housed in the vessel 12.

After a desired amount of the polymer-containing solution has been transferred to the vessel 12—typically after the exhaustion of the polymer-containing solution that is stored in the reservoir 26—the fluid connection between the reservoir 26 and the vessel 12 can be terminated and the liquid contained in the reaction vessel and recirculating loop 20 (which can contain a mixture of the non-solvent and the solution in which the inhibitor, e.g., a camptothecin or camptothecin derivative, e.g., CRLX101, was initially disposed) is drained via the valve 24.

Subsequently, the vessel 12 can be at least partially filled with the non-solvent stored in the reservoir 30 (non-solvent (1)) and the pump 22 can be activated to recirculate the resultant mixture comprising a liquid and the topoisomerase inhibitor, e.g., a camptothecin or camptothecin derivative, e.g., CRLX101, through the reaction vessel 12. The recirculating mixture can remove certain impurities that can be solubilized by the mixture. The recirculation of the mixture can continue for a desired time period after which the recirculation can be stopped, and the liquid in the reaction vessel and the recirculating loop can be drained, e.g., via the valve 24.

In some embodiments, after rinsing the precipitated inhibitor, e.g., a camptothecin or camptothecin derivative, e.g., CRLX101, with the cooled non-solvent the vessel 12 can be swept with dry nitrogen, or other suitable gas, to dry the precipitated inhibitor, e.g., a camptothecin or camptothecin derivative, e.g., CRLX101, and remove solvent residuals. The precipitated inhibitor, e.g., a camptothecin or camptothecin derivative, e.g., CRLX101, can be stored for later use, or alternatively it can be exposed to a solvent, such as water, supplied by reservoir 34, to generate particles, e.g., nanoparticles, in a suspension. The suspension of the particles, e.g., nanoparticles, in water can be optionally subjected to a filtration step for purification and concentration. The concentrated suspension of the particles, e.g., nanoparticles, can be optionally lyophilized and stored for later use.

For example, the aqueous suspension of the particles, e.g., nanoparticles, can be drained from the reaction vessel and routed through a second recirculating loop 44 using a plurality of control valves 46, 48, 50. In particular, the control valve 46 can be closed and the control valves 48 and 50 can be opened to route the aqueous suspension of the particles, e.g., nanoparticles, through the second recirculating loop 44 and through a tangential flow filter 52, where the suspension of particles, e.g., nanoparticles, is subjected to tangential flow filtration (TFF). For example, a recirculating flow of the particle suspension can be established between the vessel 12 and the TFF module 52, e.g., by shutting off valve 46, opening valves 48 and 50 and activating the pump 22. During diafiltration, a flow of a make-up fluid, e.g., water, stored in a reservoir 33 can be established from the reservoir 33 to the filtration module 52. The particle suspension enters the filtration module 52 via an input port 54. The retentate generated through the filtration process exits the TFF module via an output port 56 and is returned via a return fluid passage 58 to the reservoir 12. The filtrate is drained from the filtration module 52 via another output port 60 and associated valve 62. The filtration process continues for a desired time period, e.g., until a desired concentration of the particles, e.g., nanoparticles, in the vessel 12, is achieved. In some embodiments, the concentrated particles, e.g., nanoparticles, can then be collected and lyophilized for storage.

Methods of Analyzing the Precipitated Polymer Conjugates

The precipitated CDP-inhibitor conjugate, e.g., CDP-camptothecin conjugate, e.g., CRLX101, or a CDP-inhibitor conjugate described herein, prepared by the methods described herein can be analyzed for yield and purity using any of the following analytical methods that are known to those skilled in the art.

Spectrometric Analytical Methods

In some embodiments, precipitation methods described herein include the use of spectrometric analysis, to analyze the purity of the separated precipitated CDP-inhibitor conjugate, e.g., CDP-camptothecin conjugate, e.g., CRLX101, or a CDP-inhibitor conjugate described herein. Example spectrometric instruments that can be used to analyze the purity of the precipitated CDP-inhibitor conjugate, e.g., CDP-camptothecin conjugate, e.g., CRLX101, or a CDP-inhibitor conjugate described herein, include, but are not limited to, ultraviolet (UV) spectrometry, infrared spectrometry, proton nuclear magnetic resonance spectrometry ($^1$H-NMR), carbon-13 nuclear magnetic resonance spectrometry ($^{13}$C-NMR), correlation nuclear magnetic resonance spectrometry (2-D NMR), ultraviolet-visible spectrometry (UV-Vis), and mass spectrometry (MS). In some embodiments, the CDP-inhibitor conjugate, e.g., CDP-camptothecin conjugate, e.g., CRLX101, or a CDP-inhibitor conjugate described herein, can be detected using a wavelength of 434 nm, e.g., the emission wavelength of camptothecin.

In some embodiments, the desired precipitated CDP-inhibitor conjugate, e.g., CDP-camptothecin conjugate, e.g., CRLX101, or a CDP-inhibitor conjugate described herein, can be recovered at a purity greater than about 60%, greater than about 70%, greater than about 75%, greater than about 80%, greater than about 85%, greater than about 90%, greater than about 95%, greater than about 98%, or greater than about 99.0%.

In some embodiments, the CDP-inhibitor conjugate, e.g., CDP-camptothecin conjugate, e.g., CRLX101, or a CDP-inhibitor conjugate described herein, can be evaluated using dynamic light scattering (DLS), sometimes referred to as Photon Correlation Spectroscopy (PCS) or Quasi-Elastic Light Scattering (QELS) to determine the size of the particles, e.g., nanoparticles.

CDP-Topoisomerase Inhibitor Conjugates, Particles, and Compositions

Cyclodextrin-containing polymer (CDP) inhibitor conjugates, such as CDP-camptothecin conjugate, e.g., CRLX101, wherein one or more camptothecin, or camptothecin derivative, moieties are covalently attached to the CDP (e.g., either directly or through a linker) are described herein. Exemplary cyclodextrin-containing polymers that may be modified as described herein are taught in U.S. Pat. Nos. 7,270,808, 6,509,323, 7,091,192, 6,884,789, U.S. Publication Nos. 20040087024, 20040109888 and 20070025952.

In some embodiments, the CDP-inhibitor conjugate, e.g., CDP-camptothecin conjugate, e.g., CRLX101, or a CDP-inhibitor conjugate described herein, is as shown below:

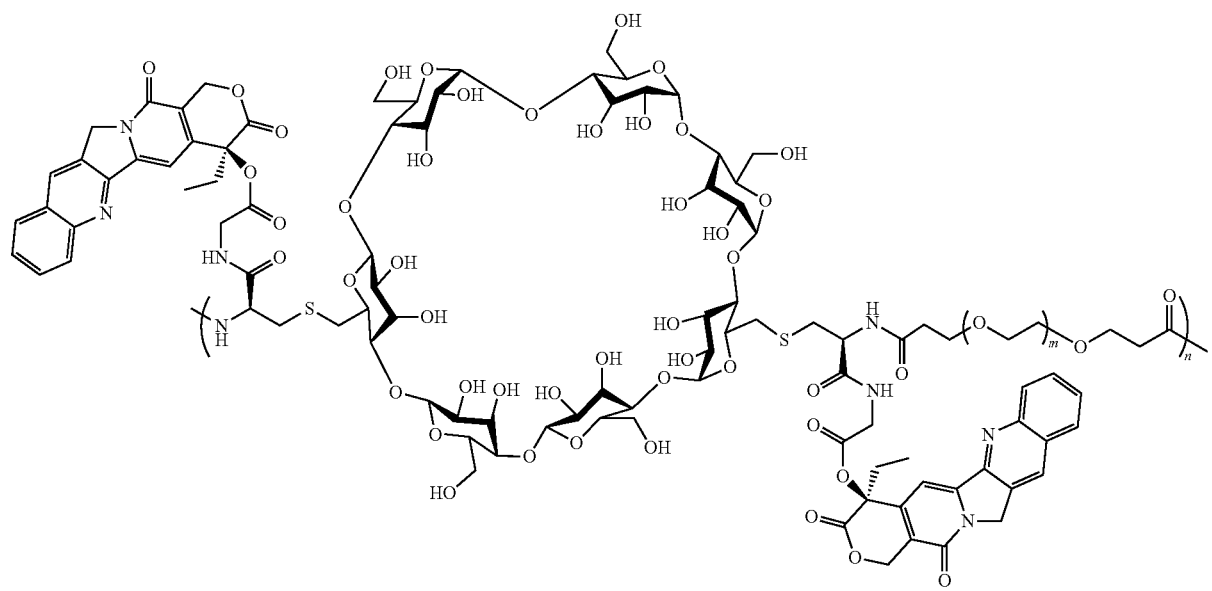

In the above structure:

m=about 77 or the molecular weight of the PEG moiety is 3.4 kDa, e.g., 3.4 kDa +/−10%;

n=is from about 10 to about 18 (e.g., about 14);

the molecular weight of the polymer backbone (i.e., the polymer minus the camptothecin-glycine (CPT-gly), which results in the cysteine moieties having a free —C(O)OH) is from about 48 to about 85 kDa;

the polydispersity of the polymer backbone is less than about 2.2; and the loading of the CPT onto the polymer backbone is from about 6 to about 13% by weight, wherein 13% is theoretical maximum, meaning, in some instances, one or more of the cysteine residues has a free —C(O)OH (i.e., it lacks the CPT-gly).

In some embodiments, the CDP-inhibitor conjugate, e.g., CDP-camptothecin conjugate, e.g., CRLX101, or a CDP-inhibitor conjugate described herein, is a polymer having the following formula:

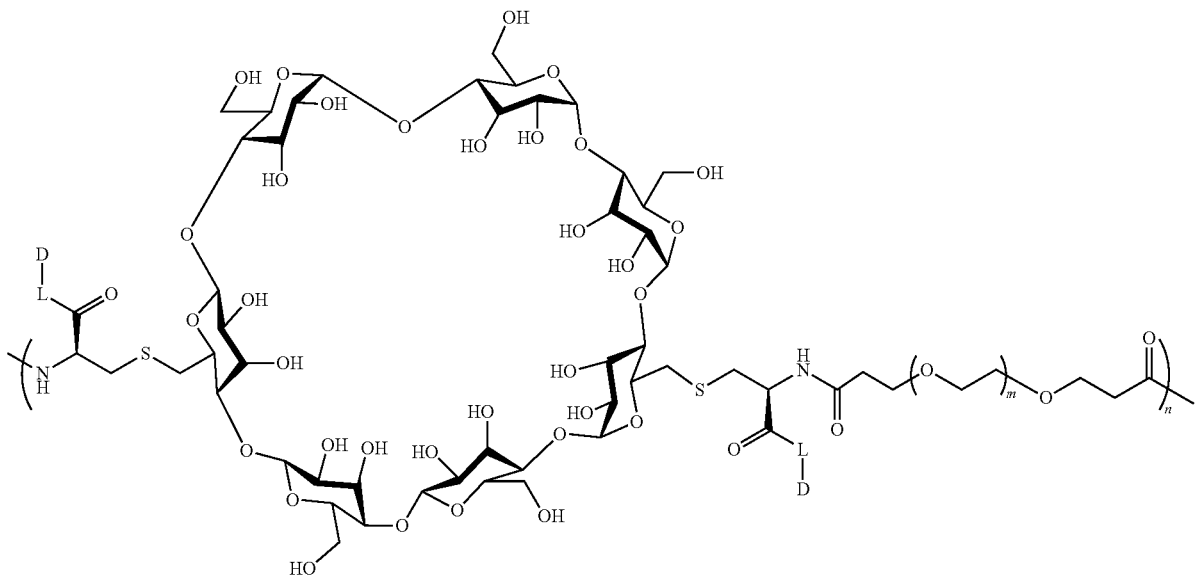

wherein

L, independently for each occurrence, is a linker (e.g, —NH—CH$_2$—CO—), a bond, or —OH;

D, independently for each occurrence, is camptothecin ("CPT") or a camptothecin derivative or absent, and the group

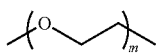

has a Mw of 3.4 kDa +/−10%, e.g. 3.4 kDa, or less (m can be, e.g., 77+/−8, e.g., about 77; and n is at least 4, e.g., 10-18, e.g., about 14, provided that at least one D is CPT or a camptothecin derivative.

In some embodiments, the loading of inhibitor moieties on the CDP-inhibitor conjugate, e.g., CDP-camptothecin conjugate, e.g., CRLX101, or a CDP-inhibitor conjugate described herein, is from about 1 to about 50% (e.g., from about 1 to about 25%, from about 5 to about 20% or from about 5 to about 15%, e.g., from about 6 to about 13% of the weight of the conjugate).

In some embodiments, the loading of inhibitor moieties on the CDP is from about 6% to about 13% by weight of the conjugate.

In embodiments, the molecular weight of the CDP backbone, without attached inhibitor moieties or linker moieties, is from about, 38-95 or 48-85 kDa.

In an embodiment m=77+/−8; n=about 14; and sufficient D is camptothecin such that camptothecin accounts for 6-13% by weight of the conjugate.

In an embodiment m=77+/−8; n=about 14; and sufficient D is a camptothecin derivative such that camptothecin derivative accounts for 6-13% by weight of the conjugate.

In an embodiment one or more of the cysteine residues has a free —C(O)OH (i.e., it lacks camptothecin or a camptothecin derivative).

In some embodiments, the CDP-inhibitor conjugate, has the following formula:

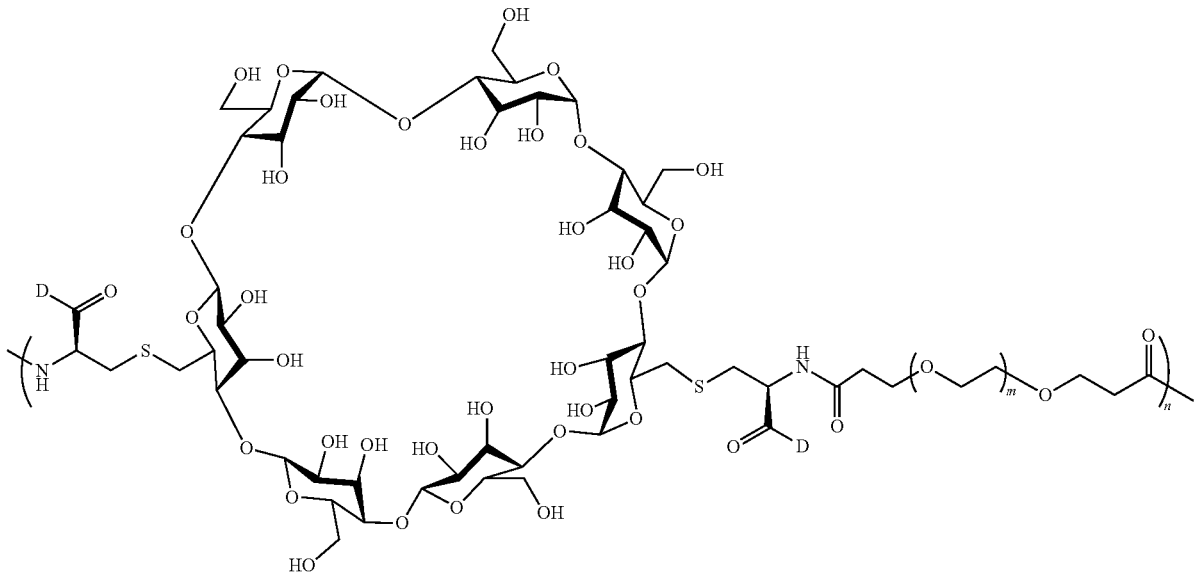

wherein
D=independently for each occurrence, is —OH or

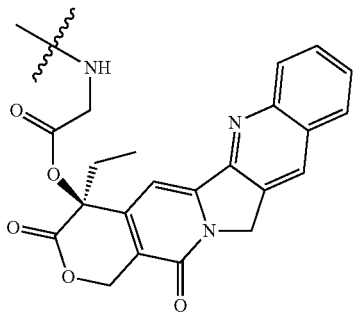 [SMILES: *NCC(=O)O[C@]1(CC)C(=O)OCc2c1cc1n(c2=O)Cc2cc3ccccc3nc2-1]

"camptothecin-glycine" (CPT-glycine); and
the group

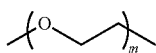

has a Mw of 3.4 kDa +/−10%, e.g., 3.4 kDa, or less (m can be, e.g., 77+/−8, e.g., about 77; and
n is 10-18, e.g., about 14,
provided that at least 1 D moiety is

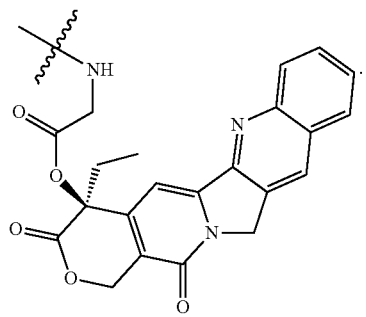 [SMILES: *NCC(=O)O[C@]1(CC)C(=O)OCc2c1cc1n(c2=O)Cc2cc3ccccc3nc2-1]

In an embodiment sufficient D moieties are

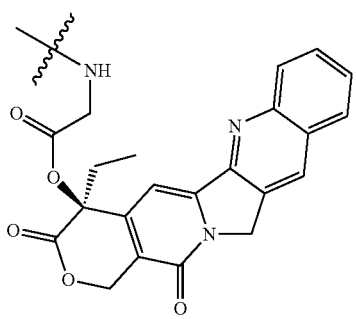 [SMILES: *NCC(=O)O[C@]1(CC)C(=O)OCc2c1cc1n(c2=O)Cc2cc3ccccc3nc2-1]

such that 6-13% by weight of the conjugate is camptothecin.

In embodiments, the molecular weight of the CDP backbone, without attached inhibitor moieties or linker moieties, is from about, 38-95 or 48-85 kDa.

In embodiments one or more of the cysteine residues has a free —C(O)OH (i.e., it lacks the CPT-glycine).

In an embodiment m=77+/−8; n=about 14; and sufficient D is camptothecin such that camptothecin accounts for 6-13% by weight of the conjugate.

In an embodiment one or more of the cysteine residues has a free —C(O)OH (i.e., it lacks the CPT-glycine).

Preparations of the CDP-Inhibitor Conjugates

In embodiments the polydispersity of the polymer backbone in a preparation of polymer backbone or CDP-camptothecin conjugates is less than about 2.2.

In embodiments the average value for n in a preparation of the camptothecin-inhibitor conjugate is about 14.

In embodiments, at least 5, 10, 20, 30, 40, 50, 60, 70, 80, 90, or 95% (e.g., by weight or number) of the CDP-camptothecin conjugate molecules in a preparation will have a value for n recited herein, e.g., 10-18.

In embodiments, at least 5, 10, 20, 30, 40, 50, 60, 70, 80, 90, or 95% (e.g., by weight or number) of the CDP backbone, without attached inhibitor moieties or linker moieties, in a preparation will have a molecular weight recited herein, e.g., 48-65 kDa. Molecular weight can be determined by gel permeation chromatography ("GPC"), e.g., mixed bed columns, $CH_2Cl_2$ solvent, light scattering detector, and off-line do/dc. Other methods are known in the art.

In some embodiments, the CDP-inhibitor conjugate, e.g., CDP-camptothecin conjugate, e.g., CRLX101, or a CDP-inhibitor conjugate described herein, particle or composition as described herein have polydispersities less than about 3, or even less than about 2.

In some embodiments, the polydispersity of the PEG is less than about 1.1.

Properties of the CDP-Inhibitor Conjugates

In some embodiments, administration of the CDP-inhibitor conjugate, e.g., CDP-camptothecin conjugate, e.g., CRLX101, or a CDP-inhibitor conjugate described herein, to a subject results in release of the inhibitor, e.g., camptothecin or camptothecin derivative, over a period of at least 6 hours. In some embodiments, administration of the CDP-inhibitor conjugate, e.g., CDP-camptothecin conjugate, e.g., CRLX101, or a CDP-inhibitor conjugate described herein, to a subject results in release of the inhibitor, e.g., camptothecin or camptothecin derivative, over a period of 2 hours, 3 hours, 5 hours, 6 hours, 8 hours, 10 hours, 15 hours, 20 hours, 1 day, 2 days, 3 days, 4 days, 7 days, 10 days, 14 days, 17 days, 20 days, 24 days, 27 days up to a month. In some embodiments, upon administration of the CDP-inhibitor conjugate, e.g., CDP-camptothecin conjugate, e.g., CRLX101, or a CDP-inhibitor conjugate described herein, to a subject, the rate of the inhibitor, e.g., camptothecin or camptothecin derivative, release is dependent primarily upon the rate of hydrolysis as opposed to enzymatic cleavage.

Exemplary CDP-Inhibitor Conjugates, Particles And Compositions

In embodiments, the CDP-inhibitor conjugate, e.g., CDP-camptothecin conjugate, e.g., CRLX101, or a CDP-inhibitor conjugate described herein, are in the form of a particle, e.g., a nanoparticle, comprising one or more molecules of a CDP-inhibitor conjugate, e.g., CDP-camptothecin conjugate, e.g., CRLX101, or a CDP-inhibitor conjugate described herein.

The nanoparticle ranges in size from 10 to 300 nm in diameter, e.g., 20 to 280, 30 to 250, 40 to 200, 20 to 150, 30 to 100, 20 to 80, 30 to 70, 40 to 60 or 40 to 50 nm diameter. In one embodiment, the particle is 50 to 60 nm, 20 to 60 nm, 30 to 60 nm, 35 to 55 nm, 35 to 50 nm or 35 to 45 nm in diameter.

In one embodiment, the surface charge of the molecule is neutral, or slightly negative. In some embodiments, the zeta potential of the particle surface is from about −80 mV to about 50 mV, about −20 mV to about 20 mV, about −20 mV to about −10 mV, or about −10 mV to about 0.

Cyclodextrin polymer (CDP) inhibitor conjugates, such as CDP-camptothecin conjugate, e.g., CRLX101, or a CDP-inhibitor conjugate described herein, particles and compositions of the disclosure may be useful to improve solubility and/or stability of the inhibitor, e.g., camptothecin or camptothecin derivative, reduce drug-drug interactions, reduce interactions with blood elements including plasma proteins, reduce or eliminate immunogenicity, protect the inhibitor, e.g., camptothecin or camptothecin derivative, from metabolism, modulate drug-release kinetics, improve circulation time, improve inhibitor half-life (e.g., in the serum, or in selected tissues, such as tumors), attenuate toxicity, improve efficacy, normalize inhibitor metabolism across subjects of different species, ethnicities, and/or races, and/or provide for targeted delivery into specific cells or tissues.

In other embodiments, the CDP-inhibitor conjugate, e.g., CDP-camptothecin conjugate, e.g., CRLX101, or a CDP-inhibitor conjugate described herein, particle or composition may be a flexible or flowable material. When the CDP used is itself flowable, the CDP composition of the disclosure, even when viscous, need not include a biocompatible solvent to be flowable, although trace or residual amounts of biocompatible solvents may still be present.

Physical Structures of the CDP-topoisomerase Inhibitor Conjugates, Particles and Compositions The CDP-inhibitor conjugate, e.g., CDP-camptothecin conjugate, e.g., CRLX101, or a CDP-inhibitor conjugate described herein, particles and compositions may be formed in a variety of shapes. For example, in certain embodiments, CDP-inhibitor conjugate, e.g., CDP-camptothecin conjugate, e.g., CRLX101, or a CDP-inhibitor conjugate described herein, may be presented in the form of microparticles or nanoparticles. Microspheres typically comprise a biodegradable polymer matrix incorporating a drug. Microspheres can be formed by a wide variety of techniques known to those of skill in the art. Examples of microsphere forming techniques include, but are not limited to, (a) phase separation by emulsification and subsequent organic solvent evaporation (including complex emulsion methods such as oil in water emulsions, water in oil emulsions and water-oil-water emulsions); (b) coacervation-phase separation; (c) melt dispersion; (d) interfacial deposition; (e) in situ polymerization; (f) spray drying and spray congealing; (g) air suspension coating; and (h) pan and spray coating. These methods, as well as properties and characteristics of microspheres are disclosed in, for example, U.S. Pat. Nos. 4,438,253; 4,652,441; 5,100,669; 5,330,768; 4,526,938; 5,889,110; 6,034,175; and European Patent 0258780, the entire disclosures of which are incorporated by reference herein in their entireties.

To prepare microspheres, several methods can be employed depending upon the desired application of the delivery vehicles. Suitable methods include, but are not limited to, spray drying, freeze drying, air drying, vacuum drying, fluidized-bed drying, milling, co-precipitation and critical fluid extraction. In the case of spray drying, freeze drying, air drying, vacuum drying, fluidized-bed drying and critical fluid extraction; the components (stabilizing polyol, bioactive material, buffers, etc.) are first dissolved or suspended in aqueous conditions. In the case of milling, the components are mixed in the dried form and milled by any method known in the art. In the case of co-precipitation, the components are mixed in organic conditions and processed as described below. Spray drying can be used to load the stabilizing polyol with the bioactive material. The components are mixed under aqueous conditions and dried using precision nozzles to produce extremely uniform droplets in a drying chamber. Suitable spray drying machines include, but are not limited to, Buchi, NIRO, APV and Lab-plant spray driers used according to the manufacturer's instructions.

The shape of microparticles and nanoparticles may be determined by scanning electron microscopy. Spherically shaped nanoparticles are used in certain embodiments, for circulation through the bloodstream. If desired, the particles may be fabricated using known techniques into other shapes that are more useful for a specific application.

In addition to intracellular delivery of an inhibitor, e.g., camptothecin or camptothecin derivative, it also possible that particles of the CDP-inhibitor conjugate, e.g., CDP-camptothecin conjugate, e.g., CRLX101, or a CDP-inhibitor conjugate described herein, such as microparticles or nanoparticles, may undergo endocytosis, thereby obtaining access to the cell. The frequency of such an endocytosis process will likely depend on the size of any particle.

In one embodiment, the surface charge of the molecule is neutral, or slightly negative. In some embodiments, the zeta potential of the particle surface is from about −80 mV to about 50 mV.

CDPs, Methods of Making Same, and Methods of Conjugating CDPs to Inhibitors

Generally, the CDP-inhibitor conjugate, e.g., CDP-camptothecin conjugate, e.g., CRLX101, or a CDP-inhibitor conjugate described herein, particles and compositions described herein can be prepared in one of two ways: monomers bearing inhibitors, e.g., camptothecin or camptothecin derivatives, targeting ligands, and/or cyclodextrin moieties. Exemplary methods of making CDPs and CDP-inhibitor conjugate, e.g., CDP-camptothecin conjugate, e.g., CRLX101, or a CDP-inhibitor conjugate described herein, particles and compositions are described, for example, in U.S. Pat. No. 7,270,808, the contents of which is incorporated herein by reference in its entirety.

EXAMPLES

Example 1: Synthesis of $6^A,6^D$-Bis-(2-amino-2-carboxylethylthio)-$6^A,6^D$-dideoxy-β-cyclodextrin, 4 (CD-BisCys)

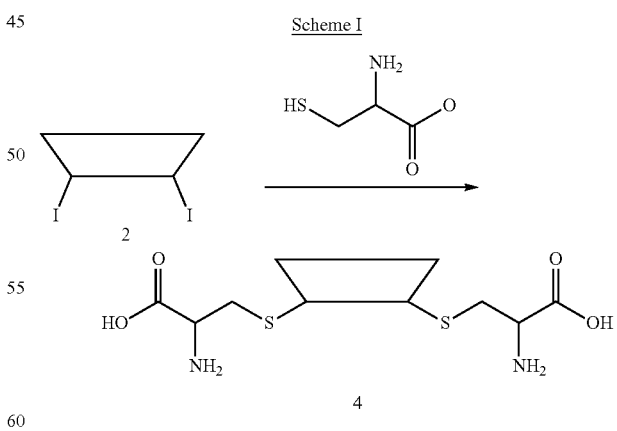

Scheme I 167 mL of 0.1 M sodium carbonate buffer were degassed for 45 minutes in a 500 mL 2-neck round bottom flask equipped with a magnetic stir bar, a condenser and septum. To this solution were added 1.96 g (16.2 mmol) of L-cysteine and 10.0 g (73.8 mmol) of diiodo, deoxy-β-cyclodextrin 2. The resulting suspension was heated at a reflux temperature for 4.5 h until the solution turned clear (colorless). The solution was then cooled to room temperature and acidified to pH 3 using 1N HCl. The product was precipitated by slow addition of acetone (3 times weight ratio of the solution). This afforded 9.0 g crude material containing CD-biscysteine (90.0%), unreacted cyclodextrin, CD-monocysteine and cysteine. The resulting solid was subjected to anionic exchange column chromatography (SuperQ650M, Tosoh Bioscience) using a gradient elution of 0-0.4M ammonium bicarbonate. All fractions were analyzed by HPLC. The desired fractions were combined and the solvent was reduced to 100 mL under vacuum. The final product was either precipitated by adding acetone or by adding methanol (3 times weight ratio of the solution). 4 was obtained in 60-90% yield. $^1$H NMR (D$_2$O) δ 5.08 (m, 7H, CD-2-CH), 3.79-3.94 (m, 30H, CD-3,4-CH, CD-CH$_2$, Cys-CH), 3.49-3.62 (m, 14H, CD-5, 6-CH), 2.92-3.30(m, 4H, Cys-CH$_2$). $^{13}$C NMR (D$_2$O) δ 172.3, 101.9, 83.9, 81.6, 81.5, 73.3, 72.2, 72.0, 60.7, 54.0, 34.0, 30.6. ESI/MS (m/z): 1342 [M]$^+$, 1364 [M+Na]$^+$. Purity of 4 was confirmed by HPLC.

Example 2: Synthesis of Gly-CPT (Structure 11) (Greenwald et al., *Bioorg. Med. Chem.*, 1998, 6, 551-562)

Scheme II

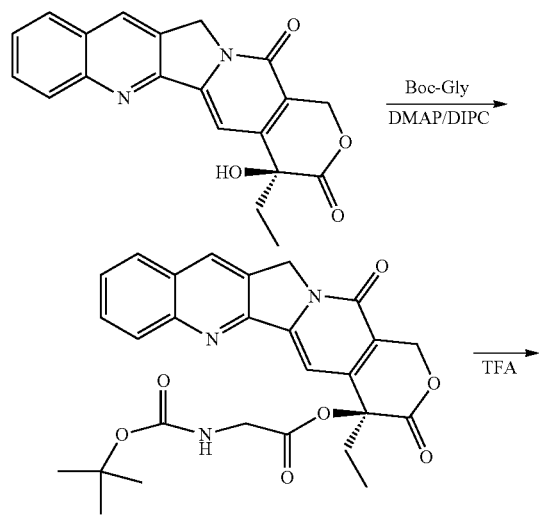

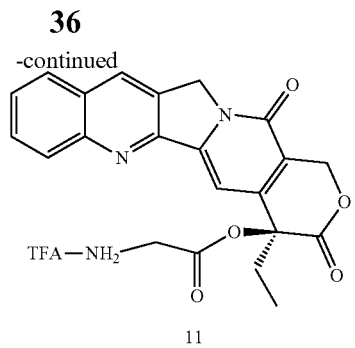

t-Boc-glycine (0.9 g, 4.7 mmol) was dissolved in 350 mL of anhydrous methylene chloride at room temperature, and to this solution were added DIPC (0.75 mL, 4.7 mmol), DMAP (382 mg, 3.13 mmol) and camptothecin (0.55 g, 1.57 mmol) at 0° C. The reaction mixture was allowed to warm to room temperature and left for 16 h. The solution was washed with 0.1 N HCl, dried and evaporated under reduced pressure to yield a white solid, which was recrystallized from methanol to give camptothecin-20-ester of t-Boc-glycine: $^1$H NMR(DMSO-d$_6$) 7.5-8.8 (m), 7.3 (s), 5.5 (s), 5.3 (s), 4 (m), 2.1 (m), 1.6 (s), 1.3 (d), 0.9 (t). Camptothecin-20-ester of t-Boc-glycine (0.595 g, 1.06 mmol) was dissolved in a mixture of methylene chloride (7.5 mL) and TFA (7.5 mL) and stirred at room temperature for 1 h. Solvent was removed and the residue was recrystallized from methylene chloride and ether to give 0.45 g of 11. $^1$H NMR (DMSO-d$_6$) δ7.7-8.5 (m); 7.2 (s), 5.6 (s), 5.4 (s), 4.4 (m), 2.2 (m), 1.6 (d), 1.0 (t), $^{13}$C NMR (DMSO-d$_6$) δ168.6, 166.6, 156.5, 152.2, 147.9, 146.2, 144.3, 131.9, 130.6, 129.7, 128.8, 128.6, 128.0, 127.8, 119.0, 95.0, 77.6, 66.6, 50.5, 47.9, 30.2, 15.9, 7.9. ESI/MS (m/z) expected 405; Found 406 (M+H).

Example 3: Synthesis and Characterization of CD-BisCys-Peg3400 Copolymers 36 and their CPT Conjugates 37

A. Synthesis and Characterization of CD-BisCys-Peg3400 Copolymers 36

Scheme IIIa

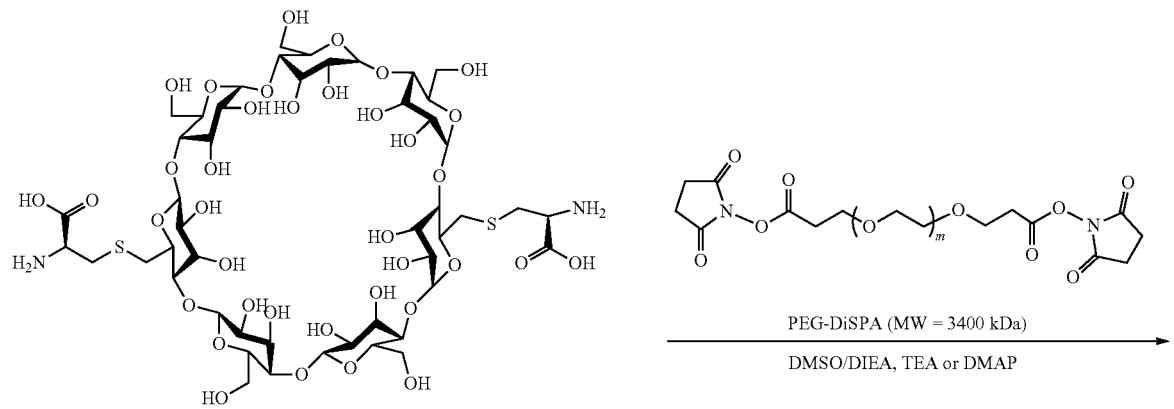

PEG-DiSPA (MW = 3400 kDa)

DMSO/DIEA, TEA or DMAP

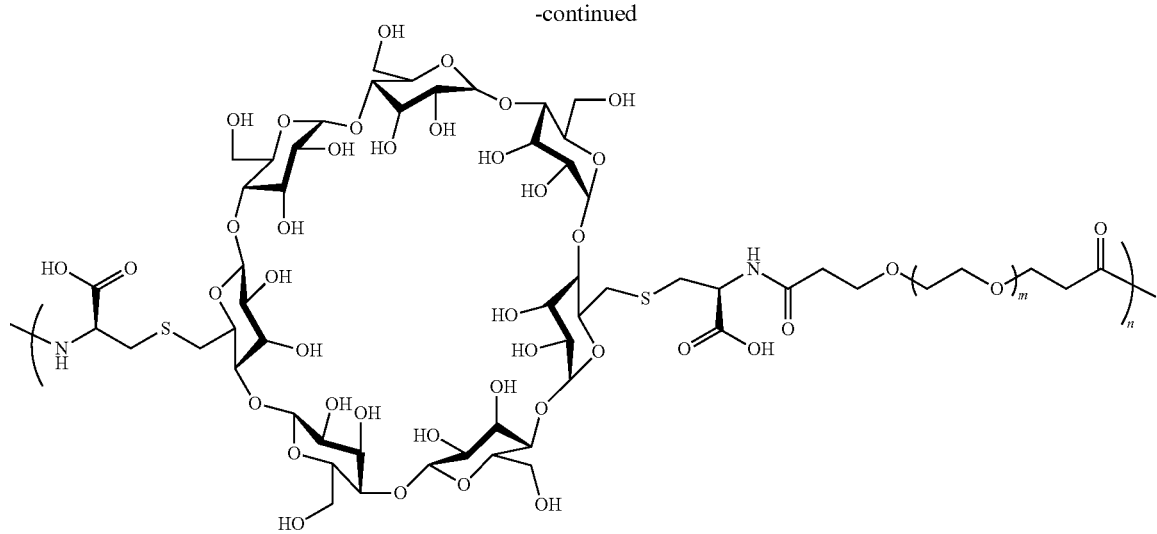
36a-f
Poly(CDDCys-PA-PEG)
Abbr: PA = propanoicamide bond between PEG and CD
Scheme IIIb
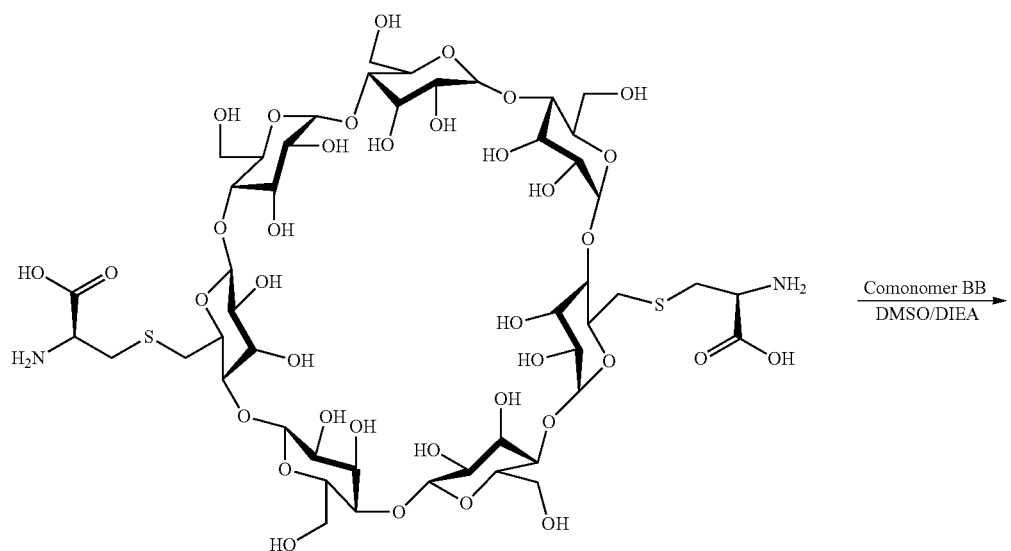
4
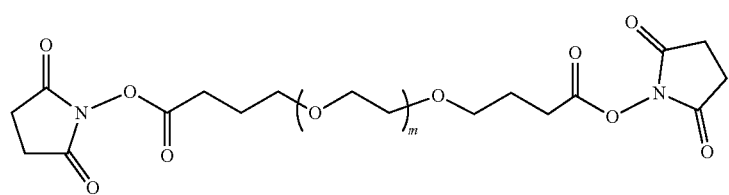
PEG-DiSBA (MW = 3400 kDa)

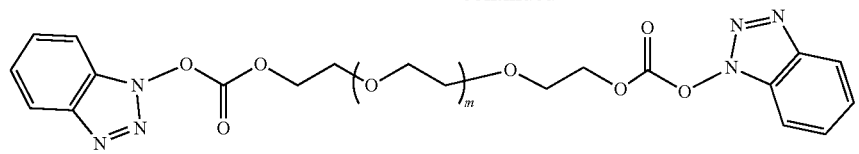
PEG-DiBTC (MW = 3400 kDa)
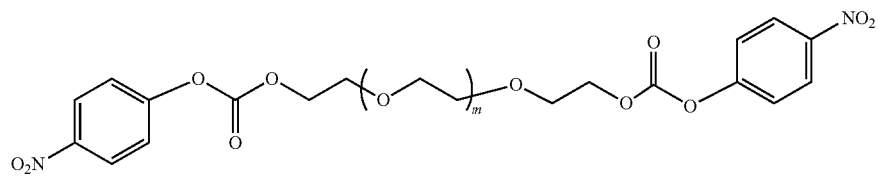
PEG-DiNPC (MW = 3400 kDa)
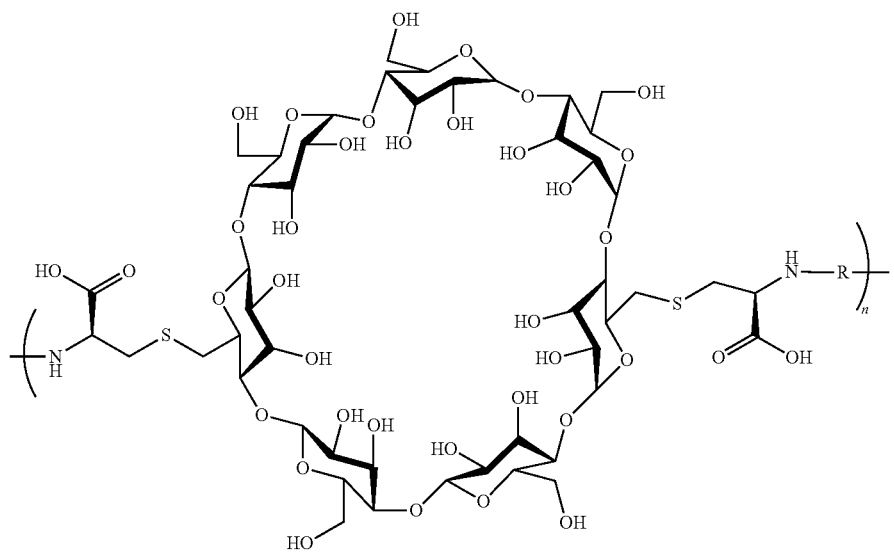
36g-i
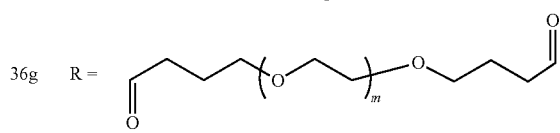
Poly(CDDCys-BA-PEG)
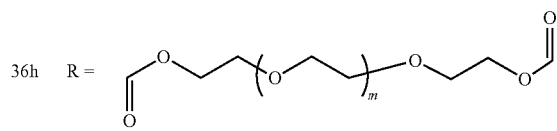
Poly(CDDCys-CB-PEG)
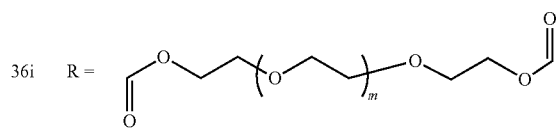
Poly(CDDCys-CB-PEG)
Abbr: BA = butanoicamide bond; CB = carbamate bond Synthesis of Poly(CDDCys-PA-PEG), 36a 4 (after precipitation with acetone, 63 mg, 0.047 mmol) and PEG-DiSPA (MW 3400, 160 mg, 0.047 mmol) were dried under vacuum for 8 hours. Anhydrous DMSO (1.26 mL) was added to the mixture under argon. After 10 minutes of stirring, anhydrous diisopropylethylamine (DIEA, 19 µL, 2.3 eq.) was added under argon. The reaction mixture was stirred under argon for 120 h. The polymer containing solution was dialyzed using a 10,000 MWCO membrane (Spectra/Por 7) against water for 48 h and lyophilized to yield 196 mg 36a. $M_w$=57400 Da, $M_n$=41700 Da, $M_w/M_n$=1.38. $^1$H NMR ($D_2O$) δ 5.08 (m, CD-2-H), 4.27 (m, Cys-CH), 2.72-3.76 (m, CD-3,4,5,6-CH, CD-$CH_2$, PEG-$CH_2$), 2.44 (m, Cys-$CH_2$).

Synthesis of other poly(CDDCys-PA-PEG) (36b-f), Poly(CDDCys-BA-PEG) (36g) Poly(CDDCys-CB-PEG) (36h-i) were achieved under polymerization condition similar to that of 36a. Details for the polymerization conditions, monomer selection, polymer molecular weight, polydispersity and yields are listed in Table 1. 36g: $^1$H NMR ($D_2O$) δ 5.10 (m, CD-2-H), 4.25-4.37 (m, Cys-CH), 2.72-3.86 (m, CD-3,4,5, 6-CH, CD-$CH_2$, PEG-$CH_2$), 2.21 (m, Cys-$CH_2$). 36h-i: $^1$H NMR ($D_2O$) δ 5.05 (m, CD-2-H), 4.56 (m, Cys-CH), 2.70-3.93 (m, CD-3,4,5,6-CH, CD-$CH_2$, PEG-$CH_2$), 2.38 (m, —$OCH_2CH_2C(O)$—NH—), 2.34 (m, Cys-$CH_2$), 1.90 (m, —$OCH_2CH_2C(O)$—NH—).

Addition of a non-nucleophilic organic base (such as DIEA) was essential for this polymerization as no viscosity changes of the polymerization solutions were observed after 48 hours if no base was added. When 2.3 eq. of DIEA were added, the viscosity of the polymerization solution increased dramatically after 4-6 hours of reaction. DIEA deprotonates the amino groups of 4 to render them more nucleophilic for coupling with PEG-DiSPA. There were essentially no differences in the polymerizations if other bases, such as TEA or DMAP, were used (36b-c, Table 1). Polymerization using 4 recovered by the two different precipitation methods (acetone and methanol) produced polymers with different MWs. 4 that was purified by the methanol-precipitation method (contains no free cysteine) gave higher MW polymer (36d-e) as compared to the less pure 4 that was obtained from the acetone-precipitation method (36a). Polymerization of 4 with PEG-DiSPA typically produced polymer yields greater than 90%.

4 was polymerized with other activated monomers such as PEG-DiSBA, PEG-DiBTC, and PEG-DiNPC. Reaction of 4 with PEG-DiSBA gave polymer 36g with similar linkages as 36a-f (amide bond, but one more —$CH_2$ group than 36a-f at the linker) with $M_w$ over 100,000 Da, while reaction of 4 with PEG-DiBTC and PEG-DiNPC generated polymers 36h and 36i, respectively, with connecting carbamate moiety and $M_w$'s over 50,000 Da (Table 1).

TABLE 1

| | Polymerization of 4 with Difunctionalized PEG | | | | | | |
|---|---|---|---|---|---|---|---|
| CDP | PEG Comonomer | Base | Polymerization time (h) | $M_w$ (kDa) | $M_n$ (kDa) | $M_w/M_n$ | Yield (%) |
| 36a[a] | PEG-DiSPA | DIEA | 120 | 57.4 | 41.7 | 1.38 | 90 |
| 36b[a] | PEG-DiSPA | DMAP | 120 | 54.2 | 38.1 | 1.42 | 91 |
| 36c[a] | PEG-DiSPA | TEA | 120 | 57.4 | 42.6 | 1.35 | 91 |
| 36d[b] | PEG-DiSPA | DIEA | 120 | 93.6 | 58.0 | 1.48 | 96 |
| 36e[b] | PEG-DiSPA | DIEA | 144 | 97.3 | 58.0 | 1.67 | 94 |
| 36f[b] | PEG-DiSPA | DIEA | 2 | 35.3 | 25.6 | 1.38 | 95 |
| 36g | PEG-DiSBA | DIEA | 120 | 114.7 | 77.9 | 1.47 | 96 |
| 36h | PEG-DiBTC | DIEA | 120 | 67.6 | 39.4 | 1.47 | 95 |
| 36i | PEG-DiNPC | DIEA | 120 | 86.5 | 57.2 | 1.51 | 96 |

[a] 4 was washed with acetone before polymerization.
[b] 4 was washed with methanol before polymerization.

Polymers 36a-i are highly soluble in aqueous solution. They can be easily dissolved in water or phosphate buffered saline (PBS) solution at concentrations of at least 200 mg/mL. Solubility of these polymers in aqueous solution at concentrations higher than 200 mg/mL was not attempted due to the high viscosity. These polymers were also soluble in DMF, DMSO and methanol, slightly soluble in $CH_3CN$ and $CHCl_3$, but insoluble in THF and ethyl ether.

Molecular Weight Control of CD Polymers 4 (after precipitation with methanol) (56.2 mg, 0.0419 mmol) and PEG-DiSPA (147 mg, 0.0419 mmol) were dried under vacuum for 4-8 hours. To the mixture was added dry DMSO (1.1 mL) under argon. After 10 minutes stirring, DIEA (16 µL, 2.2 eq) was added under argon. A portion of polymerization solution (150 µL) was removed and precipitated with ether at selected times (2 h, 18 h, 43 h, 70 h, 168 h and 288 h). MWs of the precipitated polymers were determined as described above.

B. Synthesis of Poly(CDDCys-PA-PEG)-CPTConjugates (HGGG6, LGGG10, HG6, HGGG10).

Scheme IV

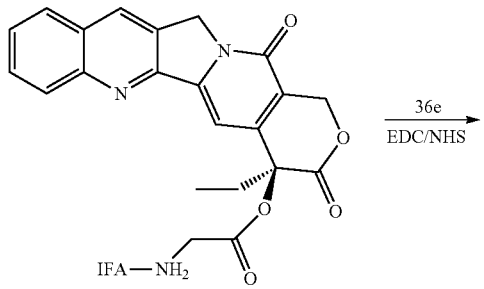

11

-continued
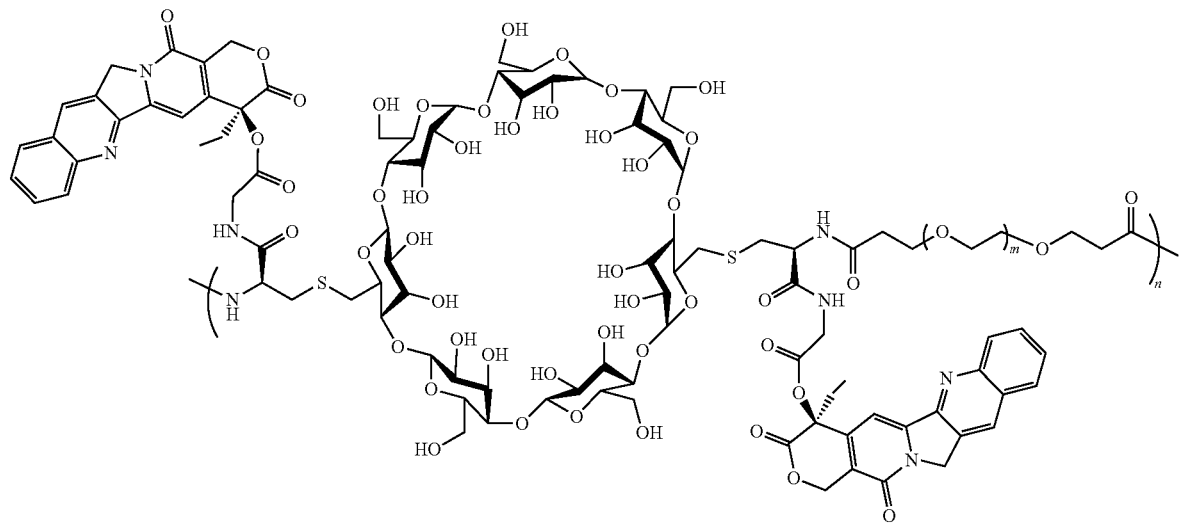
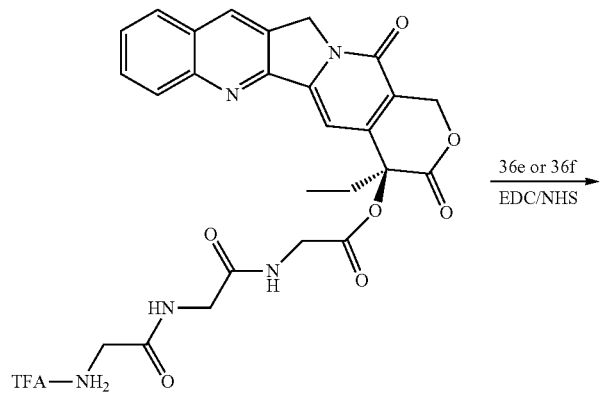

-continued

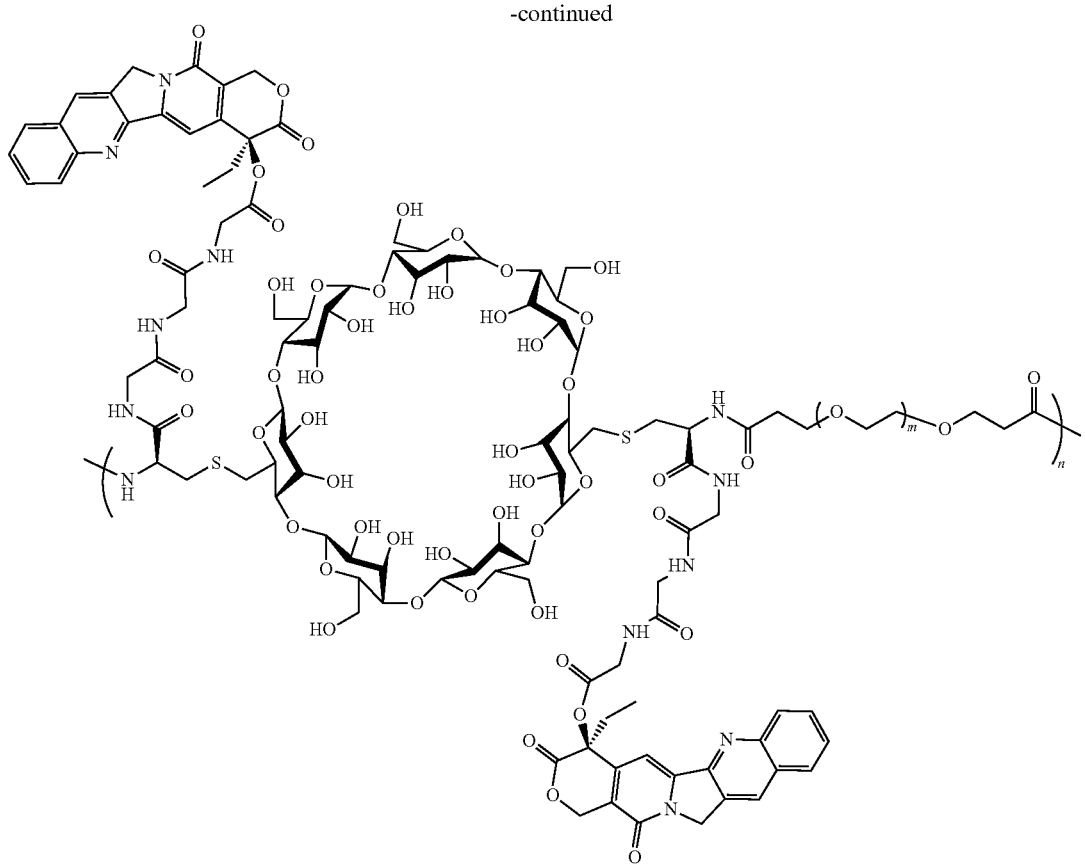

Synthesis of Poly(CDDCys-PA-PEG)-GlyGlyGly-CPT (HGGG6): 36e (1.37 g, 0.30 mmol of repeat unit) was dissolved in dry DMSO (136 mL). The mixture was stirred for 10 minutes. 12 (419 mg, 0.712 mmol, 2.36 eq), DIEA (0.092 mL, 0.712 mmol, 2.36 eq), EDC (172 mg, 0.903 mmol, 3 eq), and NHS (76 mg, 0.662 mmol, 2.2 eq) were added to the polymer solution and stirred for ca. 15 hours. The polymer was precipitated with ethyl ether (1 L). The ether was poured out and the precipitate was washed with $CH_3CN$ (3×100 mL). The precipitate was dissolved in water 600 mL. Some insoluble solid was filtered through 0.2 μm filters. The solution was dialyzed using 25,000 MWCO membrane (Spectra/Por 7) for 10 h at 10-15° C. in DI water. Dialysis water was changed every 60 minutes. The polymer-drug conjugate solution was sterilized by passing it through 0.2 μM filters. The solution was lyophilized to yield a yellow solid HGGG6 (1.42 g, 85% yield).

Synthesis of Poly(CDDCys-PA-PEG)-GlyGlyGly-CPT (LGGG10): Conjugation of 12 to 36f was performed in a manner similar to that used to produce HGGG6 except that this conjugate was dialyzed with 10,000 MWCO membrane (Spectra/Por 7) instead of with 25,000 MWCO membrane. The yield of LGGG10 was 83%.

Synthesis of Poly(CDDCys-PA-PEG)-Gly-CPT (HG6): Conjugation of 11 to 36e was performed in a manner similar to that used to produce HGGG6. The yield of HG6 was 83%.

Synthesis of Poly(CDDCys-PA-PEG)-GlyGlyGly-CPT (HGGG10): 36e (1.5 g, 0.33 mmol of repeat unit) was dissolved in dry DMSO (150 mL). The mixture was stirred for 10 minutes. 12 (941 mg, 1.49 mmol, 4.5 eq), DIEA (0.258 mL, 1.49 mmol, 4.5 eq), EDC (283 mg, 1.49 mmol, 4.5 eq), and NHS (113 mg, 0.99 mmol, 3 eq) was added to the polymer solution and stirred for ca. 24 hours. Another portion of EDC (142 mg, 0.75 mmol, 2.3 eq) and NHS (56 mg, 0.5 mmol, 1.5 eq) were added to the conjugation solution. The polymer was stirred for an additional 22 hours. The workup procedure was the same as that for the synthesis of HGGG6. The yield of HGGG10 was 77%.

Example 4: Chilled Precipitation of Poly(CDDCys-PA-PEG)-Gly-CPT (HG6)

Figure 3:
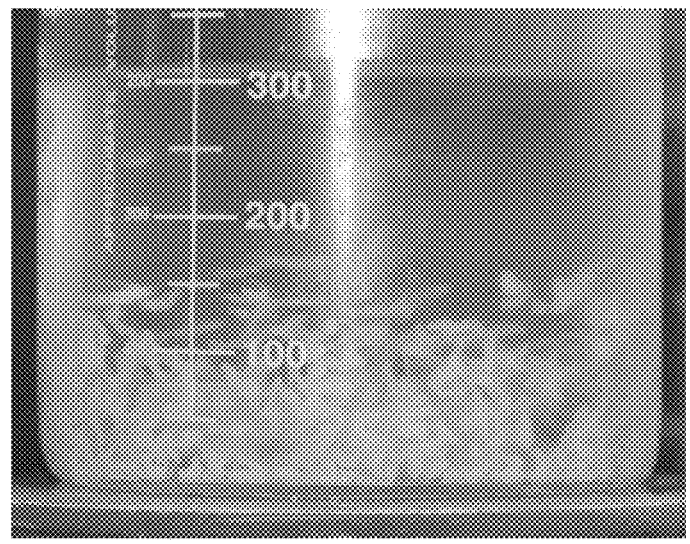
FIG. 3 depicts a beaker containing precipitated CRLX101 in cooled acetone.

A 600 mL beaker of 300 mL of acetone with magnetic stir bar was pre-chilled to −78° C. in a dry ice/acetone bath. A solution of polymer conjugate HG6 (2 grams), obtained without further preparation from Example 3, was added dropwise over a 4 minute period into the beaker with chilled acetone with stirring and maintained in the dry ice/acetone bath. Individual free flowing polymer particles (resembling chards or flakes) were formed (FIG. 3) and remained in suspension under stirring conditions. After 25 minutes, the chilled acetone was decanted and replaced with fresh pre-chilled acetone (300 mL at −78° C.) and stirred for an additional 30 minutes to afford a suspension of polymer particles in chilled acetone.

Figure 4:
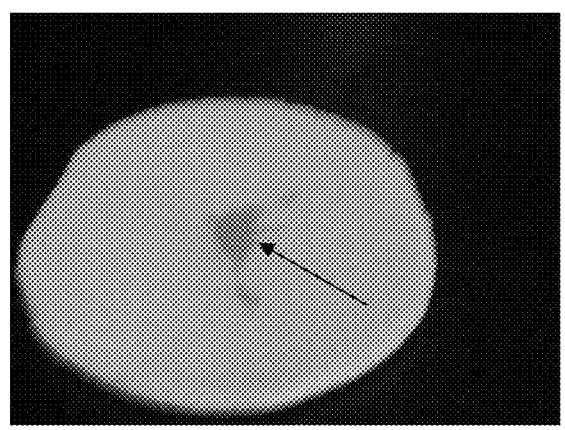
FIG. 4 depicts CRLX101 as an oil at room temperature.
Figure 5:
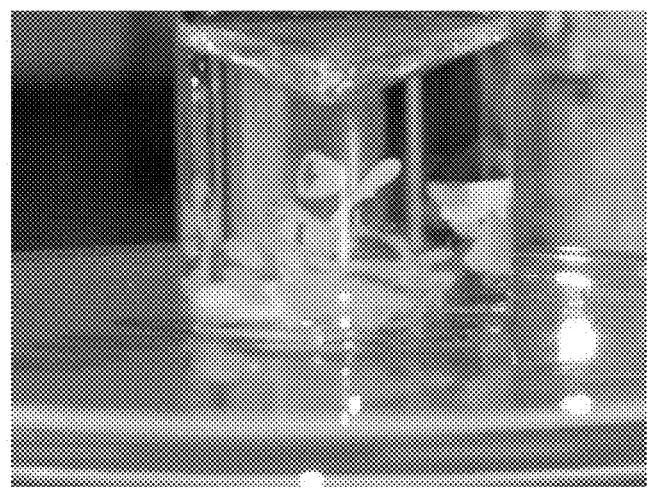
FIG. 5 depicts a free flowing suspension of CRLX101 in acetone at room temperature.

From the polymer particles/chilled acetone suspension further steps were conducted. First, a portion of polymer particles (still in acetone) was removed from the suspension and allowed to dry at room temperature. The polymer particles eventually melted into yellow oil (FIG. 4). A second portion of polymer particles (still in acetone) was removed from the suspension and frozen in liquid nitrogen ($N_2$) and lyophilized for 24 hours. Polymer particles maintained their shape immediately after lyophilization, but did not re-disperse in water even after 24 hours and sonication. With addition of acetone, however, re-dispersion was successful. A sample of lyophilized polymer particles was exposed to the ambient environment, and eventually melted into yellow oil. A third portion of polymer particles (still in acetone) was removed from the suspension and was warmed to room temperature for 72 hours and remained a stable free flowing suspension (FIG. 5).

The above described results indicate that HCG at cold temperatures may be precipitated as particles (resembling chards or flakes). The stability of the particles was maintained if the particles remained in an acetone (or possibly a vacuum environment). On exposure to ambient environment, the particles melted into an oil.

The polymer particles will be characterized using dynamic light scattering to determine the size distribution profile of these particles.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A process for precipitating a cyclodextrin-containing polymer (CDP)-camptothecin conjugate from a polymer-containing solution to form a CDP-camptothecin conjugate containing particle, the process comprising:
providing a vessel containing a first volume of a cooled non-solvent;
agitating the cooled non-solvent;
introducing the polymer-containing solution into the cooled non-solvent to form a mixture comprising a liquid and the CDP-camptothecin conjugate; and
maintaining the mixture under conditions to precipitate at least a portion of the CDP-camptothecin conjugate from the mixture;
thereby precipitating at least a portion of the CDP-camptothecin conjugate to form the CDP-camptothecin conjugate containing particle,
wherein at least a portion of the liquid from the vessel is removed subsequent to the precipitation of the CDP-camptothecin conjugate, a second volume of a cooled non-solvent added to the mixture, and the mixture is filtered to separate the CDP-camptothecin conjugate containing particle from the mixture, and
wherein the CDP-camptothecin conjugate containing particle has a polydispersity of less than about 2, and a particle size equal to or less than about 100 nm.

2. The process of claim 1, wherein the CDP-camptothecin conjugate is CRLX101, wherein CRLX101 is shown by the following structure:

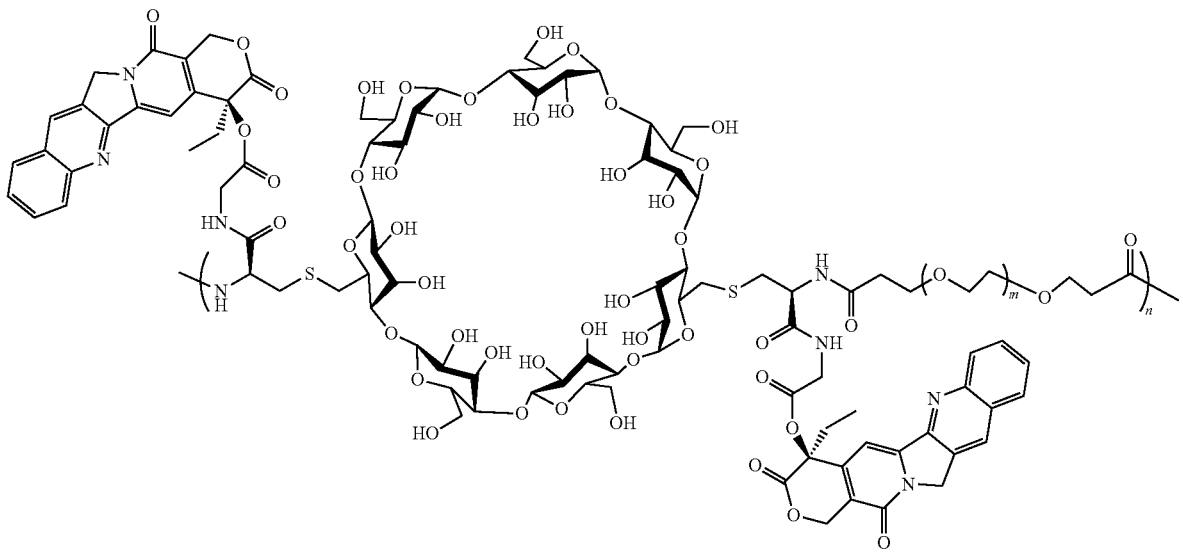

wherein:
m is about 77, or the group

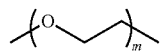

has a molecular weight of 3.4 kDa +/−10%; and
n is from about 10 to about 18.

3. The process of claim 1, wherein the mixture is maintained at a temperature of about −50 to about −100 degrees Celsius.

4. The process of claim 1, wherein the precipitated CDP-camptothecin conjugate containing particle is filtered at a temperature of about −50 degrees Celsius to about −100 degrees Celsius.

5. The process of claim 4, further comprising storing the filtered precipitated CDP-camptothecin conjugate containing particle in the cooled non-solvent.

6. The process of claim 1, wherein the cooled non-solvent comprises acetone.

7. The process of claim 1, wherein the temperature of the cooled non-solvent is from about −50 to about −100 degrees Celsius.

8. The process of claim 7, wherein the temperature of the cooled non-solvent is about −78 degrees Celsius.

9. The process of claim 1, wherein the cooled non-solvent comprises methanol, ethanol, acetone, n-propanol, isopropanol, n-butanol, ethyl ether, methyl isobutyl ketone or ethyl acetate or a combination thereof.

10. The process of claim 1, further comprising collecting the particle.

11. The process of claim 10, further comprising lyophilizing the collected particle.

12. The process of claim 2, wherein the molecular weight of the polymer backbone of the CDP-camptothecin conjugate is from about 48 to about 85 kDa.

13. The process of claim 2, wherein the loading of the camptothecin onto the cyclodextrin-containing polymer is from about 6 to about 13% by weight.

14. A process for generating particles, comprising:
providing a vessel containing a first volume of a cooled non-solvent; agitating the cooled non-solvent; introducing a polymer-containing solution comprising a CDP-camptothecin conjugate into the cooled non-solvent to form a mixture comprising a liquid and the CDP-camptothecin conjugate; maintaining the mixture under conditions to precipitate at least a portion of the CDP-camptothecin conjugate from the mixture; thereby precipitating at least a portion of the CDP-camptothecin conjugate; wherein at least a portion of the liquid from the vessel is removed subsequent to the precipitation of the CDP-camptothecin conjugate, and a second volume of a cooled non-solvent added to the mixture; isolating at least a portion of the precipitated CDP-camptothecin conjugate; and suspending the precipitated CDP-camptothecin conjugate in an aqueous solution, thereby generating particles, wherein the aqueous suspension of particles is subjected to tangential flow filtration, and wherein the particles have a polydispersity of less than about 2, and an average particle size equal to or less than about 100 nm.

15. The process of claim 14, wherein the CDP-camptothecin conjugate is CRLX101, wherein CRLX101 is shown by the following structure:

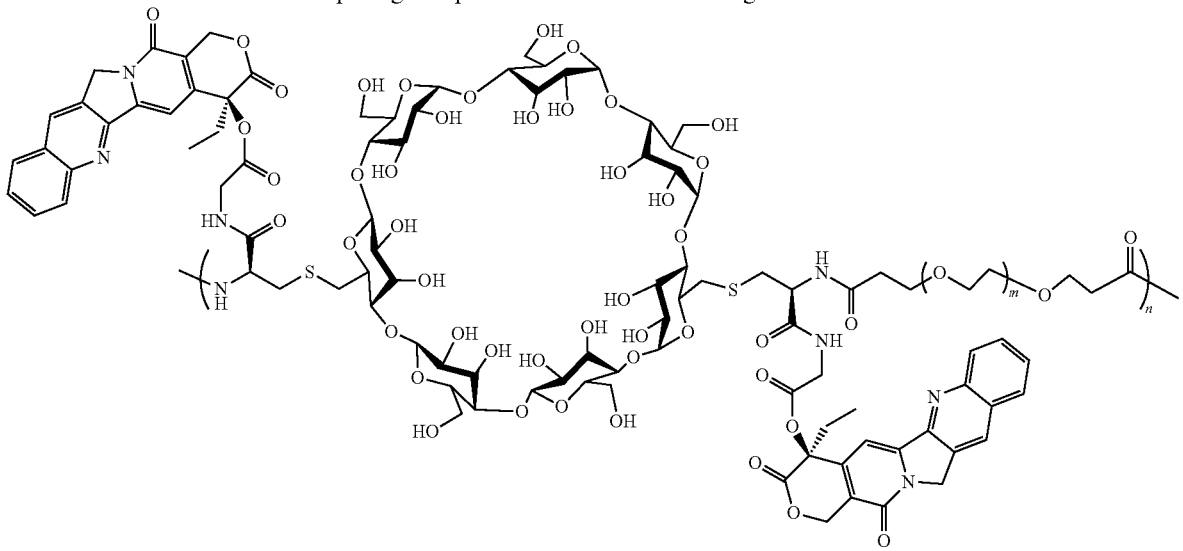

wherein:
m is about 77, or the group

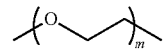

has a molecular weight of 3.4 kDa +/−10%; and n is from about 10 to about 18.

16. The process of claim 14, wherein the cooled non-solvent comprises methanol, ethanol, acetone, n-propanol, isopropanol, n-butanol, ethyl ether, methyl isobutyl ketone or ethyl acetate or a combination thereof.

17. The process of claim 14, further comprising filtering the particles at a temperature of about −50 degrees Celsius to about −100 degrees Celsius.

18. The process of claim 17, further comprising collecting the filtered particles.

19. The process of claim 18, further comprising lyophilizing the collected particles.

20. The process of claim 15, wherein the molecular weight of the polymer backbone of the CDP-camptothecin conjugate is from about 48 to about 85 kDa.

21. The process of claim 15, wherein the loading of the camptothecin onto the cyclodextrin-containing polymer is from about 6 to about 13% by weight.

* * * * *